US011241270B2

(12) United States Patent
Weinkam et al.

(10) Patent No.: US 11,241,270 B2
(45) Date of Patent: *Feb. 8, 2022

(54) SYSTEMS AND METHODS FOR ACTIVATING TRANSDUCERS

(71) Applicant: Kardium Inc., Burnaby (CA)

(72) Inventors: Daniel R. Weinkam, Coquitlam (CA); Daniel M. Reinders, Richmond (CA)

(73) Assignee: KARDIUM INC., Burnaby (CA)

( * ) Notice: Subject to any disclaimer, the term of this patent is extended or adjusted under 35 U.S.C. 154(b) by 328 days.

This patent is subject to a terminal disclaimer.

(21) Appl. No.: 16/587,480

(22) Filed: Sep. 30, 2019

(65) Prior Publication Data
US 2020/0030019 A1    Jan. 30, 2020

Related U.S. Application Data

(63) Continuation of application No. 15/581,364, filed on Apr. 28, 2017, now Pat. No. 10,470,815, which is a (Continued)

(51) Int. Cl.
A61B 18/12    (2006.01)
A61B 18/14    (2006.01)
(Continued)

(52) U.S. Cl.
CPC ......... *A61B 18/1206* (2013.01); *A61B 5/287* (2021.01); *A61B 18/1492* (2013.01); (Continued)

(58) Field of Classification Search
CPC ............ A61B 18/1206; A61B 18/1492; A61B 2018/00267; A61B 2018/00357; (Continued)

(56) References Cited

U.S. PATENT DOCUMENTS 5,462,545 A    10/1995    Wang
5,971,980 A    10/1999    Sherman
(Continued)

FOREIGN PATENT DOCUMENTS

WO    9858681 A2    12/1998
WO    2010056771 A1    5/2010
(Continued)

OTHER PUBLICATIONS

Communication under Rule 71(3) EPC issued in European Appln. No. 18212836.3 dated Apr. 20, 2020.
(Continued)

*Primary Examiner* — Daniel W Fowler
(74) *Attorney, Agent, or Firm* — Rossi, Kimms & McDowell LLP

(57)    ABSTRACT

In some embodiments, a plurality of transducers of a transducer-based device may be selected for activation. A first pair of subsets of the selected transducers may be identified for initial activation, each subset of the first pair being activated with a different phase angle range than the other. No transducer in one subset is sufficiently close to a transducer in the other subset to cause a confluence of ablated tissue regions therebetween. The first pair of subsets may be activated simultaneously or concurrently. Upon activation or a conclusion thereof of the pair of subsets of the selected transducers, one or more subsequent pairs of subsets of the selected transducers may be activated iteratively on a pair-by-pair basis, until all of the selected transducers have achieved desired activation results, according to some embodiments. Each subsequent pair may include the same or similar characteristics as the first pair.

36 Claims, 14 Drawing Sheets

Related U.S. Application Data continuation of application No. PCT/US2014/066143, filed on Nov. 18, 2014.

(51) Int. Cl.
  *A61B 5/287* (2021.01)
  *A61B 18/00* (2006.01)
  *A61B 5/107* (2006.01)

(52) U.S. Cl.
  CPC ..... *A61B 5/1076* (2013.01); *A61B 2018/0016* (2013.01); *A61B 2018/0075* (2013.01); *A61B 2018/00267* (2013.01); *A61B 2018/00357* (2013.01); *A61B 2018/00577* (2013.01); *A61B 2018/00642* (2013.01); *A61B 2018/00678* (2013.01); *A61B 2018/00708* (2013.01); *A61B 2018/00791* (2013.01); *A61B 2018/00839* (2013.01); *A61B 2018/00875* (2013.01); *A61B 2018/124* (2013.01)

(58) Field of Classification Search
  CPC .......... A61B 2018/00577; A61B 2018/00642; A61B 2018/00678; A61B 2018/00708; A61B 2018/0075; A61B 2018/00791; A61B 2018/0839; A61B 5/0422; A61B 5/1076

See application file for complete search history.

(56) References Cited

U.S. PATENT DOCUMENTS

| | | | |
|---|---|---|---|
| 5,991,650 | A | 11/1999 | Swanson |
| 6,023,638 | A | 2/2000 | Swanson |
| 6,045,550 | A | 4/2000 | Simpson |
| 8,295,902 | B2 | 10/2012 | Salahieh |
| 9,492,228 | B2 | 11/2016 | Lopes |
| 2002/0087156 | A1 | 7/2002 | Maguire |
| 2002/0123749 | A1 | 9/2002 | Jain |
| 2002/0161361 | A1 | 10/2002 | Sherman |
| 2004/0260346 | A1 | 12/2004 | Overall |
| 2008/0004534 | A1 | 1/2008 | Gelbart |
| 2008/0183251 | A1 | 7/2008 | Azar |
| 2009/0131930 | A1 | 5/2009 | Gelbart |
| 2010/0179524 | A1* | 7/2010 | Whayne ............. A61B 18/1206 606/14 |
| 2012/0197243 | A1 | 8/2012 | Sherman |
| 2013/0066220 | A1 | 3/2013 | Weinkam |
| 2013/0190587 | A1 | 7/2013 | Lopes |
| 2013/0310702 | A1 | 11/2013 | Reinders |
| 2014/0276769 | A1 | 9/2014 | Goertzen |
| 2016/0135882 | A1 | 5/2016 | Weinkam |
| 2019/0231423 | A1 | 8/2019 | Weinkam |

FOREIGN PATENT DOCUMENTS

| | | |
|---|---|---|
| WO | 2012100184 A2 | 7/2012 |
| WO | 2012100185 A2 | 7/2012 |

OTHER PUBLICATIONS

"Constellation Mapping Catheters", Brochure, Boston Scientific Corp., 2 pgs, © 2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
Invitation to Pay Additional Fees and, Where Applicable, Protest Fee issued in Intl. Appln. No. PCT/US2014/066143 dated Feb. 5, 2015.
International Search Report issued in Intl. Appln. No. PCT/US2014/066143 dated Mar. 31, 2015.
Written Opinion issued in Intl. Appln. No. PCT/US2014/066143 dated Mar. 31, 2015.
Office Action issued in U.S. Appl. No. 13/596,774 dated Apr. 15, 2015.
Amendment filed in U.S. Appl. No. 13/596,774 dated Jun. 30, 2015.
Office Action issued in U.S. Appl. No. 13/596,774 dated Jul. 27, 2015.
Amendment filed in U.S. Appl. No. 13/596,774 dated Oct. 19, 2015.
Notice of Allowance issued in U.S. Appl. No. 13/596,774 dated Nov. 3, 2015.
Office Action issued in copending U.S. Appl. No. 15/007,594 dated Mar. 17, 2016.
Amendment filed in copending U.S. Appl. No. 15/007,594 dated Sep. 13, 2016.
Office Action issued in copending U.S. Appl. No. 15/007,594 dated Oct. 21, 2016.
Amendment filed in copending U.S. Appl. No. 15/007,594 dated Feb. 10, 2017.
Office Action issued in copending U.S. Appl. No. 15/007,594 dated Mar. 30, 2017.
Office Action issued in copending U.S. Appl. No. 15/007,594 dated Jul. 19, 2017.
Amendment filed in copending U.S. Appl. No. 15/007,594 dated Jun. 30, 2017.
Extended European Search Report issued in European Appln. No. 14906383.6 dated Oct. 23, 2017.
Reply to Office Action filed in U.S. Appl. No. 15/007,594 dated Oct. 12, 2017.
Office Action issued in U.S. Appl. No. 15/007,594 dated Nov. 28, 2017.
Lau et al. "A Theoretical and Experimental Analysis of Radiofrequency Ablation with a Multielectrode, Phased, Duty-Cycled System." PACE. Sep. 2010: 1089-1100. vol. 33. The Authors. Journal compilation. Wiley Periodicals, Inc.
Amendment filed in co-pending U.S. Appl. No. 15/007,594, filed Feb. 26, 2018.
Office Action issued in co-pending U.S. Appl. No. 15/007,594 dated May 4, 2018.
Communication under Rule 71(3) EPC issued in European Appln. No. 14906383.6 dated Aug. 2, 2018.
Office Action issued in copending U.S. Appl. No. 15/007,594 dated Oct. 10, 2018.
Response to Office Action filed in copending U.S. Appl. No. 15/007,594 dated Aug. 28, 2018.
Extended European Search Report issued in copending European Appln. No. 18212836.3 dated Mar. 22, 2019.
Amendment filed in copending U.S. Appl. No. 15/007,594 dated Jan. 9, 2019.
Notice of Allowance issued in copending U.S. Appl. No. 15/007,594 dated Apr. 24, 2019.
Preliminary Amendment filed in copending U.S. Appl. No. 16/380,325, filed May 3, 2019.
Notice of Allowance issued in copending U.S. Appl. No. 15/581,364 dated Jul. 29, 2019.
Extended European Search Report issued in European Appln. No. 20196376.6 dated Jan. 15, 2021.
Preliminary Amendment filed in U.S. Appl. No. 17/140,522 dated Feb. 3, 2021.
Copending U.S. Appl. No. 17/140,522, filed Jan. 4, 2021 (a copy is not included because the cited application is not yet available to the public and the Examiner has ready access to the cited application).
Preliminary Amendment filed in copending U.S. Appl. No. 16/380,325 dated Sep. 30, 2019.
Notice of Allowance issued in copending U.S. Appl. No. 16/380,325 dated Oct. 5, 2020.

* cited by examiner

SYSTEMS AND METHODS FOR ACTIVATING TRANSDUCERS

CROSS-REFERENCE TO RELATED APPLICATIONS

This application is a continuation of U.S. patent application Ser. No. 15/581,364, filed Apr. 28, 2017, now U.S. Pat. No. 10,470,815, issued Nov. 12, 2019, which is a continuation of International Application No. PCT/US2014/066143, filed Nov. 18, 2014, the entire disclosure of both of these applications is hereby incorporated herein by reference.

TECHNICAL FIELD

Aspects of this disclosure generally are related to systems and methods for activating transducers, such systems and methods applicable to, among other things, medical systems.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature and tissue stimulation can also complicate the operation of the employed medical device.

In this regard, there is a need for intra-bodily-cavity transducer-based devices with improved performance and reduced complexity as compared to conventional devices.

In this regard, there is a need for improved activation of intra-bodily-cavity transducer-based devices that include numerous transducers.

In this regard, there is a need for the improved activation of intra-bodily cavity transducer-based devices including a plurality of transducer sets, the plurality of transducer sets activated concurrently or simultaneously to cause tissue ablation at multiple spaced-apart sites.

SUMMARY

At least the above-discussed need is addressed and technical solutions are achieved by various embodiments of the present invention. In some embodiments, device systems and methods executed by such systems exhibit enhanced capabilities for the activation of various transducers, which may be located within a bodily cavity, such as an intra-cardiac cavity. In some embodiments, the systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Treatment may include tissue ablation at multiple spaced-apart locations caused by concurrent activation of a plurality of transducer sets. Various ones of the transducers may be used to stimulate tissue within the bodily cavity. Stimulation can include pacing by way of non-limiting example. Other advantages will become apparent from the teaching herein to those of skill in the art.

In some embodiments, a transducer-activation system may be summarized as including a data processing device system, an input-output device system communicatively connected to the data processing device system, and a memory device system communicatively connected to the data processing device system and storing a program executable by the data processing device system, the program configured to cause the data processing device system to communicate, via the input-output device system, with an RF power source device system and a plurality of transducers located on a catheter device, the plurality of transducers arrangeable in a distribution in a bodily cavity.

The program may include reception instructions configured to cause reception, via the input-output device system, of a selection of at least some of the transducers in the distribution. The program may include identification instructions configured to identify a plurality of transducer sets from the selected at least some of the transducers in the distribution, the plurality of transducer sets including at least a first transducer set and a second transducer set, each of the transducer sets including at least one transducer of the selected at least some of the transducers in the distribution. The program may include first transmission instructions configured to cause a first transmission of power between the RF power source device system and each transducer in the first transducer set, the first transmission of power including an electrical property including at least one phase angle in a first range of phase angles, the electrical property being a current or a voltage. The program may include second transmission instructions configured to cause a second transmission of power between the RF power source device system and each transducer in the second transducer set, the second transmission of power including the electrical property including at least one phase angle in a second range of phase angles.

In some embodiments, the second range of phase angles does not overlap the first range of phase angles. In some embodiments each transducer included in the first transducer set and each transducer included in the second transducer set is operable to form a respective ablated tissue region in response to transmission of a respective one of the first transmission of power and the second transmission of power. In some embodiments, the first transmission of power and the second transmission of power may occur simultaneously at least in part over a time interval (a) during the reception of the selection, (b) after a completion of the reception of the selection, or both (a) and (b). In some embodiments, the identification instructions may be configured to at least prevent the first transducer set from including a particular transducer in the selected at least some of the transducers in the distribution that is sufficiently close to any respective transducer in the distribution included in the second transducer set to cause a confluence of respective ablated tissue regions therebetween if the first transmission of power was to be transmitted between the RF power source device system and the particular transducer simultaneously with the second transmission of power between the RF power source device system and the respective transducer included in the second transducer set. In some embodiments, no transmission of any power comprising the electrical property including at least one phase angle in the first range of phase angles between the RF power source device system and any of the plurality of transducers not included in the first transducer set occurs during the simultaneous occurrence of the first transmission of power and the second transmission of power, and no transmission of any power comprising the electrical property including at least one phase angle in the second range of phase angles between the RF power source device system and any of the plurality of transducers not included in the second transducer set occurs during the simultaneous occurrence of the first transmission of power and the second transmission of power. In some embodiments, the first transmission of power is delivered only between the RF power source device system and each transducer in the first transducer set during the simultaneous occurrence of the first transmission of power and the second transmission of power, and the second transmission of power is delivered only between the RF power source device system and each transducer in the second transducer set during the simultaneous occurrence of the first transmission of power and the second transmission of power.

In some embodiments, the electrical property of the first transmission of power transmitted between the RF power source device system and at least a first transducer in the first transducer set may include a first particular phase angle of the at least one phase angle in the first range of phase angles, and the electrical property of the second transmission of power transmitted between the RF power source device system and at least a second transducer in the second transducer set may include a second particular phase angle of the at least one phase angle in the second range of phase angles, a phase difference between the first particular phase angle and the second particular phase angle being 180 degrees. In some embodiments, the electrical property of the first transmission of power transmitted between the RF power source device system and at least a first transducer in the first transducer set may include a first particular phase angle of the at least one phase angle in the first range of phase angles, and the electrical property of the second transmission of power transmitted between the RF power source device system and at least a second transducer in the second transducer set may include a second particular phase angle of the at least one phase angle in the second range of phase angles, a phase difference between the first particular phase angle and the second particular phase angle being between 10 degrees and 180 degrees.

In some embodiments, the identification instructions may be configured to identify each respective transducer in each of the first transducer set and the second transducer set as a particular one of the selected at least some of the transducers in the distribution, the identified particular ones of the selected at least some of the transducers arranged in the distribution to prevent a confluence of an ablated tissue region formed by any transducer included in the first transducer set and an ablated tissue region formed by any transducer included in the second transducer set from forming during the simultaneous occurrence of the first transmission of power and the second transmission of power.

In some embodiments, for each respective transducer included in the second transducer set, the particular transducer in the selected at least some of the transducers in the distribution is a particular respective distance from the respective transducer included in the second transducer set, and the identification instructions may be configured to at least prevent the first transducer set from including the particular transducer, if it is determined according to the identification instructions that a confluence of an ablated tissue region formed by the particular transducer and an ablated tissue region formed by the respective transducer included in the second transducer set would, if the first transmission of power was to be transmitted between the RF power source device system and the particular transducer simultaneously with the second transmission of power between the RF power source and the respective transducer included in the second transducer set, occur due at least to the particular respective distance and a particular phase difference, the particular phase difference being between (1) a first particular phase angle of the at least one phase angle in the first range of phase angles that would be transmitted according to the first transmission of power between the RF power source device system and the particular transducer if the particular transducer was included in the first transducer set, and (2) a second particular phase angle of the at least one phase angle in the second range of phase angles to be transmitted according to the second transmission of power between the RF power source device system and the respective transducer included in the second transducer set.

In some embodiments, the first transducer set includes a first transducer of the selected at least some of the transducers in the distribution and another transducer of the selected at least some of the transducers in the distribution. The first transducer included in the first transducer set may be positioned in the distribution sufficiently close to the another transducer included in the first transducer set to cause a confluence of ablated tissue regions formed by the first transducer included in the first transducer set and the another transducer included in the first transducer set during a simultaneous occurrence of the first transmission of power between the RF power source device system and each of the first transducer included in the first transducer set and the another transducer included in the first transducer set. In some embodiments, the electrical property of the first transmission of power transmitted between the RF power source device system and the first transducer included in the first transducer set may have or may include a first phase angle of the at least one phase angle in the first range of phase angles. The electrical property of the first transmission of power transmitted between the RF power source device system and the another transducer included in the first transducer set may have or may include a second phase angle of the at least one phase angle in the first range of phase angles. In some embodiments, the second phase angle is different than the first phase angle. A phase difference between the second phase angle and the first phase angle may not exceed 10 degrees in some embodiments.

In some embodiments, the first transducer set includes a first transducer of the selected at least some of the transducers in the distribution and another transducer of the selected at least some of the transducers in the distribution. The first transducer included in the first transducer set may be positioned in the distribution sufficiently close to the another transducer included in the first transducer set to cause a confluence of ablated tissue regions formed by the first transducer included in the first transducer set and the another transducer included in the first transducer set during a simultaneous occurrence of the first transmission of power between the RF power source device system and each of the first transducer included in the first transducer set and the another transducer included in the first transducer set. In some embodiments, during the simultaneous occurrence of the first transmission of power between the RF power source device system and each of the first transducer included in the first transducer set and the another transducer included in the first transducer set, at least a difference between respective electrical potentials of the first transducer and the another transducer may cause relatively higher current to be transmitted between either the first transducer or the another transducer and a set of one or more transducers not including any transducer in the first transducer set than relatively lower current caused to be transmitted between the first transducer and the another transducer. In some embodiments, the electrical property of the first transmission of power transmitted between the RF power source device system and the first transducer included in the first transducer set may include a first phase angle of the at least one phase angle in the first range of phase angles, the electrical property of the first transmission of power transmitted between the RF power source device system and the another transducer included in the first transducer set may include a second phase angle of the at least one phase angle in the first range of phase angles, and the difference between the respective electric potentials of the first transducer and the another transducer may be dependent on, at least in part, a phase difference between the first phase angle and the second phase angle. In some embodiments, the set of one or more transducers not including any transducer in the first transducer set may include an indifferent electrode positioned outside of the bodily cavity. In some embodiments, the set of one or more transducers not including any transducer in the first transducer set may not or does not include any transducer included in the second transducer set. In some embodiments, the set of one or more transducers not including any transducer in the first transducer set may include at least one transducer that does not include any transducer included in the second transducer set. In some embodiments, the set of one or more transducers not including any transducer in the first transducer set may include at least one transducer included in the second transducer set. In some embodiments, the set of one or more transducers not including any transducer in the first transducer set may include at least one transducer of the plurality of transducers other than each transducer included in the first transducer set and other than each transducer included in the second transducer set.

In some embodiments, the first transducer set may include a first transducer of the selected at least some of the transducers in the distribution and another transducer of the selected at least some of the transducers in the distribution. The first transducer included in the first transducer set may be positioned in the distribution sufficiently distant from the another transducer included in the first transducer set to avoid causing a confluence of ablated tissue regions formed by the first transducer included in the first transducer set and the another transducer included in the first transducer set during a simultaneous occurrence of the first transmission of power between the RF power source device system and each of the first transducer included in the first transducer set and the another transducer included in the first transducer set. In some embodiments, the electrical property of the first transmission of power transmitted between the RF power source device system and the first transducer included in the first transducer set may include a first phase angle of the at least one phase angle in the first range of phase angles, and the electrical property of the first transmission of power transmitted between the RF power source device system and the another transducer included in the first transducer set may include a second phase angle of the at least one phase angle in the first range of phase angles. In some embodiments, second phase angle may be different than the first phase angle. A phase difference between the second phase angle and the first phase angle may not exceed 10 degrees in some embodiments or 20 degrees in some embodiments.

In some embodiments, the first transducer set may include at least three transducers of the selected at least some of the transducers in the distribution. In some embodiments, at least a first one of the at least three transducers included in the first transducer set may be positioned in the distribution sufficiently close to a second one of the at least three transducers included in the first transducer set to cause a confluence of ablated tissue regions formed by the first one of the at least three transducers included in the first transducer set and the second one of the at least three transducers included in the first transducer set during a simultaneous occurrence of the first transmission of power between the RF power source device system and each transducer included in the first transducer set. In some embodiments, at least the first one of the at least three transducers included in the first transducer set may be positioned in the distribution sufficiently distant from a third one of the at least three transducers included in the first transducer set to avoid causing a confluence of ablated tissue regions formed by the first one of the at least three transducers included in the first transducer set and the third one of the at least three transducers included in the first transducer set during the simultaneous occurrence of the first transmission of power between the RF power source device system and each transducer included in the first transducer set. In some embodiments, the second one of the at least three transducers included in the first transducer set may be positioned in the distribution sufficiently distant from the third one of the at least three transducers included in the first transducer set to avoid causing a confluence of ablated tissue regions formed by the second one of the at least three transducers included in the first transducer set and the third one of the at least three transducers included in the first transducer set during the simultaneous occurrence of the first transmission of power between the RF power source device system and each transducer included in the first transducer set. In some embodiments, the electrical property of the first transmission of power transmitted between the RF power source device system and each of the at least three transducers included in the first transducer set may include a same phase angle of the at least one phase angle in the first range of phase angles. In some embodiments, the electrical property of the first transmission of power transmitted between the RF power source device system and each of the first one and the second one of the at least three transducers included in the first transducer set during the simultaneous occurrence of the first transmission of power between the RF power source device system and each transducer included in the first transducer set may include a same phase angle of the at least one phase angle in the first range of phase angles. In some embodiments, the electrical property of the first transmission of power transmitted between the RF power source device system and the third one of the at least three transducers included in the first transducer set during the simultaneous occurrence of the first transmission of power between the RF power source device system and each transducer included in the first transducer set may include a phase angle of the at least one phase angle in the first range of phase angles different than the same phase angle of the at least one phase angle in the first range of phase angles.

In some embodiments, (1) the at least one phase angle in the first range of phase angles includes at least two phase angles; (2) the at least one phase angle in the second range of phase angles includes at least two phase angles; or both (1) and (2). In some embodiments, (1) the first transducer set includes a first transducer of the selected at least some of the transducers in the distribution and another transducer of the selected at least some of the transducers in the distribution, the electrical property of the first transmission of power transmitted between the RF power source device system and the first transducer included in the first transducer set includes a first phase angle of the at least one phase angle in the first range of phase angles, and the electrical property of the first transmission of power transmitted between the RF power source device system and the another transducer included in the first transducer set includes another phase angle of the at least one phase angle in the first range of phase angles different than the first phase angle; (2) the second transducer set includes a second transducer of the selected at least some of the transducers in the distribution and another transducer of the selected at least some of the transducers in the distribution, the electrical property of the second transmission of power transmitted between the RF power source device system and the second transducer included in the second transducer set includes a second phase angle of the at least one phase angle in the second range of phase angles, and the electrical property of the second transmission of power transmitted between the RF power source device system and the another transducer included in the second transducer set includes another phase angle of the at least one phase angle in the second range of phase angles different than the second phase angle; or both (1) and (2).

In some embodiments, (1) the electrical property of the first transmission of power between the RF power source device system and a first transducer included in the first transducer set includes a first portion including a first phase angle of the at least one phase angle in the first range of phase angles and a second portion including a second phase angle of the at least one phase angle in the first range of phase angles different than the first phase angle in the first range of phase angles; (2) the electrical property of the second transmission of power between the RF power source device system and a second transducer included in the second transducer set includes a first portion including a first phase angle of the at least one phase angle in the second range of phase angles and a second portion including a second phase angle of the at least one phase angle in the second range of phase angles different than the first phase angle in the second range of phase angles; or both (1) and (2).

In some embodiments, (1) the first transmission instructions may be configured to cause the electrical property of the first transmission of power between the RF power source device system and each of at least a first transducer included in the first transducer set to modulate between a first phase angle of the at least one phase angle in the first range of phase angles and a second phase angle of the at least one phase angle in the first range of phase angles different than the first phase angle in the first range of phase angles; (2) the second transmission instructions may be configured to cause the electrical property of the second transmission of power between the RF power source device system and each of at least a second transducer included in the second transducer set to modulate between a first phase angle of the at least one phase angle in the second range of phase angles and a second phase angle of the at least one phase angle in the second range of phase angles different than the first phase angle in the second range of phase angles; or both (1) and (2).

In some embodiments, the selected at least some of the transducers in the distribution may include some but not all of the transducers in the distribution.

In some embodiments, the input-output device system may include the plurality of transducers, and the distribution may be an arrayed distribution including a plurality of intersecting rows and columns, a respective group of the transducers arranged along each of the rows and a respective group of the transducers arranged along each of the columns. In some embodiments, the identification instructions may be configured to at least prevent the first transducer set from including any transducer in the selected at least some of the transducers in the distribution that is positioned along any of the rows or columns adjacent any transducer in the distribution included in the second transducer set.

In some embodiments, the input-output device system may include the plurality of transducers, and the transducers in the distribution are arranged in a grid including at least three rows and at least three columns, each of the columns arranged to intersect each of the rows at a respective intersection location, a respective one of the transducers arranged at each respective intersection location. The identification instructions may be configured to at least prevent the first transducer set from including any transducer in the selected at least some of the transducers in the distribution whose respective intersection location is adjacent to the respective intersection location of any transducer in the distribution included in the second transducer set.

In some embodiments, the program may further include display instructions configured to cause the input-output device system to concurrently display at least a map depicting a surface of a tissue wall of the bodily cavity, the surface interrupted by one or more openings (or ports), and a plurality of transducer graphical elements, each of the transducer graphical elements corresponding to at least part of a respective one of the plurality of transducers, a first spatial relationship between the displayed transducer graphical elements consistent with a second spatial relationship between the transducers. In some embodiments, the display instructions may be configured to display the respective transducer graphical elements corresponding to the selected at least some of the transducers in the distribution surrounding at least one of the one or more openings (or ports) depicted in the map. In some embodiments, the program may further include information reception instructions configured to cause reception via the input-output device system of information from each of the plurality of transducers. In some embodiments, the display instructions may be configured to display the map based at least on the information received from the each of the plurality of transducers. In some embodiments, the display instructions may be further configured to display the respective transducer graphical elements corresponding to the selected at least some of the transducers in the distribution differently than the transducers graphical elements corresponding to particular ones of the plurality of transducers that do not form part of the selected at least some of the transducers in the distribution. In some embodiments, the reception, via the input-output device system, of the selected at least some of the transducers in the distribution may include reception of a user-based selection, via the input-output device system, of the selected at least some of the transducers in the distribution.

In some embodiments, the reception, via the input-output device system, of the selected at least some of the transducers in the distribution may include reception of a user-based selection, via the input-output device system, of the selected at least some of the transducers in the distribution, and the identification instructions configured to identify the plurality of transducer sets from the selected at least some of the transducers in the distribution may include machine-based identification of the plurality of transducer sets from the selected at least some of the transducers in the distribution.

In some embodiments, the identification instructions may be configured to cause the first transducer set to include only transducers in the selected at least some of the transducers in the distribution that each are sufficiently distant from each respective transducer in the distribution included in the second transducer set to not cause a confluence of ablated tissue regions formed by any transducer in the first transducer set and any transducer in the second transducer set during the simultaneous occurrence of the first transmission of power and the second transmission of power. In some embodiments, (1) the first transducer set may include two or more of the transducers of the selected at least some of the transducers in the distribution, and the first transmission of power between the RF power source device system and each transducer included in the first transducer set is transmitted simultaneously between the RF power source device system and each transducer included in the first transducer set; (2) the second transducer set may include two or more of the transducers of the selected at least some of the transducers in the distribution, and the second transmission of power between the RF power source device system and each transducer included in the second transducer set is transmitted simultaneously between the RF power source device system and each transducer included in the second transducer set; or both (1) and (2).

In some embodiments, a transducer-activation system may be summarized as including a data processing device system; an input-output device system communicatively connected to the data processing device system; and a memory device system communicatively connected to the data processing device system and storing a program executable by the data processing device system. The data processing device system may be configured by the program at least to: communicate, via the input-output device system, with an RF power source device system and a plurality of transducers located on a catheter device, the plurality of transducers arrangeable in a distribution in a bodily cavity; receive, via the input-output device system, a selection of at least some of the transducers in the distribution; identify a plurality of transducer sets from the selected at least some of the transducers in the distribution, the plurality of transducer sets including at least a first transducer set and a second transducer set, each of the transducer sets including at least one transducer of the selected at least some of the transducers in the distribution; cause a first transmission of power between the RF power source device system and each transducer in the first transducer set, the first transmission of power comprising an electrical property including at least one phase angle in a first range of phase angles, the electrical property being a current or a voltage; and cause a second transmission of power between the RF power source device system and each transducer in the second transducer set, the second transmission of power comprising the electrical property including at least one phase angle in a second range of phase angles. In some embodiments, the second range of phase angles does not overlap the first range of phase angles. Each transducer included in the first transducer set and each transducer included in the second transducer set may be operable to form a respective ablated tissue region in response to transmission of a respective one of the first transmission of power and the second transmission of power. The first transmission of power and the second transmission of power may occur simultaneously at least in part over a time interval (a) during the reception of the selection, (b) after a completion of the reception of the selection, or both (a) and (b). In some embodiments, the identifying of the plurality of transducer sets at least prevents the first transducer set from including a particular transducer in the selected at least some of the transducers in the distribution that is sufficiently close to any respective transducer in the distribution included in the second transducer set to cause a confluence of respective ablated tissue regions therebetween if the first transmission of power was to be transmitted between the RF power source device system and the particular transducer simultaneously with the second transmission of power between the RF power source device system and the respective transducer included in the second transducer set. In some embodiments, no transmission of any power comprising the electrical property including at least one phase angle in the first range of phase angles between the RF power source device system and any of the plurality of transducers not included in the first transducer set occurs during the simultaneous occurrence of the first transmission of power and the second transmission of power, and no transmission of any power comprising the electrical property including at least one phase angle in the second range of phase angles between the RF power source device system and any of the plurality of transducers not included in the second transducer set occurs during the simultaneous occurrence of the first transmission of power and the second transmission of power. In some embodiments, the first transmission of power is delivered only between the RF power source device system and each transducer in the first transducer set during the simultaneous occurrence of the first transmission of power and the second transmission of power, and the second transmission of power is delivered only between the RF power source device system and each transducer in the second transducer set during the simultaneous occurrence of the first transmission of power and the second transmission of power.

In some embodiments, a transducer-activation method may be executed by a data processing device system according to a program stored by a memory device system communicatively connected to the data processing device system. The data processing device system may be further communicatively connected to an input-output device system. The method may include communicating, via the input-output device system, with an RF power source device system and a plurality of transducers located on a catheter device, the plurality of transducers arrangeable in a distribution in a bodily cavity; receiving, via the input-output device system, a selection of at least some of the transducers in the distribution; identifying a plurality of transducer sets from the selected at least some of the transducers in the distribution, the plurality of transducer sets including at least a first transducer set and a second transducer set, each of the transducer sets including at least one transducer of the selected at least some of the transducers in the distribution; causing a first transmission of power between the RF power source device system and each transducer in the first transducer set, the first transmission of power comprising an electrical property including at least one phase angle in a first range of phase angles, the electrical property being a current or a voltage; and causing a second transmission of power between the RF power source device system and each transducer in the second transducer set, the second transmission of power comprising the electrical property including at least one phase angle in a second range of phase angles. In some embodiments, the second range of phase angles does not overlap the first range of phase angles. Each transducer included in the first transducer set and each transducer included in the second transducer set may be operable to form a respective ablated tissue region in response to transmission of a respective one of the first transmission of power and the second transmission of power. The first transmission of power and the second transmission of power may occur simultaneously at least in part over a time interval (a) during the reception of the selection, (b) after a completion of the reception of the selection, or both (a) and (b). In some embodiments, the identifying of the plurality of transducer sets at least prevents the first transducer set from including a particular transducer in the selected at least some of the transducers in the distribution that is sufficiently close to any respective transducer in the distribution included in the second transducer set to cause a confluence of respective ablated tissue regions therebetween if the first transmission of power was to be transmitted between the RF power source device system and the particular transducer simultaneously with the second transmission of power between the RF power source device system and the respective transducer included in the second transducer set.

In some embodiments, a computer-readable storage medium system may include one or more computer-readable storage mediums storing a program executable by one or more data processing devices of a data processing device system communicatively connected to an input-output device system. The program may be configured to cause the data processing device system to communicate, via the input-output device system, with an RF power source device system and a plurality of transducers located on a catheter device, the plurality of transducers arrangeable in a distribution in a bodily cavity. The program may include a reception module configured to cause reception, via the input-output device system, of a selection of at least some of the transducers in the distribution; an identification module configured to identify a plurality of transducer sets from the selected at least some of the transducers in the distribution, the plurality of transducer sets including at least a first transducer set and a second transducer set, each of the transducer sets including at least one transducer of the selected at least some of the transducers in the distribution; a first transmission module configured to cause a first transmission of power between the RF power source device system and each transducer in the first transducer set, the first transmission of power comprising an electrical property including at least one phase angle in a first range of phase angles, the electrical property being a current or a voltage; and a second transmission module configured to cause a second transmission of power between the RF power source device system and each transducer in the second transducer set, the second transmission of power comprising the electrical property including at least one phase angle in a second range of phase angles. In some embodiments, the second range of phase angles does not overlap the first range of phase angles. Each transducer included in the first transducer set and each transducer included in the second transducer set may be operable to form a respective ablated tissue region in response to transmission of a respective one of the first transmission of power and the second transmission of power. The first transmission of power and the second transmission of power may occur simultaneously at least in part over a time interval (a) during the reception of the selection, (b) after a completion of the reception of the selection, or both (a) and (b). The identification module may be configured to at least prevent the first transducer set from including a particular transducer in the selected at least some of the transducers in the distribution that is sufficiently close to any respective transducer in the distribution included in the second transducer set to cause a confluence of respective ablated tissue regions therebetween if the first transmission of power was to be transmitted between the RF power source device system and the particular transducer simultaneously with the second transmission of power between the RF power source device system and the respective transducer included in the second transducer set.

In some embodiments, a transducer-activation system may be summarized as including a data processing device system, an input-output device system communicatively connected to the data processing device system, and a memory device system communicatively connected to the data processing device system and storing a program executable by the data processing device system, the program configured to cause the data processing device system to communicate, via the input-output device system, with an RF power source device system and a plurality of transducers located on a catheter device, the plurality of transducers arrangeable in a distribution in a bodily cavity.

The program may include reception instructions configured to cause reception, via the input-output device system, of a selection of at least some of the transducers in the distribution. The program may include identification instructions configured to identify a plurality of transducer sets from the selected at least some of the transducers in the distribution, the plurality of transducer sets including at least a first transducer set and a second transducer set, each of the first transducer set and the second transducer set respectively including two or more of the selected at least some of the transducers in the distribution. The program may include first transmission instructions configured to cause simultaneous transmission of a first transmission of power between the RF power source device system and each respective one of the transducers in the first transducer set, the first transmission of power between the RF power source device system and each respective one of the transducers including an electrical property including a respective phase angle in a first range of phase angles, the electrical property being a current or a voltage. The program may include second transmission instructions configured to cause simultaneous transmission of a second transmission of power between the RF power source device system and each respective one of the transducers in the second transducer set, the second transmission of power between the RF power source device system and each respective one of the transducers including the electrical property including a respective phase angle in a second range of phase angles, the second range of phase angles not overlapping the first range of phase angles.

Each transducer included in the first transducer set and each transducer included in the second transducer set may be operable to form a respective ablated tissue region in response to transmission of a respective one of the first transmission of power and the second transmission of power. Each of the first transmission of power and the second transmission of power may occur simultaneously at least in part over a time interval (a) during the reception of the selection, (b) after a completion of the reception of the selection, or both (a) and (b).

In some embodiments, the identification instructions may be configured to identify each of the first transducer set and the second transducer set such that during the simultaneous transmission of the first transmission of power between the RF power source device system and each respective one of the transducers included in the first transducer set, at least a difference between respective electrical potentials of any two of the transducers included in the first transducer set causes relatively higher current to be transmitted between either of the any two transducers included in the first transducer set and a first set of one or more transducers not including any transducer in the first transducer set than relatively lower current caused to be transmitted between the transducers of the any two of the transducers included in the first transducer set.

In some embodiments, the identification instructions may be configured to identify each of the first transducer set and the second transducer set such that during the simultaneous transmission of the second transmission of power between the RF power source device system and each respective one of the transducers included in the second transducer set, at least a difference between respective electrical potentials of any two of the transducers included in the second transducer set causes relatively higher current to be transmitted between either of the any two transducers included in the second transducer set and a second set of one or more transducers not including any transducer in the second transducer set than relatively lower current caused to be transmitted between the transducers of the any two of the transducers included in the second transducer set.

In some embodiments, the identification instructions may be configured to identify each of the first transducer set and the second transducer set such that a particular distance between any particular transducer included in the first transducer set and any particular transducer included in the second transducer set is sufficient to avoid a confluence of ablated tissue regions formed by the particular transducer included in the first transducer set and the particular transducer included in the second transducer set during the simultaneous occurrence of the first transmission of power and the second transmission of power.

In some embodiments, no transmission of any power comprising the electrical property including at least one phase angle in the first range of phase angles between the RF power source device system and any of the plurality of transducers not included in the first transducer set occurs during the simultaneous occurrence of the first transmission of power and the second transmission of power, and no transmission of any power comprising the electrical property including at least one phase angle in the second range of phase angles between the RF power source device system and any of the plurality of transducers not included in the second transducer set occurs during the simultaneous occurrence of the first transmission of power and the second transmission of power. In some embodiments, the first transmission of power is delivered only between the RF power source device system and each transducer in the first transducer set during the simultaneous occurrence of the first transmission of power and the second transmission of power, and the second transmission of power is delivered only between the RF power source device system and each transducer in the second transducer set during the simultaneous occurrence of the first transmission of power and the second transmission of power.

In some embodiments, the electrical property of the first transmission of power transmitted between the RF power source device system and a first of the any two of the transducers included in the first transducer set may include a first phase angle of the at least one phase angle in the first range of phase angles and the electrical property of the first transmission of power transmitted between the RF power source device system and a second of the any two of the transducers included in the first transducer set may include a second phase angle of the at least one phase angle in the first range of phase angles. In some embodiments, the difference between the respective electric potentials of the any two of the transducers included in the first transducer set may be dependent on, at least in part, a phase difference between the first phase angle and the second phase angle. In some embodiments the electrical property of the second transmission of power transmitted between the RF power source device system and a first of the any two of the transducers included in the second transducer set may include a third phase angle of the at least one phase angle in the second range of phase angles, and the electrical property of the second transmission of power transmitted between the RF power source device system and a second of the any two of the transducers included in the second transducer set may include a fourth phase angle of the at least one phase angle in the second range of phase angles. In some embodiments, the difference between the respective electric potentials of the any two of the transducers included in the second transducer set may be dependent on, at least in part, a phase difference between the third phase angle and the fourth phase angle.

In some embodiments, each transducer included in the first transducer set may be different than each transducer included in the second transducer set.

In some embodiments, (1) a first transducer included in the first transducer set is positioned in the distribution sufficiently close to another transducer included in the first transducer set to cause a confluence of ablated tissue regions formed by the first transducer included in the first transducer set and the another transducer included in the first transducer set during the simultaneous transmission of the first transmission of power between the RF power source device system and each respective one of the transducers included in the first transducer set; (2) a second transducer included in the second transducer set is positioned in the distribution sufficiently close to another transducer included in the second transducer set to cause a confluence of ablated tissue regions formed by the second transducer included in the second transducer set and the another transducer included in the second transducer set during the simultaneous transmission of the second transmission of power between the RF power source device system and each respective one of the transducers included in the second transducer set; or both (1) and (2).

In some embodiments, a first one of the transducers included in the first transducer set is positioned in the distribution sufficiently close to a second one of the transducers included in the first transducer set to cause a confluence of ablated tissue regions formed by the first one of the transducers included in the first transducer set and the second one of the transducers included in the first transducer set during the simultaneous transmission of the first transmission of power between the RF power source device system and each respective one of the transducers included in the first transducer set. In some embodiments, the first one of the transducers included in the first transducer set may be positioned in the distribution sufficiently distant from a third one of the transducers included in the first transducer set to avoid causing a confluence of ablated tissue regions formed by the first one of the transducers included in the first transducer set and the third one of the transducers included in the first transducer set during the simultaneous transmission of the first transmission of power between the RF power source device system and each respective one of the transducers included in the first transducer set. In some embodiments, the second one of the transducers included in the first transducer set may be positioned in the distribution sufficiently distant from the third one of the transducers included in the first transducer set to avoid causing a confluence of the ablated tissue regions formed by the second one of the transducers included in the first transducer set and the third one of the transducers included in the first transducer set during the simultaneous transmission of the first transmission of power between the RF power source device system and each respective one of the transducers included in the first transducer set.

In some embodiments, the input-output device system includes the plurality of transducers, and the transducers in the distribution are arranged in a grid including at least three rows and at least three columns, each of the columns arranged to intersect each of the rows at a respective intersection location, a respective one of the transducers arranged at each respective intersection location. The identification instructions may be configured to at least prevent the first transducer set from including any transducer in the selected at least some of the transducers in the distribution whose respective intersection location is adjacent to the respective intersection location of any transducer in the distribution included in the second transducer set.

In some embodiments, a transducer-activation system may include a data processing device system; an input-output device system communicatively connected to the data processing device system; and a memory device system communicatively connected to the data processing device system and storing a program executable by the data processing device system. The data processing device system may be configured by the program at least to: communicate, via the input-output device system, with an RF power source device system and a plurality of transducers located on a catheter device, the plurality of transducers arrangeable in a distribution in a bodily cavity; receive, via the input-output device system, a selection of at least some of the transducers in the distribution; identify a plurality of transducer sets from the selected at least some of the transducers in the distribution, the plurality of transducer sets including at least a first transducer set and a second transducer set, each of the first transducer set and the second transducer set respectively including two or more of the selected at least some of the transducers in the distribution; cause simultaneous transmission of a first transmission of power between the RF power source device system and each respective one of the transducers in the first transducer set, the first transmission of power between the RF power source device system and each respective one of the transducers including an electrical property including a respective phase angle in a first range of phase angles, the electrical property being a current or a voltage; and cause simultaneous transmission of a second transmission of power between the RF power source device system and each respective one of the transducers in the second transducer set, the second transmission of power between the RF power source device system and each respective one of the transducers including the electrical property including a respective phase angle in a second range of phase angles, the second range of phase angles not overlapping the first range of phase angles. Each transducer included in the first transducer set and each transducer included in the second transducer set may be operable to form a respective ablated tissue region in response to transmission of a respective one of the first transmission of power and the second transmission of power. Each of the first transmission of power and the second transmission of power may occur simultaneously at least in part over a time interval (a) during the reception of the selection, (b) after a completion of the reception of the selection, or both (a) and (b). The identifying of the plurality of transducer sets may identify each of the first transducer set and the second transducer set such that at least: during the simultaneous transmission of the first transmission of power between the RF power source device system and each respective one of the transducers included in the first transducer set, at least a difference between respective electrical potentials of any two of the transducers included in the first transducer set causes relatively higher current to be transmitted between either of the any two transducers included in the first transducer set and a first set of one or more transducers not including any transducer in the first transducer set than relatively lower current caused to be transmitted between the transducers of the any two of the transducers included in the first transducer set; during the simultaneous transmission of the second transmission of power between the RF power source device system and each respective one of the transducers included in the second transducer set, at least a difference between respective electrical potentials of any two of the transducers included in the second transducer set causes relatively higher current to be transmitted between either of the any two transducers included in the second transducer set and a second set of one or more transducers not including any transducer in the second transducer set than relatively lower current caused to be transmitted between the transducers of the any two of the transducers included in the second transducer set; and a particular distance between any particular transducer included in the first transducer set and any particular transducer included in the second transducer set is sufficient to avoid a confluence of ablated tissue regions formed by the particular transducer included in the first transducer set and the particular transducer included in the second transducer set during the simultaneous occurrence of the first transmission of power and the second transmission of power. In some embodiments, no transmission of any power comprising the electrical property including at least one phase angle in the first range of phase angles between the RF power source device system and any of the plurality of transducers not included in the first transducer set occurs during the simultaneous occurrence of the first transmission of power and the second transmission of power, and no transmission of any power comprising the electrical property including at least one phase angle in the second range of phase angles between the RF power source device system and any of the plurality of transducers not included in the second transducer set occurs during the simultaneous occurrence of the first transmission of power and the second transmission of power. In some embodiments, the first transmission of power is delivered only between the RF power source device system and each transducer in the first transducer set during the simultaneous occurrence of the first transmission of power and the second transmission of power, and the second transmission of power is delivered only between the RF power source device system and each transducer in the second transducer set during the simultaneous occurrence of the first transmission of power and the second transmission of power.

In some embodiments, a transducer-activation method may be executed by a data processing device system according to a program stored by a memory device system communicatively connected to the data processing device system. The data processing device system may be further communicatively connected to an input-output device system. The method may include communicating, via the input-output device system, with an RF power source device system and a plurality of transducers located on a catheter device, the plurality of transducers arrangeable in a distribution in a bodily cavity; receiving, via the input-output device system, a selection of at least some of the transducers in the distribution; identifying a plurality of transducer sets from the selected at least some of the transducers in the distribution, the plurality of transducer sets including at least a first transducer set and a second transducer set, each of the first transducer set and the second transducer set respectively including two or more of the selected at least some of the transducers in the distribution; causing simultaneous transmission of a first transmission of power between the RF power source device system and each respective one of the transducers in the first transducer set, the first transmission of power between the RF power source device system and each respective one of the transducers comprising an electrical property including a respective phase angle in a first range of phase angles, the electrical property being a current or a voltage; and causing simultaneous transmission of a second transmission of power between the RF power source device system and each respective one of the transducers in the second transducer set, the second transmission of power between the RF power source device system and each respective one of the transducers comprising the electrical property including a respective phase angle in a second range of phase angles, the second range of phase angles not overlapping the first range of phase angles. Each transducer included in the first transducer set and each transducer included in the second transducer set may be operable to form a respective ablated tissue region in response to transmission of a respective one of the first transmission of power and the second transmission of power. Each of the first transmission of power and the second transmission of power may occur simultaneously at least in part over a time interval (a) during the reception of the selection, (b) after a completion of the reception of the selection, or both (a) and (b). The identifying of the plurality of transducer sets may identify each of the first transducer set and the second transducer set such that at least: during the simultaneous transmission of the first transmission of power between the RF power source device system and each respective one of the transducers included in the first transducer set, at least a difference between respective electrical potentials of any two of the transducers included in the first transducer set causes relatively higher current to be transmitted between either of the any two transducers included in the first transducer set and a first set of one or more transducers not including any transducer in the first transducer set than relatively lower current caused to be transmitted between the transducers of the any two of the transducers included in the first transducer set; during the simultaneous transmission of the second transmission of power between the RF power source device system and each respective one of the transducers included in the second transducer set, at least a difference between respective electrical potentials of any two of the transducers included in the second transducer set causes relatively higher current to be transmitted between either of the any two transducers included in the second transducer set and a second set of one or more transducers not including any transducer in the second transducer set than relatively lower current caused to be transmitted between the transducers of the any two of the transducers included in the second transducer set; and a particular distance between any particular transducer included in the first transducer set and any particular transducer included in the second transducer set is sufficient to avoid a confluence of ablated tissue regions formed by the particular transducer included in the first transducer set and the particular transducer included in the second transducer set during the simultaneous occurrence of the first transmission of power and the second transmission of power.

In some embodiments, a computer-readable storage medium system may include one or more computer-readable storage mediums storing a program executable by one or more data processing devices of a data processing device system communicatively connected to an input-output device system. The program may be configured to cause the data processing device system to communicate, via the input-output device system, with an RF power source device system and a plurality of transducers located on a catheter device, the plurality of transducers arrangeable in a distribution in a bodily cavity. The program may include: a reception module configured to cause reception, via the input-output device system, of a selection of at least some of the transducers in the distribution; an identification module configured to identify a plurality of transducer sets from the selected at least some of the transducers in the distribution, the plurality of transducer sets including at least a first transducer set and a second transducer set, each of the first transducer set and the second transducer set respectively including two or more of the selected at least some of the transducers in the distribution; a first transmission module configured to cause simultaneous transmission of a first transmission of power between the RF power source device system and each respective one of the transducers in the first transducer set, the first transmission of power between the RF power source device system and each respective one of the transducers including an electrical property including a respective phase angle in a first range of phase angles, the electrical property being a current or a voltage; and a second transmission module configured to cause simultaneous transmission of a second transmission of power between the RF power source device system and each respective one of the transducers in the second transducer set, the second transmission of power between the RF power source device system and each respective one of the transducers comprising the electrical property including a respective phase angle in a second range of phase angles, the second range of phase angles not overlapping the first range of phase angles. Each transducer included in the first transducer set and each transducer included in the second transducer set may be operable to form a respective ablated tissue region in response to transmission of a respective one of the first transmission of power and the second transmission of power. Each of the first transmission of power and the second transmission of power may occur simultaneously at least in part over a time interval (a) during the reception of the selection, (b) after a completion of the reception of the selection, or both (a) and (b). The identification module may be configured to identify each of the first transducer set and the second transducer set such that at least: during the simultaneous transmission of the first transmission of power between the RF power source device system and each respective one of the transducers included in the first transducer set, at least a difference between respective electrical potentials of any two of the transducers included in the first transducer set causes relatively higher current to be transmitted between either of the any two transducers included in the first transducer set and a first set of one or more transducers not including any transducer in the first transducer set than relatively lower current caused to be transmitted between the transducers of the any two of the transducers included in the first transducer set; during the simultaneous transmission of the second transmission of power between the RF power source device system and each respective one of the transducers included in the second transducer set, at least a difference between respective electrical potentials of any two of the transducers included in the second transducer set causes relatively higher current to be transmitted between either of the any two transducers included in the second transducer set and a second set of one or more transducers not including any transducer in the second transducer set than relatively lower current caused to be transmitted between the transducers of the any two of the transducers included in the second transducer set; and a particular distance between any particular transducer included in the first transducer set and any particular transducer included in the second transducer set is sufficient to avoid a confluence of ablated tissue regions formed by the particular transducer included in the first transducer set and the particular transducer included in the second transducer set during the simultaneous occurrence of the first transmission of power and the second transmission of power.

Various systems may include combinations and subsets of all the systems summarized above or otherwise described herein.

Any of the features of any of the methods discussed herein may be combined with any of the other features of any of the methods discussed herein. In addition, a computer program product may be provided that includes program code portions for performing some or all of any of the methods and associated features thereof described herein, when the computer program product is executed by a computer or other computing device or device system. Such a computer program product may be stored on one or more computer-readable storage mediums.

In some embodiments, each of any or all of the computer-readable storage mediums or medium systems described herein is a non-transitory computer-readable storage medium or medium system including one or more non-transitory computer-readable storage mediums storing the respective program(s).

Further, any or all of the methods and associated features thereof discussed herein may be implemented by all or part of a device system or apparatus, such as any of those described herein.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
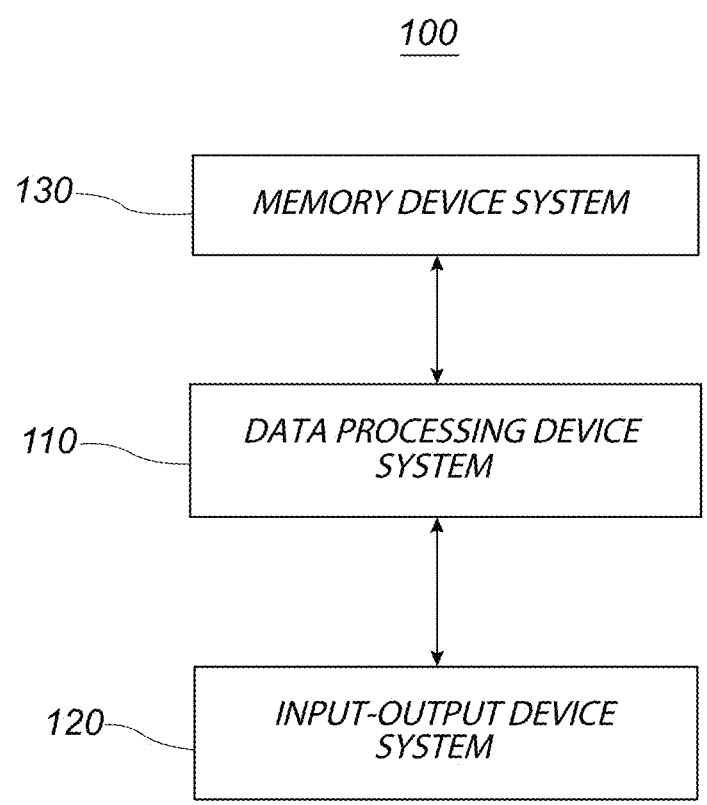
FIG. 1 includes a schematic representation of a transducer-activation system according to various example embodiments, the transducer-activation system including a data processing device system, an input-output device system, and a memory device system.

In the following description, certain specific details are set forth in order to provide a thorough understanding of various embodiments of the invention. However, one skilled in the art will understand that the invention may be practiced at a more general level without these details. In other instances, well-known structures have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily all referring to one embodiment or a same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements than those present in the subset's parent or superset. In addition, the word "number" is intended to mean one or more. For example, the phrase "a number of elements" would exclude there being zero elements.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase "activation of at least transducer A" includes activation of transducer A by itself, as well as activation of transducer A and activation of one or more other additional elements besides transducer A. In the same manner, the phrase "activation of transducer A" includes activation of transducer A by itself, as well as activation of transducer A and activation of one or more other additional elements besides transducer A. However, the phrase "activation of only transducer A" includes only activation of transducer A, and excludes activation of any other transducers besides transducer A.

The word "ablation" as used in this disclosure should be understood to include any disruption to certain properties of tissue. Most commonly, the disruption is to the electrical conductivity and is achieved by heating, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that may include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity of a heart). A bodily cavity is sometimes referred to as a "bodily chamber" in some embodiments.

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue may refer to a tissue having fluidic properties (e.g., blood) and may be referred to as fluidic tissue.

The term "transducer" as used in this disclosure should be interpreted broadly as any device capable of distinguishing between fluid (e.g., fluidic tissue) and tissue, sensing temperature, creating heat, ablating tissue, sensing, sampling or measuring electrical activity of a tissue surface (e.g., sensing, sampling or measuring intra-cardiac electrograms, or sensing, sampling or measuring intra-cardiac voltage data), stimulating tissue, or any combination thereof. A transducer can convert input energy of one form into output energy of another form. Without limitation, a transducer may include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions may include, but are not limited to, tissue ablation, sensing, sampling or measuring electrophysiological activity (e.g., sensing, sampling or measuring intra-cardiac electrogram information or sensing, sampling or measuring intra-cardiac voltage data), sensing, sampling or measuring temperature and sensing, sampling or measuring electrical characteristics (e.g., tissue impedance or tissue conductivity). For example, in some embodiments, activation of a tissue ablation function of a particular transducer is initiated by causing energy sufficient for tissue ablation from a power source device system to be delivered to the particular transducer. Alternatively, in this example, the activation may be deemed to be initiated when the particular transducer causes a temperature sufficient for the tissue ablation due to the energy provided by the power source device system. Also in this example, the activation may last for a duration of time concluding when the ablation function is no longer active, such as when energy sufficient for the tissue ablation is no longer provided to the particular transducer. Alternatively, in this example, the activation period may be deemed to be concluded when the temperature caused by the particular transducer is below the temperature sufficient for the tissue ablation. In some contexts, however, the word "activation" may merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such a controller system or data processing device system, in order to cause the system to perform one or more operations. The set of instructions or modules can be stored by any kind of memory device, such as those described subsequently with respect to the memory device system 130 or 330 shown in FIGS. 1 and 3, respectively. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" may be defined as a set of instructions. In some instances, this disclosure describes that the instructions or modules of a program perform a function. Such descriptions should be deemed to be equivalent to describing that the instructions or modules are configured to cause the performance of the function.

Unless otherwise required by context, each of the phrases "derived from" or "derivation of" or "derivation thereof" or the like is intended to mean to come from at least some part of a source, be created from at least some part of a source, or be developed as a result of a process in which at least some part of a source forms an input. For example, a data set derived from some particular portion of data may include at least some part of the particular portion of data, or may be created from at least part of the particular portion of data, or may be developed in response to a data manipulation process in which at least part of the particular portion of data forms an input. In some embodiments, a data set may be derived from a subset of the particular portion of data. In some embodiments, the particular portion of data is analyzed to identify a particular subset of the particular portion of data, and a data set is derived from the subset. In various ones of these embodiments, the subset may include some, but not all, of the particular portion of data. In some embodiments, changes in least one part of a particular portion of data may result in changes in a data set derived at least in part from the particular portion of data.

In this regard, each of the phrases "derived from" or "derivation of" or "derivation thereof" or the like is used herein at times merely to emphasize the possibility that such data or information may be modified or subject to one or more operations. For example, if a device generates first data for display, the process of converting the generated first data into a format capable of being displayed may alter the first data. This altered form of the first data may be considered a derivative or derivation of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative or derivation of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derived from" or "derivation of" or "derivation thereof" or the like is used in reference to the information or data. As indicated above, usage of the phrase "derived from" or "derivation of" or "derivation thereof" or the like merely emphasizes the possibility of such changes. Accordingly, the addition or deletion of the phrase "derived from" or "derivation of" or "derivation thereof" or the like should have no impact on the interpretation of the respective data or information. For example, the above-discussed color-coded bar chart may be considered a derivative of the respective first data or may be considered the respective first data itself.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, this disclosure sometimes refers to a "catheter device", but such catheter device may equivalently be referred to as a "catheter device system". The word "device" may equivalently be referred to as a "device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" commonly is used in this disclosure. For example, this phrase might be used in the following context, where an event A occurs in response to the occurrence of an event B. In this regard, such phrase may include, for example, that at least the occurrence of the event B causes or triggers the event A.

Further, the phrase "graphical representation" used herein is intended to include a visual representation presented via a display device and may include computer-generated text, graphics, animations, or one or more combinations thereof, which may include one or more visual representations originally generated, at least in part, by an image-capture device, such as fluoroscopy images, CT scan images, MRI images, etc.

Figure 6:
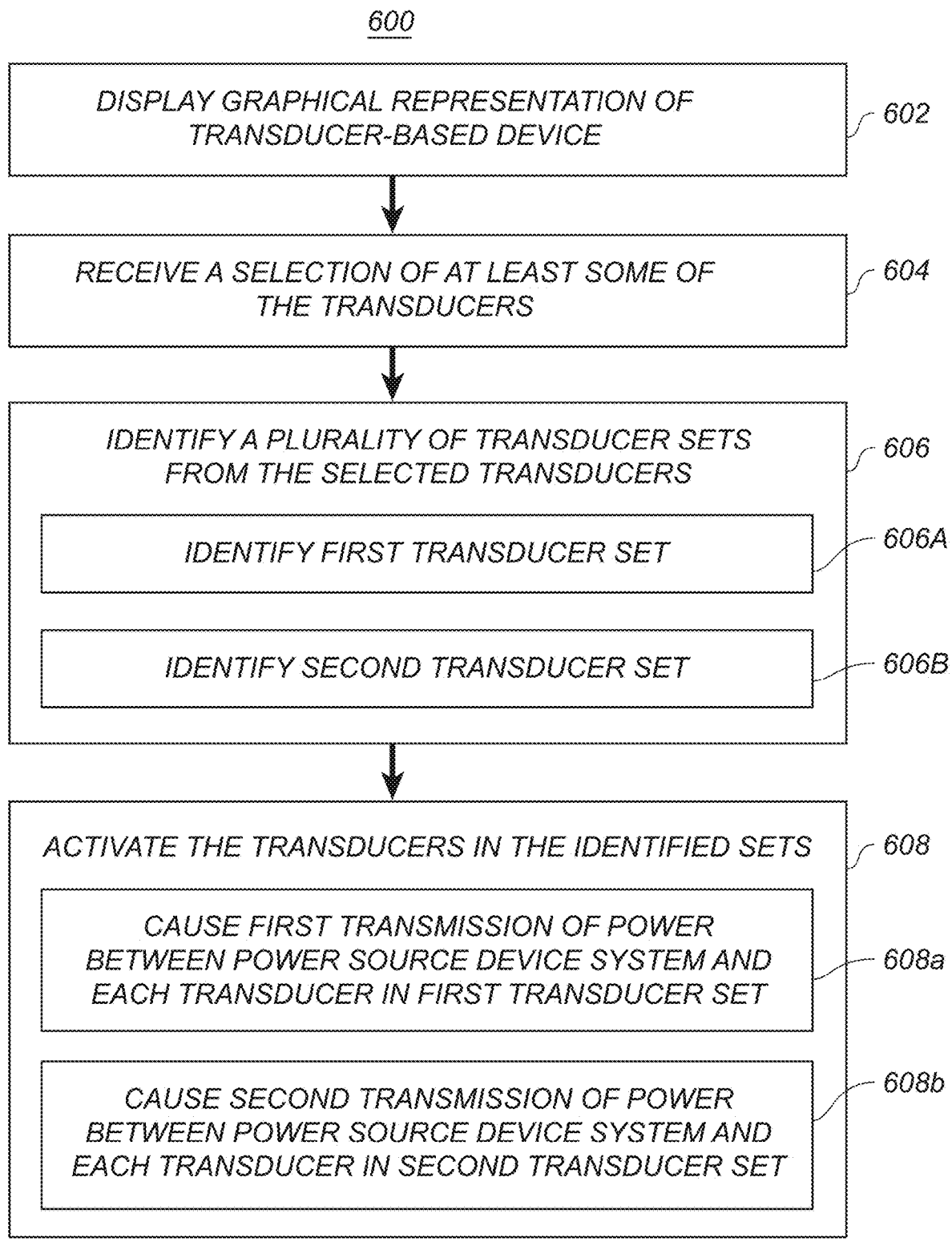
FIG. 6 includes a block diagram of a method for activating transducers of a transducer-based device according to various example embodiments.

Further still, example methods are described herein with respect to FIG. 6. Such figure is described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in each of the method figures herein is not limited to an actual structure of any program or set of instructions or required ordering of method tasks, and such method figures, according to some embodiments, merely illustrate the tasks that instructions are configured to perform, for example upon execution by a data processing device system in conjunction with interactions with one or more other devices or device systems.

FIG. 1 schematically illustrates a system 100 for activating transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, the methods of various embodiments, including the example methods of FIG. 6 described herein. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods of various embodiments, including the example methods of FIG. 6 described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 may be considered a non-transitory computer-readable storage medium system.

The phrase "communicatively connected" is intended to include any type of connection, whether wired or wireless, between devices, data processors, or programs between which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system may include a user-activatable control system that is responsive to a user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion a transducer-based device system. The phrase "transducer-based device system" is intended to include one or more physical systems that include various transducers. The phrase "transducer-based device" is intended to include one or more physical devices that include various transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments. In some embodiments, the input-output device system 120 may include one or more display devices that display one or more of the graphical interfaces of FIG. 5, described below.

Various embodiments of transducer-based devices are described herein. Some of the described devices are medical devices that are percutaneously or intravascularly deployed. Some of the described devices are moveable between a delivery or unexpanded configuration (e.g., FIG. 3A, discussed below) in which a portion of the device is sized for passage through a bodily opening leading to a bodily cavity, and an expanded or deployed configuration (e.g., FIG. 3B, discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics may allow a medical system to map the cavity, for example using positions of openings or ports into and out of the cavity to determine a position or orientation (e.g., pose), or both of the portion of the device in the bodily cavity. In some example embodiments, the devices are capable of sensing various cardiac functions (e.g., electrophysiological activity including intra-cardiac voltages). In some example embodiments, the devices are capable of providing stimulation (e.g., electrical stimulation) to tissue within the bodily cavity. Electrical stimulation may include pacing.

Figure 2:
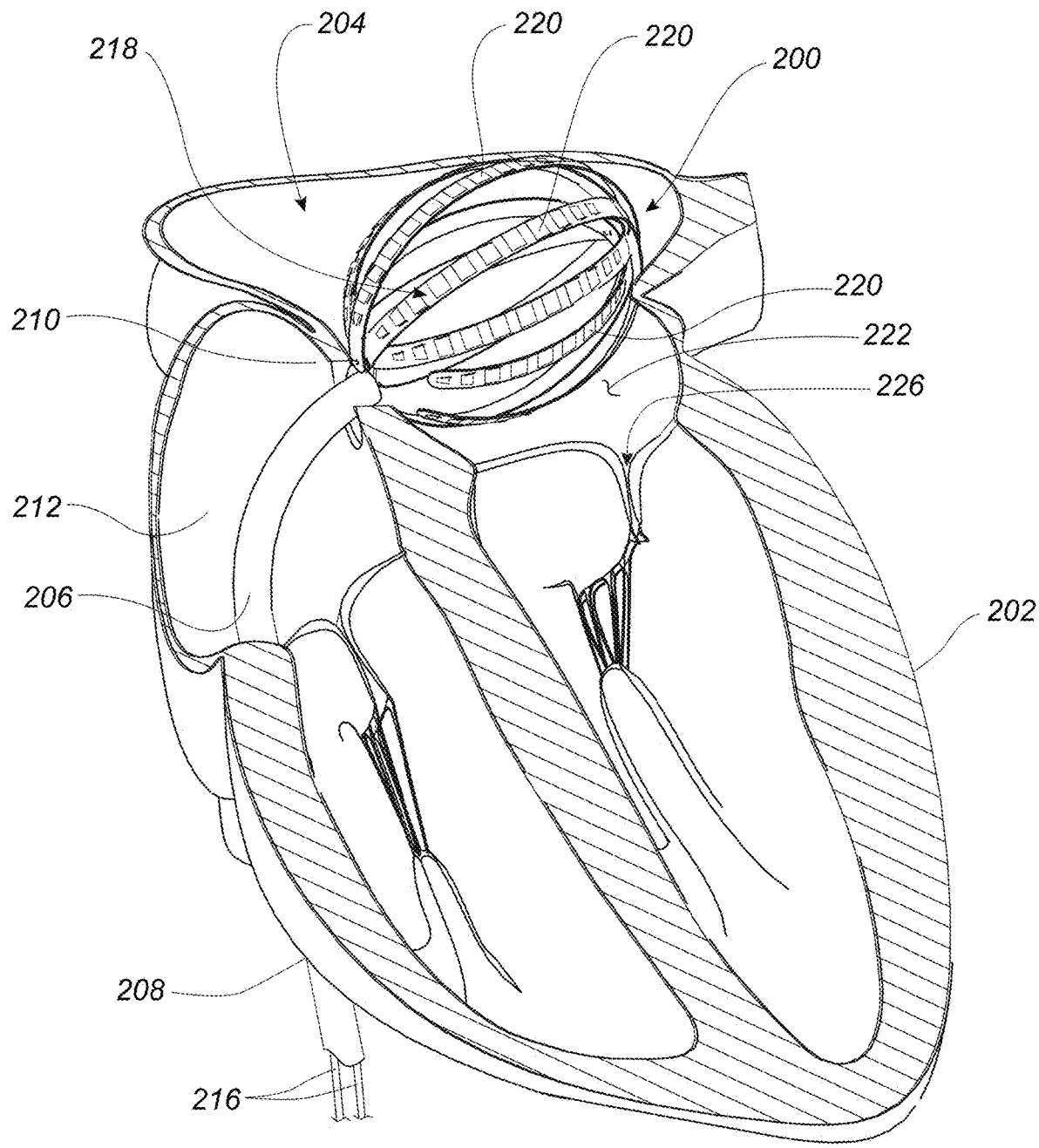
FIG. 2 includes a cutaway diagram of a heart showing a transducer-based device percutaneously placed in a left atrium of the heart according to various example embodiments.

FIG. 2 is a representation of a transducer-based device 200 useful in investigating or treating a bodily organ, for example a heart 202, according to one example embodiment.

Transducer-based device 200 may be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in trans-atrial septum 210 from right atrium 212. (In this regard, transducer-based devices or device systems described herein that include a catheter may also be referred to as catheter devices or catheter-based devices, in some embodiments.) In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown). Electrical conductors 216 provide electrical connections to transducer-based device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In some embodiments, at least some of the transducers 220 are used to sense a physical characteristic of a fluid (e.g., blood) or tissue 222, or both, that may be used to determine a position or orientation (e.g., pose), or both, of a portion of a device 200 within, or with respect to left atrium 204. For example, transducers 220 may be used to determine a location of pulmonary vein ostia or a mitral valve 226, or both. In some embodiments, at least some of the transducers 220 may be used to selectively ablate portions of the tissue 222. For example, some of the transducers 220 may be used to ablate a pattern around the bodily openings, ports, or pulmonary vein ostia, for instance to reduce or eliminate the occurrence of atrial fibrillation. In some embodiments, at least some of the transducers 220 are used to ablate cardiac tissue. In some embodiments, at least some of the transducers 220 are used to sense or sample intra-cardiac voltage data or sense or sample intra-cardiac electrogram data. In some embodiments, at least some of the transducers 220 are used to sense or sample intra-cardiac voltage data or sense or sample intra-cardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intra-cardiac voltage data or intra-cardiac electrogram data at a location at least proximate to a tissue location ablated by at least a second one of the transducers 220. In some embodiments, the first one of the transducers 220 is other than the second one of the transducers 220.

Figure 3A:
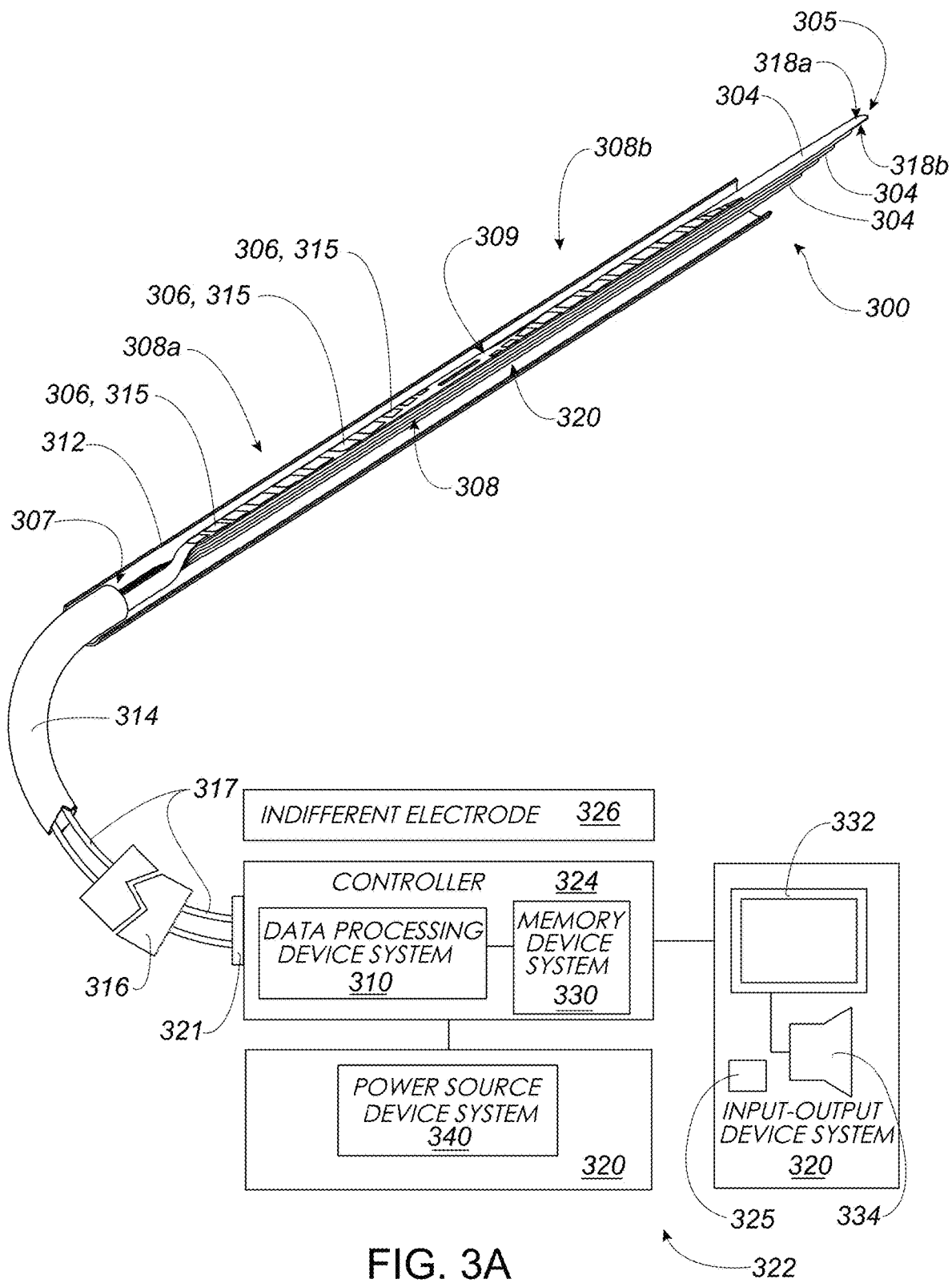
FIG. 3A includes a partially schematic representation of a medical system according to various example embodiments, the medical system including a data processing device system, an input-output device system, a memory device system, and a transducer-based device having a plurality of transducers and an expandable structure shown in a delivery or unexpanded configuration.
Figure 3B:
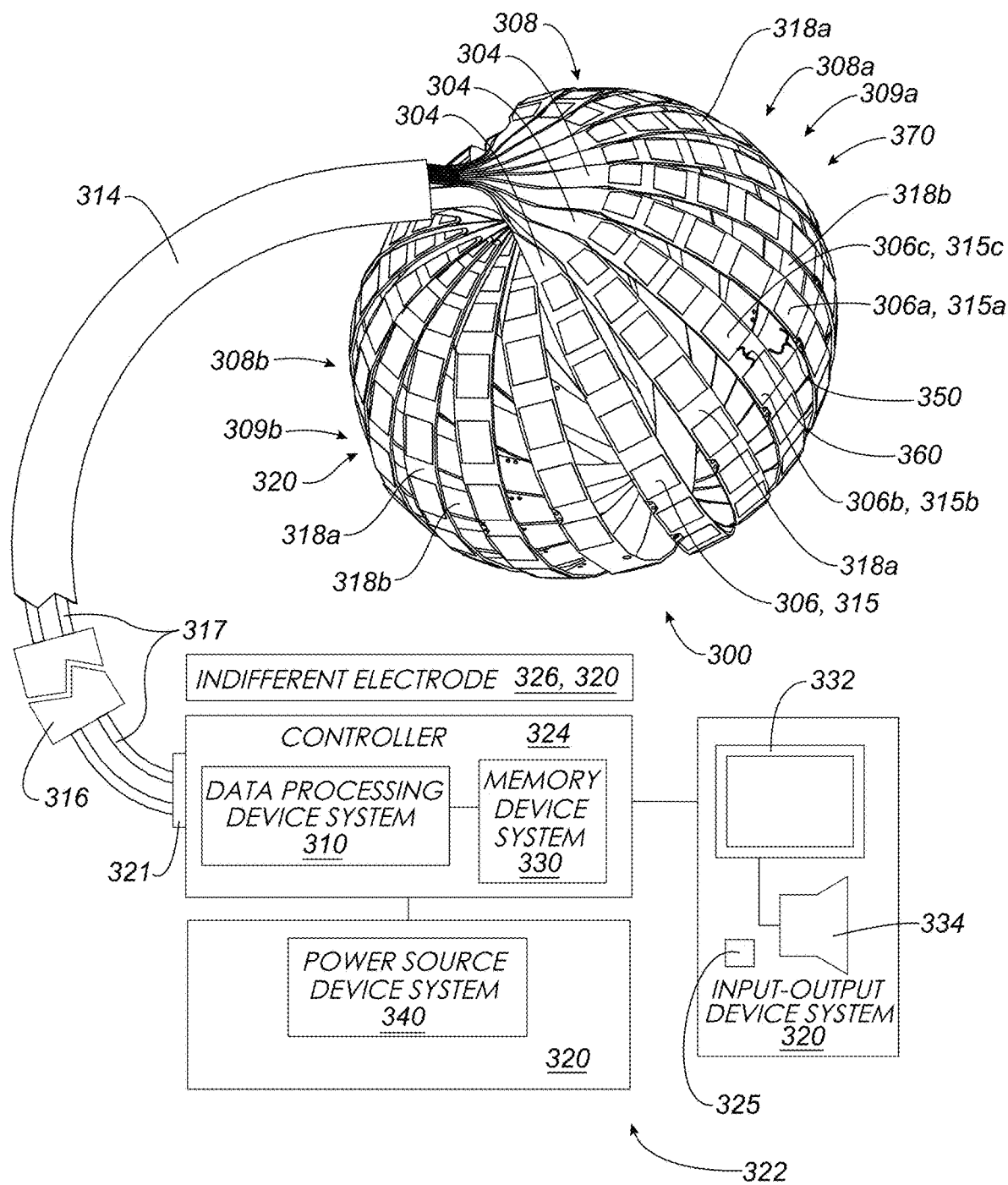
FIG. 3B includes the representation of the medical system of FIG. 3A with the expandable structure shown in a deployed or expanded configuration, according to various example embodiments.

FIGS. 3A and 3B show a transducer-based device system (e.g., a portion thereof shown schematically) that includes a transducer-based device 300 according to one illustrated embodiment. Transducer-based device 300 includes a plurality of elongate members 304 (three called out in each of FIGS. 3A and 3B) and a plurality of transducers 306 (three called out in FIG. 3A and three called out in FIG. 3B as 306a, 306b and 306c). The plurality of transducers 306 is positionable in a distribution (e.g., a spaced-apart distribution) within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arranged to form a two- or three-dimensional distribution, grid or array of the transducers capable of mapping, ablating or stimulating an inside surface of a bodily cavity or lumen without requiring mechanical scanning. As shown, for example, in FIG. 3A, the plurality of transducers 306 are arranged in a distribution receivable in a bodily cavity.

The elongate members 304 are arranged in a frame or structure 308 that is selectively movable between an unexpanded or delivery configuration (e.g., as shown in FIG. 3A) and an expanded or deployed configuration (e.g., as shown in FIG. 3B) that may be used to position elongate members 304 against a tissue surface within the bodily cavity or position the elongate members 304 in the vicinity of the tissue surface. In some embodiments, structure 308 has a size in the unexpanded or delivery configuration suitable for delivery through a bodily opening (e.g., via catheter sheath 312) to the bodily cavity. In some embodiments, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit). The elongate members 304 may include a plurality of different material layers. Each of the elongate members 304 may include a plurality of different material layers. The structure 308 may include a shape memory material, for instance Nitinol. The structure 308 may include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity or the requirements for successful ablation of a desired pattern.

Figure 4:
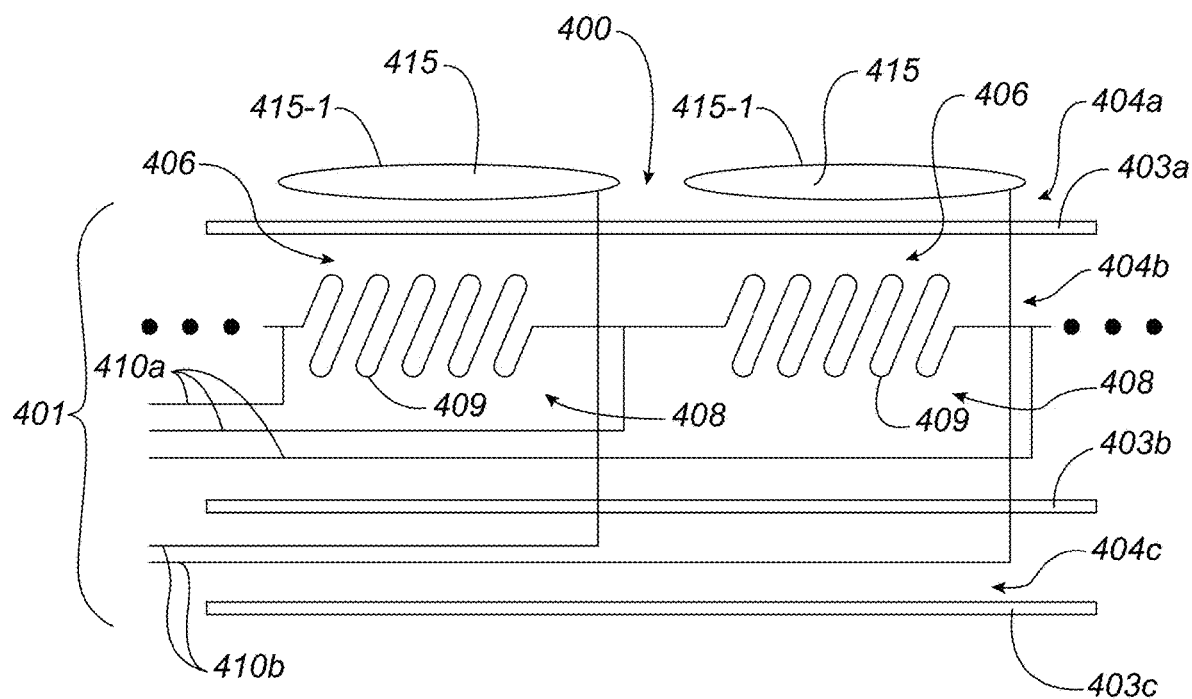
FIG. 4 includes a schematic representation of a transducer-based device that includes a flexible circuit structure according to various example embodiments.

FIG. 4 is a schematic side elevation view of at least a portion of a transducer-based device 400 that includes a flexible circuit structure 401 that is employed to provide a plurality of transducers 406 (two called out) according to various example embodiments. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 may be formed by various techniques including flexible printed circuit techniques. In some embodiments, the flexible circuit structure 401 includes various layers including flexible layers 403a, 403b and 403c (e.g., collectively flexible layers 403). In some embodiments, each of flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415.

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and may be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, may be included.

In some embodiments, electrodes 415 are employed to selectively deliver RF energy to various tissue structures within a bodily cavity (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example. In some embodiments, each electrode 415 is employed to sense or sample an electrical potential in the tissue proximate the electrode 415 at a same or different time than delivering energy sufficient for tissue ablation. In some embodiments, each electrode 415 is employed to sense or sample intra-cardiac voltage data in the tissue proximate the electrode 415. In some embodiments, each electrode 415 is employed to sense or sample data in the tissue proximate the electrode 415 from which an electrogram (e.g., an intra-cardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring to FIGS. 3A, 3B, transducer-based device 300 may communicate with, receive power from or be controlled by a transducer-activation system 322. In some embodiments, elongate members 304 may form a portion of an elongated cable 316 of control leads 317, for example by stacking multiple layers, and terminating at a connector 321 or other interface with transducer-activation system 322. The control leads 317 may correspond to the electrical connectors 216 in FIG. 2 in some embodiments. The transducer-activation device system 322 may include a controller 324 that includes a data processing device system 310 (e.g., from FIG. 1) and a memory device system 330 (e.g., from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

Transducer-activation device system 322 includes an input-output device system 320 (e.g., from FIG. 1) communicatively connected to the data processing device system 310 (e.g., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a physician or technician. For example, output from a mapping process may be displayed on a display device system 332. Input-output device system 320 may include a sensing device system 325 configured to detect various characteristics including, but not limited to, at least one of tissue characteristics (e.g., electrical characteristics such as tissue impedance, tissue type, tissue thickness) and thermal characteristics such as temperature. In this regard, the sensing device system 325 may include one, some, or all of the transducers 306 (or 406 of FIG. 4) of the transducer based device 300, including the internal components of such transducers shown in FIG. 4, such as the electrodes 315 (provided as part of transducer 306 and identified as 315*a*, 315*b* and 315*c* for respective ones of transducers 306*a*, 306*b* and 306*c*) (or 415) and temperature sensors 408.

Transducer-activation device system 322 may also include a power source device system 340 including one or more power source devices connected to transducers 306. In this regard, although FIG. 3A shows a communicative connection between the power source device system 340 and the controller 324 (and its data processing device system 310), the power source device system 340 may also be connected to the transducers 306 via a communicative connection that is independent of the communicative connection with the controller 324 (and its data processing device system 310). For example, the power source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the power source device system 340 may provide results of its delivering energy to, receiving energy from, or both delivering energy to and receiving energy from one or more of the transducers 306 to the controller 324 (and its data processing device system 310) via the communicative connection between the power source device system 340 and the controller 324. In various embodiments, power source device system 340 may transmit radio frequency (RF) power and may alternately be referred to as RF power source device system 340.

In any event, the number of power source devices in the power source device system 340 is fewer than the number of transducers in some embodiments. The power source device system 340 may, for example, be connected to various selected transducers 306 to selectively provide energy in the form of electrical current or power (e.g., RF power), light or low temperature fluid to the various selected transducers 306 to cause ablation of tissue. The power source device system 340 may, for example, selectively provide energy in the form of electrical current to various selected transducers 306 and measure a temperature characteristic, an electrical characteristic, or both at a respective location at least proximate each of the various transducers 306. The power source device system 340 may include various electrical current sources or electrical power sources as power source devices. In some embodiments, an indifferent electrode 326 is provided to receive at least a portion of the energy transmitted by at least some of the transducers 306. Consequently, although not shown in FIG. 3A, the indifferent electrode 326 may be communicatively connected to the power source device system 340 via one or more communication lines in some embodiments. In addition, although shown separately in FIG. 3A, indifferent electrode 326 may be considered part of the power source device system 340 in some embodiments. In various embodiments, indifferent electrode 326 may be positioned outside of the bodily cavity in which the transducers 306 are located. In various embodiments, indifferent electrode 326 is positioned on an external surface (e.g., a skin-based surface) of a body that comprises the bodily cavity into which at least transducers 306 are to be delivered.

It is understood that input-output device system 320 may include other systems. In some embodiments, input-output device system 320 may optionally include power source device system 340, transducer-based device 300 or both power source device system 340 and transducer-based device 300 by way of non-limiting example. Input-output device system 320 may include the memory device system 330 in some embodiments.

Structure 308 may be delivered and retrieved via a catheter member, for example a catheter sheath 312. In some embodiments, a structure provides expansion and contraction capabilities for a portion of the medical device (e.g., an arrangement, distribution or array of transducers 306). The transducers 306 may form part of, be positioned or located on, mounted or otherwise carried on the structure and the structure may be configurable to be appropriately sized to slide within catheter sheath 312 in order to be deployed percutaneously or intravascularly. FIG. 3A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318*a* that is positionable to face an interior tissue surface within a bodily cavity and a second or back surface 318*b* opposite across a thickness of the intermediate portion 309 from the front surface 318*a*. In some embodiments, each of the elongate members 304 is arranged front surface 318*a*-toward-back surface 318*b* in a stacked array during an unexpanded or delivery configuration similar to that described in co-assigned International Application No.: PCT/US2012/022061 and co-assigned International Application No.: PCT/US2012/022062. In many cases a stacked array allows the structure 308 to have a suitable size for percutaneous or intravascular delivery. In some embodiments, the elongate members 304 are arranged to be introduced into a bodily cavity distal end 305 first. For clarity, not all of the elongate members 304 of structure 308 are shown in FIG. 3A. A flexible catheter body 314 is used to deliver structure 308 through catheter sheath 312.

In a manner similar to that described in co-assigned International Application No.: PCT/US2012/022061 and co-assigned International Application No.: PCT/US2012/022062, each of the elongate members 304 is arranged in a fanned arrangement 370 in FIG. 3B. In some embodiments, the fanned arrangement 370 is formed during the expanded or deployed configuration in which structure 308 is manipulated to have a size too large for percutaneous or intravascular delivery. In some embodiments, structure 308 includes a proximal portion 308a having a first domed shape 309a and a distal portion 308b having a second domed shape 309b. In some embodiments, the proximal and the distal portions 308a, 308b include respective portions of elongate members 304. In some embodiments, the structure 308 is arranged to be delivered distal portion 308b first into a bodily cavity when the structure is in the unexpanded or delivery configuration as shown in FIG. 3A. In some embodiments, the proximal and the distal portions 308a, 308b are arranged in a clam shell configuration in the expanded or deployed configuration shown in FIG. 3B.

The transducers 306 may be arranged in various distributions or arrangements in various embodiments. In some embodiments, various ones of the transducers 306 are spaced apart from one another in a spaced apart distribution in the delivery configuration shown in FIG. 3A. In some embodiments, various ones of the transducers 306 are arranged in a spaced-apart distribution in the deployed configuration shown in FIG. 3B. In some embodiments, various pairs of transducers 306 are spaced apart with respect to one another. In some embodiments, various regions of space are located between various pairs of the transducers 306. For example, in FIG. 3B the transducer-based device 300 includes at least a first transducer 306a, a second transducer 306b and a third transducer 306c (all collectively referred to as transducers 306). In some embodiments each of the first, the second and the third transducers 306a, 306b and 306c are adjacent transducers in the spaced-apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device 300 (e.g., a portion of an elongate member 304) is between the second and the third transducers 306b, 306c. In some embodiments, each of the first and the second regions of space 350, 360 do not include a transducer of transducer-based device 300. In some embodiments, each of the first and the second regions of space 350, 360 do not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

FIG. 6 includes a data generation and flow diagram, which may implement various embodiments of method 600 by way of associated computer-executable instructions, according to some example embodiments. In various example embodiments, a memory device system (e.g., memory device systems 130, 330) is communicatively connected to a data processing device system (e.g., data processing device systems 110 or 310, otherwise stated herein as "e.g., 110, 310") and stores a program executable by the data processing device system to cause the data processing device system to execute various embodiments of method 600 via interaction with at least, for example, a transducer-based device (e.g., transducer-based devices 200, 300, or 400). In these various embodiments, the program may include instructions configured to perform, or cause to be performed, various ones of the instructions associated with execution of various embodiments of method 600. In some embodiments, method 600 may include a subset of the associated blocks or additional blocks than those shown in FIG. 6. In some embodiments, method 600 may include a different sequence between various ones of the associated blocks than those shown in FIG. 6.

Figure 5A:
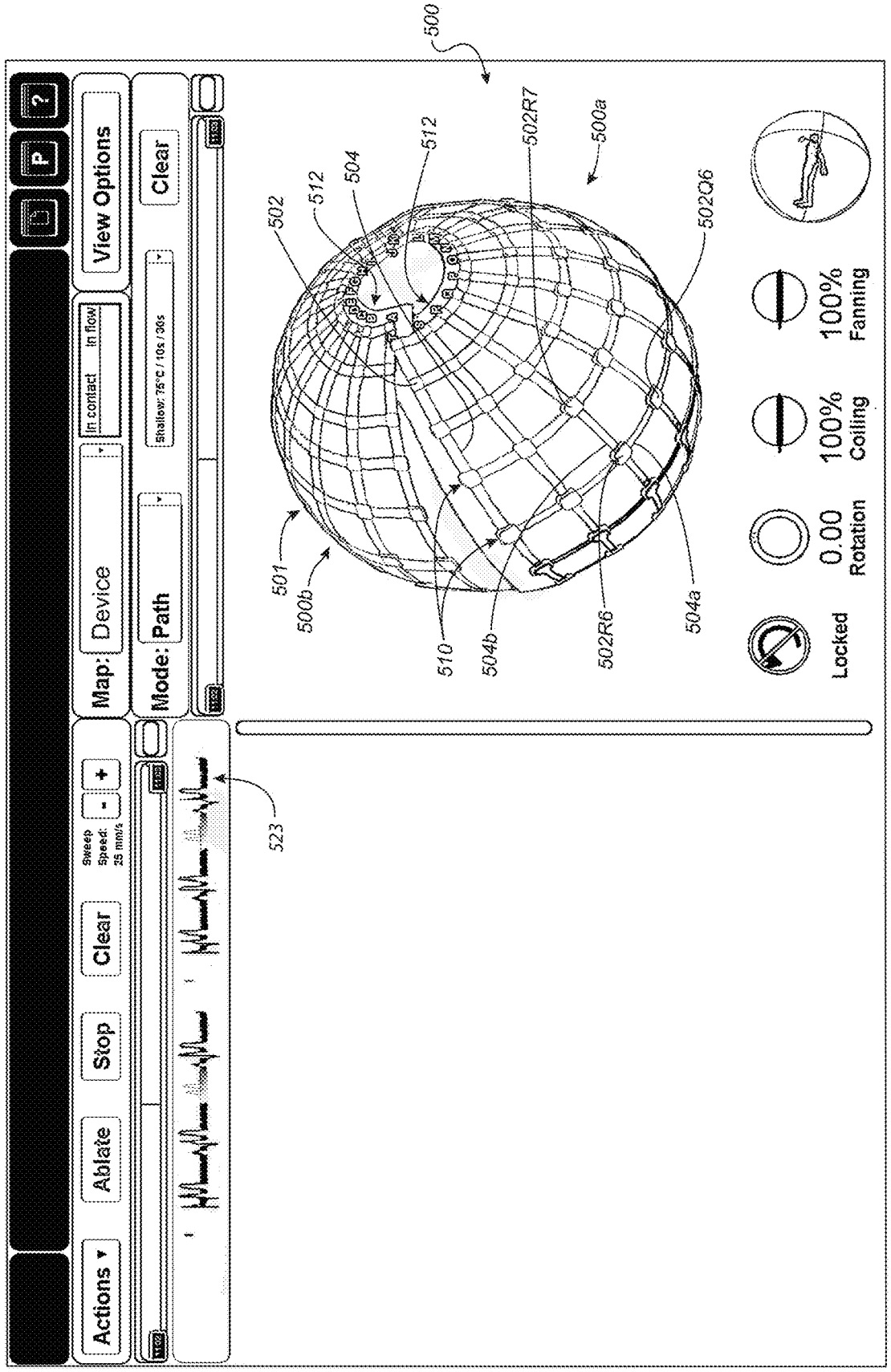
FIG. 5A includes a graphical interface providing a graphical representation of at least a portion of a transducer-based device according to various example embodiments, the graphical representation including a plurality of graphical elements that include a plurality of transducer graphical elements and a plurality of between graphical elements, according to various example embodiments.

In some embodiments, block 602 is associated with computer-executable instructions (e.g., graphical representation instructions or graphical interface instructions provided by a program) configured to cause an input-output device system (e.g., input-output device system 120 or 320) to display a graphical representation of at least a portion of a transducer-based device (e.g., structure 308 in FIG. 3). FIG. 5A illustrates a graphical interface including a graphical representation 500 provided by the input-output device system according to one example embodiment provided in accordance with instructions associated with block 602 in FIG. 6. The instructions associated with block 602 may be configured to access a predefined model (e.g., a computer-aided-design (CAD) or other computer-readable model stored in memory device system 130, 330) of the at least the portion of the transducer-based device and display the at least the portion of the transducer-based device according to such model. In some embodiments, the transducer-based device is a catheter-based device similar to devices 200 and 300 shown respectively in FIGS. 2 and 3. In some embodiments encompassing FIG. 5A, the representation of the transducer-based device is provided by or among various elements of graphical representation 500. In some embodiments, the graphical interface depicts graphical representation 500 of the transducer-based device as including a first domed portion 500a associated with a first domed portion of the transducer-based device (e.g., proximal portion 308a when having the first domed shape 309a) and a second domed portion 500b associated with a second domed portion of the transducer-based device (e.g., distal portion 308b having the second domed shape 309b). Various other transducer-based devices may be depicted according to the instructions associated with block 602 in other embodiments. FIGS. 5A, 5B, 5C, 5D, 5E, 5F, 5G, and 5H (collectively FIG. 5) are presented in this disclosure in association with various embodiments. It is understood that each of these embodiments need not be associated with all of the FIG. 5, and in some cases will only be associated with a subset of the FIG. 5.

In some embodiments, the graphical representation 500 includes a plurality of graphical elements 501. Each of the graphical elements 501 is respectively associated with a respective one of a plurality of transducer sets. Each respective transducer set includes at least one of a plurality of transducers included as part of the transducer-based device (e.g., transducer-based devices 200, 300, or 400) and each respective transducer set has at least one different transducer than another of the other transducer sets. In some embodiments, each respective transducer set has at least one different transducer than each of the others of the other transducer sets.

In some embodiments, each of at least some of the graphical elements 501 are provided by a respective one of a plurality of transducer graphical elements 502 that include at least a first transducer graphical element 502Q6, a second transducer graphical element 502R6, and a third transducer graphical element 502R7 (e.g., all the transducer graphical elements collectively referred to as transducer graphical elements 502). In some embodiments, each transducer graphical element 502 is associated with a single respective transducer of the transducer-based device. In some example embodiments, each transducer graphical element 502 is representative of a respective transducer of the transducer-based device. In some example embodiments, each transducer graphical element 502 is representative of a location or position of a respective transducer of the transducer-based device. In some embodiments, the graphical representation 500 includes a first spatial relationship or arrangement between the displayed transducer graphical elements 502 that is consistent with a second spatial relationship or arrangement between the corresponding transducers associated with the transducer graphical elements 502. An electrocardiogram (ECG/EKG) signal 523 is also shown in the graphical interface of FIG. 5A.

In some embodiments, each of at least some of the graphical elements 501 are provided by a respective one of a plurality of between graphical elements 504 including a first between graphical element 504a and a second between graphical element 504b (e.g., all the between graphical elements collectively referred to as between graphical elements 504). In various embodiments, each of the between graphical elements 504 is associated with a set of at least two of the transducers of the transducer-based device. In some example embodiments, each of the between graphical elements 504 is associated with a pair of transducers in the transducer-based device. In some example embodiments, each between graphical element 504 is associated with a region of space between a respective pair of transducers in the transducer-based device. In some example embodiments, each between graphical element 504 is associated with a region of space between a respective pair of adjacent ones of the transducers in the transducer-based device.

In some embodiments, first transducer graphical element 502Q6 is associated with a first transducer (e.g., first transducer 306a) of the transducer-based device, second transducer graphical element 502R6 is associated with a second transducer (e.g., second transducer 306b) of the transducer-based device, and third transducer graphical element 502R7 is associated with a third transducer (e.g., third transducer 306c) of the transducer-based device. In some embodiments, the first between graphical element 504a is associated with a first region of space that is between the first and the second transducers and the second between graphical element 504b is associated with a second region of space that is between the second and the third transducers. In this illustrated embodiment, the first region of space is a region of space that is not associated with any physical part of the transducer-based device (e.g., first region of space 350) and the second region of space is a region of space that is associated with a physical part of the transducer-based device (e.g., second region of space 360). In some embodiments, each of the first and the second between graphical elements 504a, 504b is associated with a region of space that does not include a transducer of the transducer-based device. In some embodiments, each of the first and the second between graphical elements 504a, 504b is associated with a region of space that does not include any transducer. It is understood that a "region of space" need not be a vacant space but may include physical matter therein.

In FIG. 5A, at least a portion of the transducer graphical elements 502, and at least a portion of the between graphical elements 504 are arranged in a plurality of rows 510 (two called out) and a plurality of columns 512 (two called out, each column 512 identified in the graphical representation by a respective one of letters "A", "B", "C", "D", "E", "F", "G", "H", "I", "J", "K", "L", "M", "N", "O", "P", "Q", "R", "S", and "T"). In this regard, it may be considered that the transducers (e.g., 306 in FIGS. 3A, 3B) corresponding to the transducer graphical elements 502 are arranged in an arrayed distribution that includes a plurality of intersecting transducer rows and transducer columns, a respective group of the plurality of transducers arranged along each of the transducer rows, and a respective group of the plurality of transducers arranged along each of the transducer columns. Adjacent ones of the transducer columns may be separated from each other at least by a non-physical portion of the transducer-based system, e.g., corresponding to region of space 350 in FIG. 3B, and adjacent ones of the transducer rows may be separated from each other at least by a physical portion (e.g., a portion between transducers 306 along a same elongate member 304) of the transducer-based system (e.g., 200, 300, or 400). In some embodiments, it may be considered that the transducers (e.g., 306 in FIGS. 3A, 3B) corresponding to the transducer graphical elements 502 are arranged in a distribution that includes a grid that includes at least three rows and at least three columns, each of the columns arranged to intersect each of the rows at a respective intersection location, a respective one of the transducers arranged at each respective intersection location.

Referring back to FIG. 5A, a portion of each of the columns 512 corresponds to a region of space associated with a physical portion of the transducer-based device (e.g., an elongate member 304), according to some embodiments. In some embodiments, each of the columns 512 corresponds to at least a portion of the transducers located on a particular elongate member of a transducer-based device (e.g., an elongate member 304). In some embodiments, each of the columns 512 corresponds to at least a portion of the transducers located on a respective one of a pair of domed portions 500a, 500b arranged in a clam shell configuration similar to the embodiments of FIG. 3B. In embodiments in which each domed portion is formed by a respective portion of each of a plurality of elongate members (e.g., elongate members 304), a set of two or more of the columns 512 may correspond to the transducers located on a single one of the elongate members.

In some embodiments, a portion of each of the rows 510 corresponds to regions of space not associated with any physical portion of the transducer-based device (e.g., regions of space 350 between adjacent ones of the elongate members 304). In other example embodiments, different numbers of transducer graphical elements 502 and different numbers and spatial relationships or arrangements of between graphical elements 504 may be depicted in the graphical representation. In other example embodiments, different numbers and spatial relationships or arrangements of rows 510 and columns 512 may be depicted in the graphical representation. In various embodiments, each of the between graphical elements (e.g., between graphical elements 504) depicted in the graphical representation are representative of a respective physical path extending between a respective pair of transducers of the transducer-based device. Each of the physical paths may extend over a physical surface of the transducer-based device or over a portion of an opening defined by a physical surface of the transducer-based device.

In FIG. 5A, the transducer graphical elements 502 and the between graphical elements 504 in each respective one of the rows 510 are interleaved with respect to one another along the respective one of the rows 510. In this illustrated embodiment, the transducer graphical elements 502 and the between graphical elements 504 in each respective one of the columns 512 are interleaved with respect to one another along the respective one of the columns 512. In this illustrated embodiment, each one of the plurality of columns 512 shares a same transducer graphical element 502 with one of the plurality of rows 510. In this illustrated embodiment, each respective one of the plurality of columns 512 excludes any of the between graphical elements 504 included in each of the plurality of rows 510. In this illustrated embodiment, at least a first one of the between graphical elements 504 (e.g., second between graphical element 504b) is depicted in the graphical representation between two adjacent ones of the plurality of rows 510 and at least a second one of the plurality of between graphical elements 504 (e.g., first between graphical element 504a) is positioned between two adjacent ones of the plurality of columns 512. In some embodiments, the plurality of rows 510 and the plurality of columns 512 are depicted as a three-dimensional arrangement in the graphical representation. In some embodiments, at least two of the plurality of columns 512 are depicted in the graphical representation extending along respective directions that converge with respect to one another. In this illustrated embodiment, at least two of the plurality of columns 512 are depicted in the graphical representation extending along non-parallel directions and at least two of the plurality of rows 510 are depicted extending along parallel directions. In this illustrated embodiment, the rows 510 and the columns 512 are depicted in the graphical representation in an arrangement in which the columns 512 are circumferentially arranged. In this illustrated embodiment, the rows 510 and the columns 512 are depicted in the graphical representation in an arrangement having a generally spherical shape. The plurality of columns 512 may be depicted like lines of longitude, and the plurality of rows 510 may be depicted like lines of latitude. In some embodiments, columns 512 are considered rows, and rows 510 are considered columns in various ones of FIG. 5. In this case, each particular column may be identified by the numerical portion of the alpha-numeric identifier of the transducer graphical element 502 arranged along the particular column, and each particular row may be identified by the alphabetic portion of the alpha-numeric identifier of the transducer graphical element 502 arranged along the particular row.

Figure 5B:
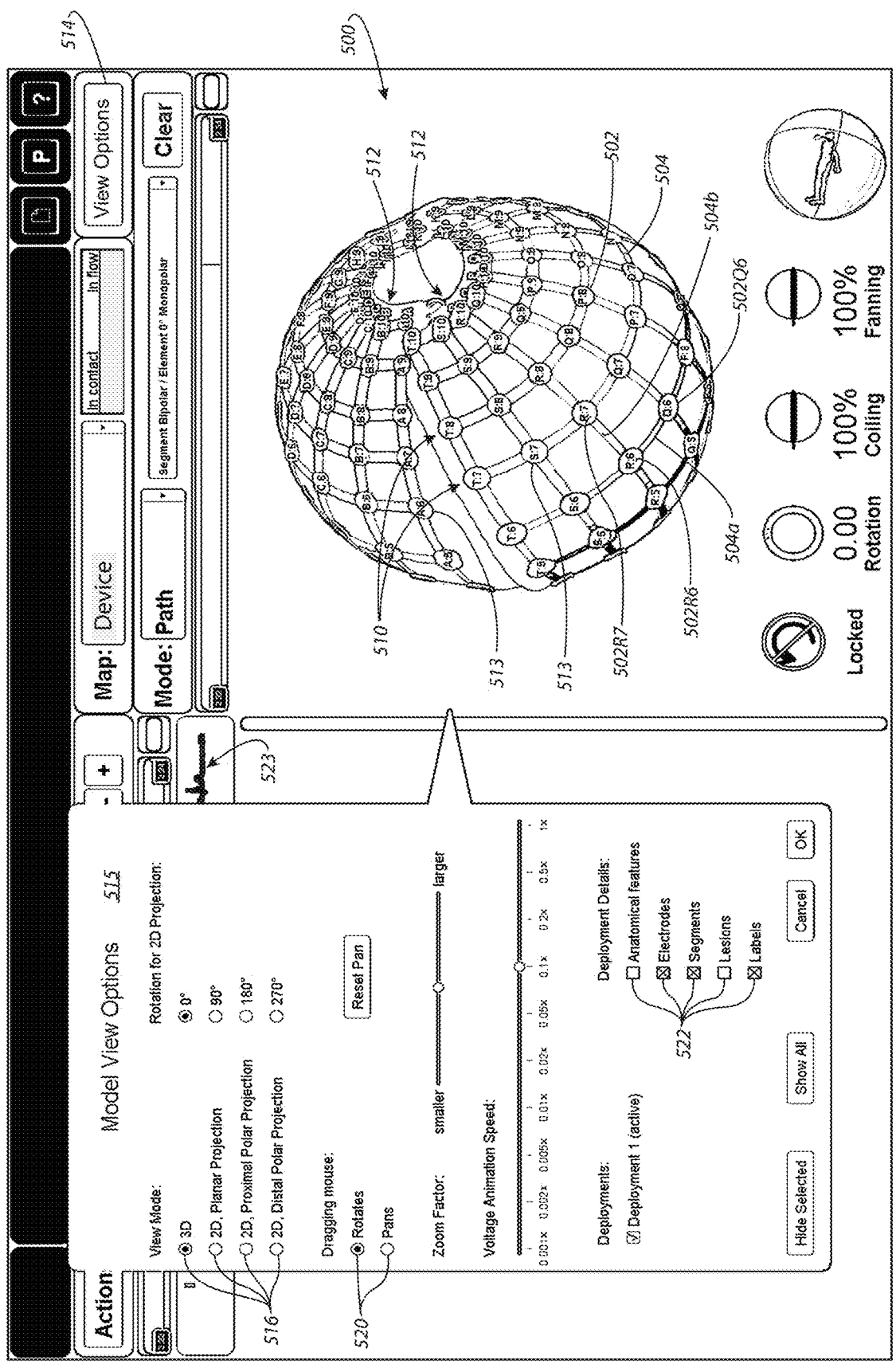
FIG. 5B includes the graphical representation provided by the graphical interface of FIG. 5A with at least some of the transducer graphical elements identified by identification labels, according to various example embodiments.

The graphical interface of FIG. 5B includes the graphical representation 500 with the addition of identification labels 513 (two called out, e.g., as "A:6" and "S:7") to each of the transducer graphical elements 502. In some embodiments, identification labels are applied by operating the input-output device system to activate a control button 514 identified as "View Options". In some embodiments, a selection box 522 allows for the selective inclusion of identification labels 513 (e.g., indicated as "Labels" in this illustrated embodiment). In some embodiments, each of the identification labels 513 employs an alpha-numeric format including a letter representative of the column 512 in which a corresponding transducer graphical element is located and a number representative of a location of the transducer graphical element 502 in the corresponding column 514. Other identification schemes may be employed in other embodiments.

Selection, activation, or both selection and activation of a control button, a selection box, or other graphical element provided in the various embodiments may be accomplished via various input-output device system controls that may include a touch screen, keyboard or computer mouse by way of non-limiting example. In various embodiments, selection of control button 514 causes the selection menu 515 identified as "Model View Options" to appear in the graphical representation. Selection menu 515 provides various selection boxes 516 that are selectable to vary the graphical representation of the portion of the transducer-based device between a three-dimensional graphical representation (e.g., as depicted in FIGS. 5A and 5B) and a two dimensional graphical representation (e.g., as depicted in FIG. 5D). Various two-dimensional graphical representations are possible in various embodiments. For example, the two-dimensional graphical representation depicted in FIG. 5D is shown in a "Mercator-type" representation in which the first domed portion 500a (e.g., shown in FIG. 5A) of the depicted transducer-based device is depicted as a first Mercator projection 518a and the second domed portion 500b (e.g., shown in FIG. 5A) of the depicted transducer-based device is a depicted as a second Mercator projection 518b. The first and the second Mercator projections 518a and 518b advantageously allow for simultaneous viewing of all the transducer graphical elements 502 and the between graphical elements 504. Other two-dimensional graphical representations including polar projections are also selectable.

In various embodiments where the transducer-based device is deployed in a bodily cavity (e.g., when the transducer-based device takes the form of a catheter device arranged to be percutaneously or intravascularly delivered to a bodily cavity), it may be desirable to perform various mapping procedures in the bodily cavity. Although these mapping procedures may be implemented at various times, such as any time during the generation of or after the display of the graphical representation via the instructions associated with block 602. It is noted that, in some embodiments, the mapping procedure need not be limited to the mapping of various anatomical landmarks. For example, when the bodily cavity is an intra-cardiac cavity, the mapping procedure may include mapping electrophysiological activity in the intra-cardiac cavity. In some embodiments, the mapping procedure may include mapping varying degrees of contact between various ones of the transducers (e.g., electrodes) and a tissue surface of a bodily cavity into which the transducers are located.

An example of the mapping performed by devices according to various embodiments would be to locate the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating such bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling by fluid of heated transducer elements. A slightly heated arrangement of transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity may be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such may be used to determine which of those transducers are not proximate to tissue, which is indicative of the locations of the ports.

4. The use of transducers that sense force (e.g., force sensors). A set of force detection transducers positioned around the tissue that forms the interior surface of the bodily cavity and across the bodily openings or ports of the bodily cavity may be used to determine which of the transducers are not engaged with the tissue, which is indicative of the locations of the ports.

Figure 5C:
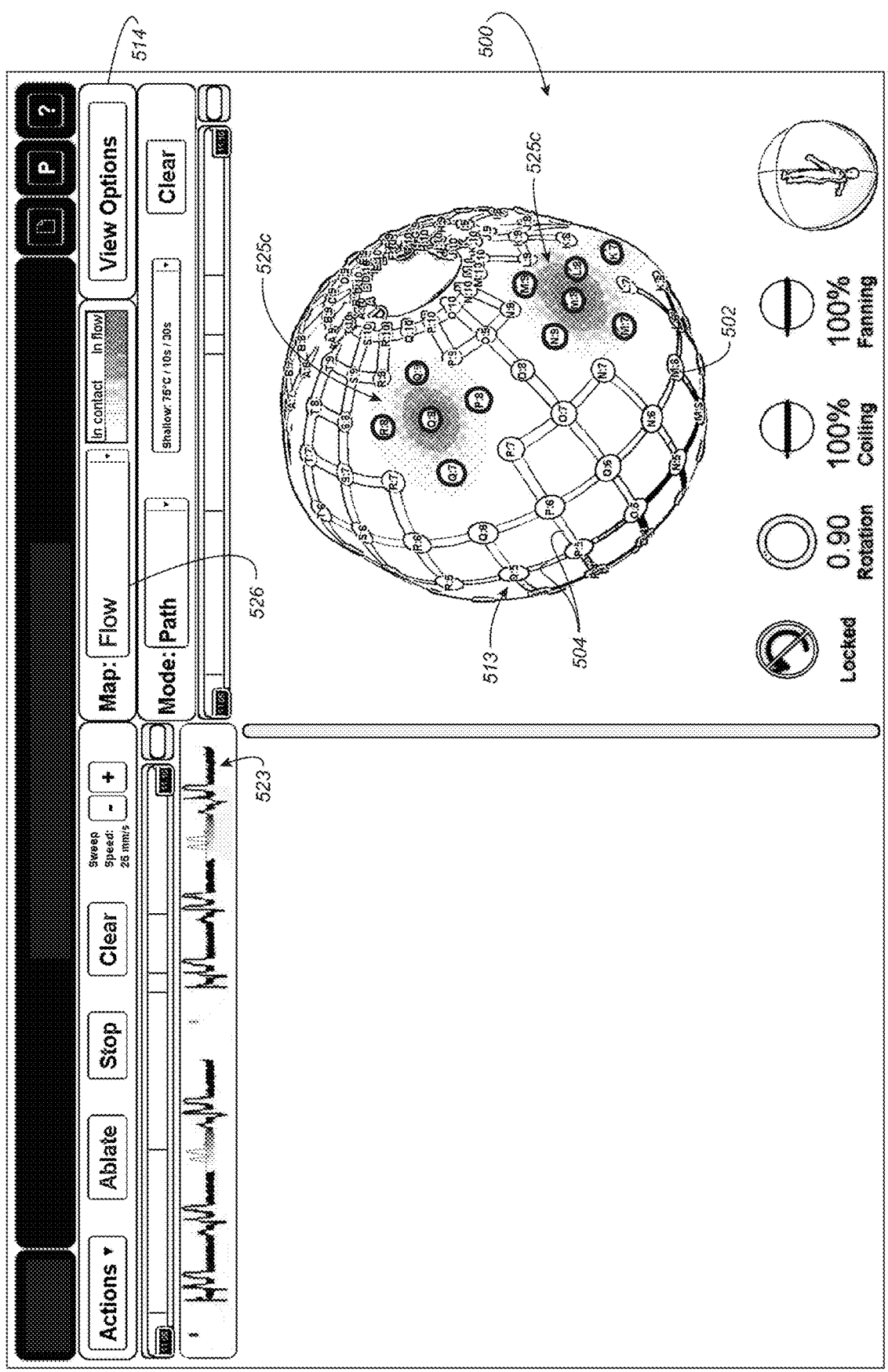
FIG. 5C includes the graphical representation provided by the graphical interface of FIG. 5A with the addition of various regions determined based at least on an analysis of transducer data, according to various example embodiments.
Figure 5D:
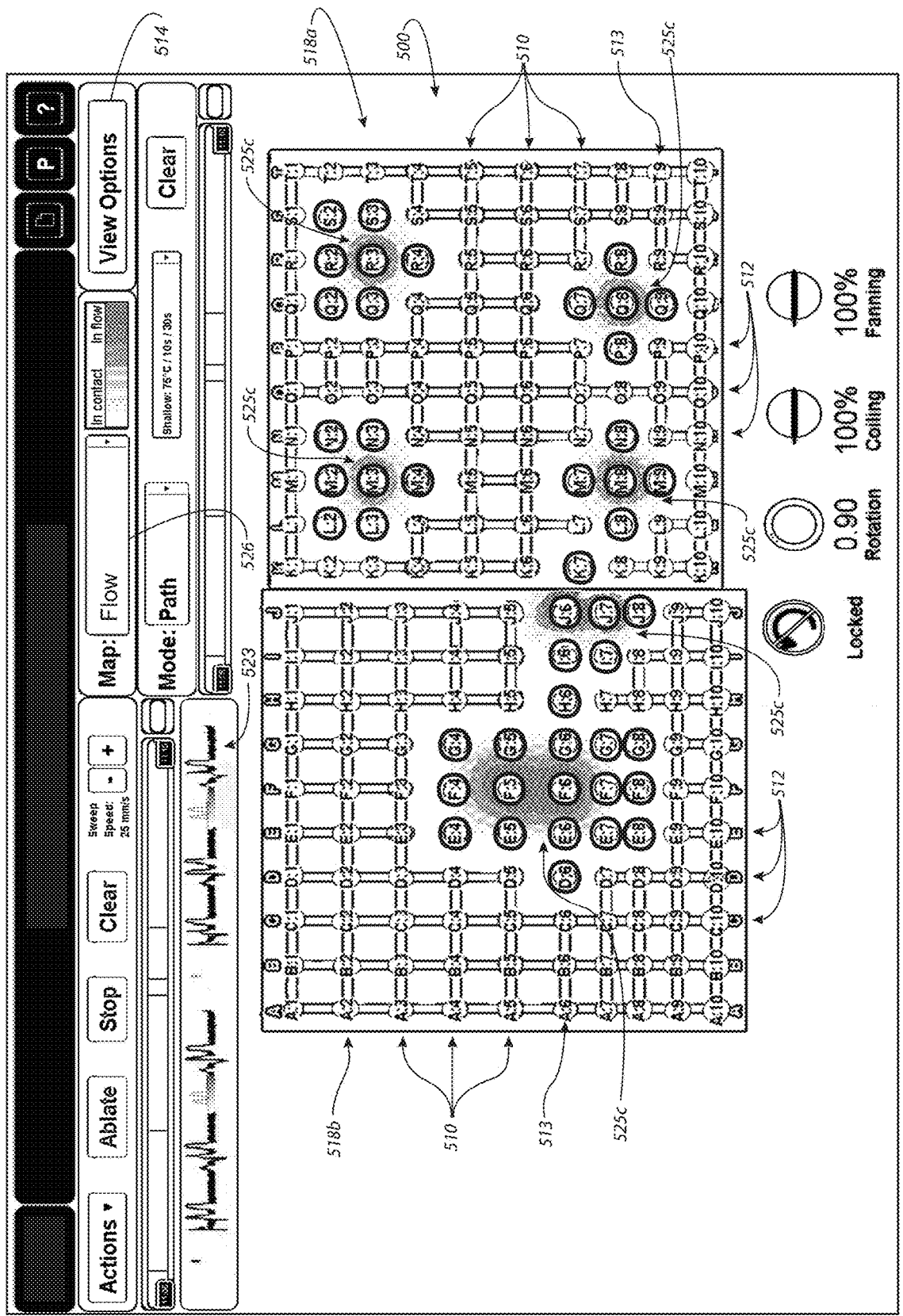
FIG. 5D includes the graphical representation of FIG. 5C depicted two-dimensionally, according to various example embodiments.

The graphical representation depicted by the graphical interface of FIG. 5C includes various regions 525c (e.g., part of a plurality of regions collectively referred to as regions 525c when considering all of the FIG. 5) added to the graphical representation 500 of the transducer-based device. The regions 525c may be identified and displayed according to the instructions associated with block 602 in FIG. 6, in some embodiments; although such regions 525c may be identified and displayed at other times or according to other instructions. In some embodiments, the graphical interface depicted in FIG. 5C is generated after the transducer-based device was received in a bodily cavity having various anatomical features of interest and the control button 526 identified as "Map" was activated via the input-output device system to select a mode referred to as "Flow". Techniques for flow-based mapping techniques are disclosed in commonly assigned U.S. Patent Application Publication No.: US 2008/0004534. In various embodiments associated with various ones of FIG. 5, the anatomical features of interest are ports of a mitral valve and various pulmonary veins positioned in fluid communication with an intra-cardiac cavity (e.g., a left atrium in some embodiments). In these various embodiments, the transducers of the transducer-based device are distributed adjacent respective regions in the intra-cardiac cavity that may include relatively lower blood flow regions (e.g., adjacent a tissue surface of the intra-cardiac cavity), relatively higher flow regions (e.g., over the ports of the intra-cardiac cavity). It is noted that relatively lower blood flow regions in the intra-cardiac cavity may occur when a transducer is positioned in contact with a tissue surface to restrict blood flow at the contacted tissue. In some example embodiments, the relatively large number of transducers in the distribution advantageously allows for each of the transducers to be positioned adjacent their corresponding regions with little or no repositioning of the transducer-based device thereby facilitating obtaining transducer-based data concurrently from a multitude of locations in the bodily cavity. In some embodiments, activation via the input-output device system of the control button 526 identified as "Map" may allow for other types of maps, including but not limited to, tissue contact maps, isochronal maps, isopotential maps, propagation maps, and various other voltage maps associated with intra-cardiac electrical activity. Referring back to FIG. 5B, selection menu 515 provides various selection boxes 520 that may control mouse drag functions between rotating and panning modes. A rotating mode may be advantageously used for manipulation of a three-dimensional graphical representation of the transducer-based device to allow for viewing a portion of the three-dimensional graphical representation that was not previously viewable. Selection menu 515 includes a plurality of selection boxes 522 that allow for variations in the viewable content of the graphical representation. In some embodiments, a selection box 522 allows for the selective inclusion in the graphical representation of graphical elements associated with various anatomical features. In some example embodiments, the graphical elements associated with the anatomical features are selectable from a menu and may be tailored to a particular procedure in which the transducer-based device is employed. Various ones of the selection boxes 522 allow for selective inclusions of the transducer graphical elements 502 (e.g., indicated as "Electrodes" in this illustrated embodiment) and the selective inclusion of the between graphical elements 504 (e.g., indicated as "Segments" in this illustrated embodiment). In some embodiments, a selection box 522 allows for the selective inclusion in the graphical representation of graphical elements associated with lesions which may be of particular interest in embodiments in which various transducers of the transducer based-device ablate tissue to form the lesions therein.

It is noted that the transducer graphical elements 502, the between graphical elements 504, or both may have different sizes, shapes or forms than those shown in the illustrated embodiment. In some embodiments, different ones of the transducer graphical elements 502 may be depicted with different shapes, sizes or forms in the graphical representation. In some embodiments, different ones of the between graphical elements 504 may be depicted with different shapes, sizes or forms in the graphical representation.

Having described examples of the graphical representation displayed according to the instructions associated with block 602 in FIG. 6, the data processing device system (e.g., 110, 310) may be configured according to instructions associated with block 604 to receive a selection of at least some of the transducers in a distribution (e.g., a distribution of transducers 306 as shown in FIGS. 3A and 3B), according to some embodiments. Although FIG. 6 shows block 604 located after block 602, some embodiments are not limited to this arrangement, and the selection of the at least some of the transducers in the distribution according to block 604 may occur at any time.

Selection of the at least some of the transducers may take various forms. For example, when the distribution is an arrayed distribution including a plurality of intersecting rows (e.g., 510) and columns (e.g., 512) with a respective group of the transducers arranged along each of the plurality of rows and a respective group of the transducers arranged along each of the plurality of columns (e.g., as described above), the selection of the at least some of the transducers may include (a) a selection of at least some of the transducers in each of at least one of the rows, (b) a selection of at least some of the transducers in each of at least one of the columns, or both (a) and (b). In various embodiments, the selection of the at least some of the transducers in the distribution includes a selection of some but not all of the transducers in the distribution. For example, particular ones of the transducers may be selected to cause tissue ablation in select regions of a bodily cavity in which the distribution of transducers are deployed, the select regions not forming an entirety of a tissue surface defining the bodily cavity.

In various embodiments, reception of the selected at least some of the selected transducers in the distribution is made via an input-output device system (e.g., 120, 320) and includes a user-based selection, via the input-output device system, of the selected at least some of the transducers in the distribution. For example, a user may input information (e.g., via a keyboard or other input device) specifying a particular one or particular ones of the transducers in the distribution that are to be selected. In this regard, the selection according to the instructions associated with block 604 includes, in some embodiments, multiple constituent or sub-selections (although in other embodiments, the selection according to the instructions associated with block 604 includes only a single selection). For instance, in some embodiments, block 604 may include selection instructions configured to cause, due to execution of the selection instructions by the data processing device system (e.g., exemplified by data processing device systems 110, 310), selection of one or more graphical elements. In some embodiments, such selection instructions include a first group of instructions configured to cause the data processing device system to receive or process, via the input-output device system, a user instruction to select one or more graphical elements. In some of these embodiments, such selection instructions also include a second group of instructions configured to cause the data processing device system to perform its own selection of the graphical element in response to receiving the user instruction. For instance, the user instruction to select the graphical element might originate from a user clicking a mouse button (e.g., a first constituent selection) while a cursor is above a user-selected graphical element. In this case, the first group of instructions may configure the data processing device system to recognize this user instruction when it is received via the data input-output device system as a user instruction to select the user-selected graphical element below the cursor at the time of the mouse-button click. In some embodiments, the second group of instructions may configure the data processing device system, in response to the first group of instructions recognizing this user instruction, to perform its own selection (e.g., a second constituent selection) of the user-selected graphical element at least by causing, via the input-output device system, the display of the user-selected graphical element to change one or more visual characteristics of the user-selected graphical element. Accordingly, the selection according to the instructions associated with block 604 may be deemed, in some embodiments, to involve a first, user-based constituent selection and a second, machine-based or automatic constituent selection triggered by the user-based constituent selection.

Although a mouse-click was provided above as an example of a user-based constituent selection, and the changing of a visual characteristic of the user-selected graphical element was provided as an example of a machine-based constituent selection, it should be noted, however, that any form of user-based selection or machine-based selection of a graphical element known in the art may be used. In this regard, direct interaction with a graphical element itself (e.g., by way of a mouse-click on the graphical element) is not required to directly select the graphical element or its corresponding transducer. For example, a user might type a unique identifier associated with a graphical element or transducer via a keyboard, which may cause direct selection of that graphical element or transducer.

Further, although a user-based constituent selection of a user-selected graphical element followed by a machine-based constituent selection of that user-selected graphical element was provided above as an example of constituent selections involved with block 604, it should be noted that a user-based constituent selection of a first user-selected graphical element may also cause a machine-based constituent selection of a second, different, non-user-selected graphical element. For example, a user-performed mouse-click while the mouse cursor is above a user-selected between graphical element 504 (e.g., a user-based constituent selection) may cause, possibly among other things, a machine-based constituent selection of the non-user-selected transducer graphical elements 502 at each end of the user-selected between graphical element 504. In this regard, the phrase, "user-selected", when used herein to describe a selected graphical element (e.g., a transducer graphical element or a between graphical element), is intended to refer to a graphical element directly selected by a user, as opposed to a non-user-selected graphical element, which is a machine-selected graphical element that is machine-selected either in response to no user instruction to select any graphical element or in response to a user instruction to select a user-selected graphical element different than the machine-selected graphical element. In cases where a user selection of a user-selected graphical element causes a machine-selection of a different graphical element, it may be said that the different graphical element is indirectly selected by the user.

Further still, although a user-based constituent selection followed by a machine-based constituent selection was provided above as an example of constituent selections involved with block 604, it should be noted that any number of constituent selections, whether user-based or machine-based, may be involved with block 604. For example, depending upon how the user interface is structured, one or more user-based constituent selections may result in one or more machine-based constituent selections. For instance, multiple user gestures (e.g., a double-fingered gesture on a touch screen, a mouse click-drag-and-release sequence, or other multiple user-gesture technique) might be required to identify a particular user-selected graphical element in order to cause the data processing device system to change the visual characteristics of (or provide another form of selection of) the particular user-selected graphical element. For another example, multiple user-based constituent selections might be a mouse click-and-hold followed by a dragging of a cursor to expand a selection box originating from the initial mouse click location, followed by a releasing of the mouse button to define the final size of the selection box. This initial user-based selection (comprised of the multiple user-based constituent selections) may be recognized by the data processing device system according to the above-discussed first group of instructions, and cause multiple machine-based or automatic constituent selections performed by the data processing device system according to the above-discussed second group of instructions. For instance, these multiple machine-based or automatic constituent selections may include a first constituent selection by the data processing device system of all graphical elements residing within the selection box, followed by a second constituent selection of only those graphical elements deemed to reside within the selection box whose corresponding transducers have been deemed acceptable for selection.

Further still, although one or more user-based constituent selections followed by one or more machine-based constituent selections was provided above as an example of constituent selections involved with block 604, it should be noted that block 604 might not involve any user-based constituent selections. For example, graphical element selection according to block 604 might occur based upon data received from transducers, and this data might result in one or more machine-based or automatic constituent selections performed by the data processing device system.

It should be noted that, whenever a selection of a graphical element is discussed herein, such selection, in some embodiments, may include the above-discussed constituent selections. However, the above-discussed constituent selections are not limited to just selections of graphical elements and may apply to any selection described herein. For example, one or more user-based constituent selections of a user-selected graphical element may lead to one or more machine-based constituent selections of the user-selected graphical element or some other graphical element(s), which may lead to one or more machine-based selections of one or more transducers corresponding to the machine-selected graphical elements, the machine-based selection(s) of the one or more transducers causing an activation of the one or more transducers. For another example, one or more user-based constituent selections of a user-selected graphical element may lead to one or more machine-based constituent selections of one or more data objects associated with the user-selected graphical element, one or more other associated graphical elements, one or more transducers associated with the user-selected graphical element, or one or more other objects associated with the user-selected graphical element, such as for purposes of viewing or changing properties of the one or more data objects or causing an activation based upon information provided by the one or more data objects.

In view of the above-discussion regarding selection types involved with block 604, in some embodiments, the instructions associated with block 604 are provided in a program that includes instructions configured to cause the data processing device system (e.g., 110, 310) to receive a selection from the input-output device system (e.g., 120, 320) of a transducer graphical element (e.g., transducer graphical element 502). In accordance with various activation instructions (e.g., instructions associated with block 608 in FIG. 6), a program may include activation instructions configured to, in response to receiving the selection, cause activation, via the input-output device system, of a particular one of the transducers corresponding to the selected transducer graphical element (e.g., transducer graphical element 502). For another example, in some embodiments, various activation instructions (e.g., instructions associated with block 608) are provided in a program that includes selection instructions configured to cause, due to execution of the selection instructions by the data processing device system (e.g., again exemplified by data processing device systems 110 or 310), reception of a selection from the input-output device system of a between graphical element (e.g., between graphical element 504). In accordance with the instructions associated with block 608, the program may include activation instructions configured to, in response to receiving the selection, cause activation, via the input-output device system, of a respective set of two or more of the transducers (e.g., a pair or other group of the transducers) of the transducers in the distribution corresponding to the between graphical element. Advantageously, selecting and, in some embodiments, activating a set of two or more of the transducers based on a selection of a single graphical element (e.g., between graphical element 504) provides for a workflow that is less cumbersome and more expeditious than individually selecting the respective graphical elements (e.g., transducer graphical element 502) associated with each transducer of the set of two or more of the transducers, especially when 50, 100, 200 or even over 300 or more transducer graphical elements are provided in the graphical representation. This configuration is even more advantageous when a single graphical element (e.g., between graphical element 504) provides additional information (e.g., spatial information) relating each of the transducers in the set of two or more of the transducers. For example, a between graphical element 504 may indicate a distance between or acceptability-of-activation of transducers of a corresponding transducer pair, and, accordingly, the between graphical element 504 provides, in some embodiments, information about the corresponding pair of transducers and, thereby, makes the selection process more efficient. In addition, allowing selection of the between-graphical elements for corresponding transducer activation may provide a more intuitive user interface in certain applications. For example, such an arrangement allows a user to make selections along an ablation path or a path along which data is to be obtained, without having to focus on the transducers required to make that ablation path or acquire that data. The user can, for example, just select a path using between graphical elements (e.g., user-based selection(s)/constituent selection(s)), and the corresponding transducers are automatically selected (e.g., machine-based selection(s)/constituent selection(s)) in response. Since various ones of the between graphical elements need not be tied to any physical portion of the transducer-based device, they may be freely designed to reflect the path (e.g., over tissue or fluid) in which their corresponding transducers will interact when activated (e.g., by causing ablation or gathering data). In this regard, if the between graphical elements are configured to accurately represent their respective path segments in which ablation or data gathering will occur, according to some embodiments, the user may gain an even better understanding of the expected results of activation of the corresponding transducers.

Figure 5E:
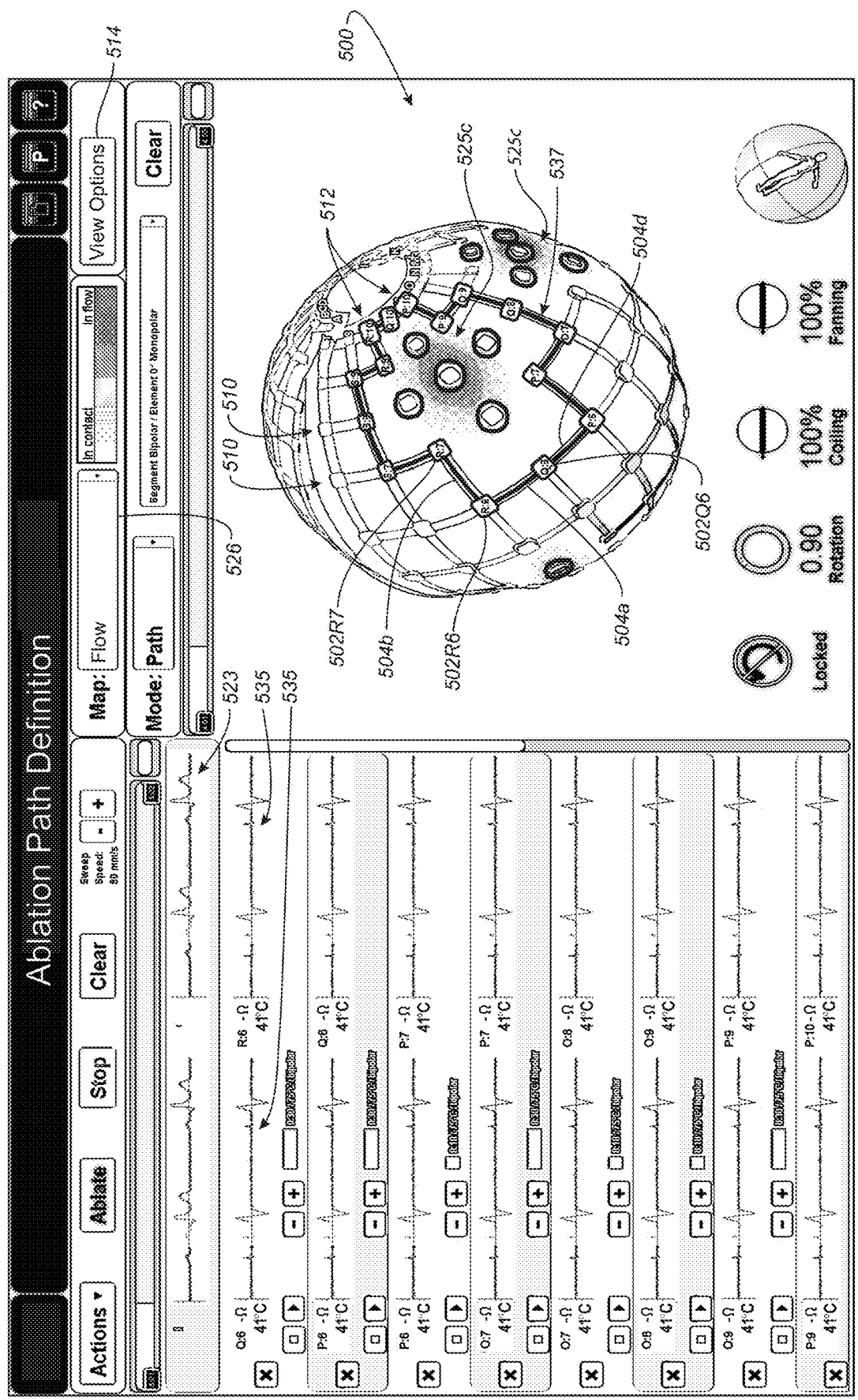
FIG. 5E includes the graphical representation of FIG. 5C with an addition of a depicted path, according to various example embodiments.

An example selection of various graphical elements corresponding to selected particular ones of a distribution of the transducers positionable in a bodily cavity (e.g., particular ones of the transducers 306) is shown in FIG. 5E. In some embodiments, various selected transducer graphical elements 502 associated with a path 537 may be selected (e.g., each selected transducer graphical element 502 indicated by the corresponding identification labels 513: "R:6", "Q:6", "P:6", "P:7", "O:7", "O:8", "O:9", "P:9", "P:10" "Q:10"

"R:10" "R:9", "S:9", "S:8", "S:7", and "R:7"). Also, as shown in FIG. 5E, the between graphical elements 504 associated with path 537 may be selected (e.g., each selected between graphical element 504 herein identified by the corresponding pair of identification labels 513 associated with the transducer graphical elements 502 in which the selected between graphical element 504 is positioned between): "R:6-Q:6", "Q:6-P:6", "P:6-P:7", "P:7-O:7", "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6". Path 537 may, in some embodiments, correspond to an ablation path (e.g., a path along a tissue surface structure that is subject to ablative energy transmitted by the selected ones of the transducers. In some embodiments, selection of various ones of the graphical elements includes (a) a user-based selection of at least some of the transducer graphical elements 502, (b) at least some of the between graphical elements 504, or a combination of (a) and (b). In some embodiments, the selected graphical elements 501 may be selected sequentially along path 537 with an order that corresponds to a positional order of the selected graphical elements 501 along the path 537. In some embodiments, the selected graphical elements 501 may be selected according to an order that does not correspond to a positional order of the selected graphical elements 501 along the path 537. Without limitation, transducers selected in accordance with the instructions associated with block 604 may include a selection of a plurality of transducer sets. In some embodiments, at least some of the selected transducer sets are selected sequentially. In some embodiments, at least some of the transducer sets are selected concurrently. In some embodiments, each of at least some of the transducer sets may be considered to have a single transducer. In some embodiments, each of at least some the transducer sets may be considered to have at least two transducers. In some embodiments, the selected transducer sets may be selected according to a defined order. In some embodiments, the selected transducer sets may be selected randomly or pseudo-randomly.

In some embodiments, the display instructions associated with block 602 (or other display instructions) are configured to display the selected ones of the transducer graphical elements 502 (e.g., the transducer graphical elements 502 identified as "R:6", "Q:6", "P:6", "P:7", "O:7", "O:8", "O:9", "P:9", "P:10", "Q:10", "R:10", "R:9", "S:9", "S:8", "S:7", and "R:7") with a set of visual characteristics that that is different than a set of visual characteristics comprised by particular ones of the transducer graphical elements 502 corresponding to particular ones of the transducers that do not form part of the selected transducers in the distribution. In some embodiments, the display instructions associated with block 602 are configured to display the selected ones of the between graphical elements 504 (e.g., the between graphical elements 504 identified as "R:6-Q:6", "Q:6-P:6", "P:6-P:7", "P:7-O:7", "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6") with a set of visual characteristics (e.g., an interior color) that is different than a set of visual characteristics comprised by other particular ones of the between graphical elements (e.g., which are displayed with a different interior color). In some embodiments, a plurality of intra-cardiac electrograms 535 is also displayed, each of the intra-cardiac electrograms derived from intra-cardiac voltage data sampled by a respective one of the selected transducers in the distribution.

In some embodiments, the display instructions associated with block 602 (or other display instructions) are configured to cause the input-output device system (e.g., 120, 320) to cause the graphical representation 500 to display a map depicting a surface of a tissue wall of the bodily cavity, the surface interrupted by one or more openings or ports, concurrently with the displayed graphical elements 501 (e.g., displayed transducer graphical elements 502 and displayed between graphical elements 504 are displayed concurrently with regions 525c). In some embodiments, each of the one or more ports corresponds to a region 525c (described previously).

In some embodiments, the display instructions associated with block 602 (or other display instructions) are configured to display the particular transducer graphical elements 502 corresponding to the selected transducers in the distribution surrounding at least one of the one or more ports depicted in the map (e.g., a region 525c in some embodiments). In various embodiments, reception instructions may be included in a program, the reception instructions configured to cause reception, via the input-output device system (e.g., 120, 320), of information from each of a number of the plurality of transducers (e.g., each of the plurality of transducers 306), and the display instructions associated with block 602 may be configured to display the map based at least on the information received from each of the number of the plurality of transducers (e.g., by various methods the same or similar to those described above).

In some embodiments, the transducer activation instructions associated with block 608 may include instructions that are configured to cause a sensing device system (e.g., sensing device system 325) to detect a physiological parameter in the bodily cavity. Other forms of activation of the respective transducer corresponding to the selected transducer graphical element are possible in other embodiments. For example, in various embodiments, activation instructions configured to activate a particular transducer may include instructions configured to cause energy from a power source device system (e.g., power source device system 340) to be delivered to the particular transducer. In some embodiments, a sensing device system (e.g., provided at least in part by a number of the transducers) is arranged to sense at least one tissue electrical characteristic (e.g., tissue impedance) at a respective location at least proximate the respective transducer corresponding to the selected transducer graphical element with the energy delivered to the transducer (e.g., in some embodiments, tissue impedance may be measured between transducers on the structure 308 or between a transducer on the structure 308 and the indifferent electrode 326). In some of these various embodiments, the energy is sufficient for ablating tissue (e.g., tissue-ablating energy). In some of these various embodiments, an indifferent electrode (e.g., indifferent electrode 326) is provided (e.g., usually to an external surface or skin-based surface of a body) while the transducer-based device is received in a bodily cavity within the body. A significant or major portion of the tissue-ablating energy delivered to the respective transducer corresponding to the selected transducer graphical element may be transmitted from the respective transducer to the indifferent electrode in a process typically referred to as monopolar ablation.

Returning to FIG. 5E, there is represented a group of transducers surrounding a region 525c that are selected for activation. These selected transducers are represented in the graphical representation 500 in FIG. 5E by way of corresponding highlighted between graphical elements 504. With these selections, the instructions associated with block 608 are configured to cause the data processing device system (e.g., 110, 310) to execute a process of activating these selected transducers, according to some embodiments. However, due to hardware constraints (e.g., limitations on the power source device system 340) and safety constraints (e.g., limitations on delivered energy and energy density to prevent the formation of coagulum), activation of all of the selected transducers at the same time often is not possible or acceptable. Accordingly, the instructions associated with block 606 are configured, according to some embodiments, to cause the data processing device system (e.g., 110, 310) to break up these selected transducers into various subsets to be activated, at least in part, in series over time within the hardware constraints, safety constraints, or other constraints.

Figure 5F:
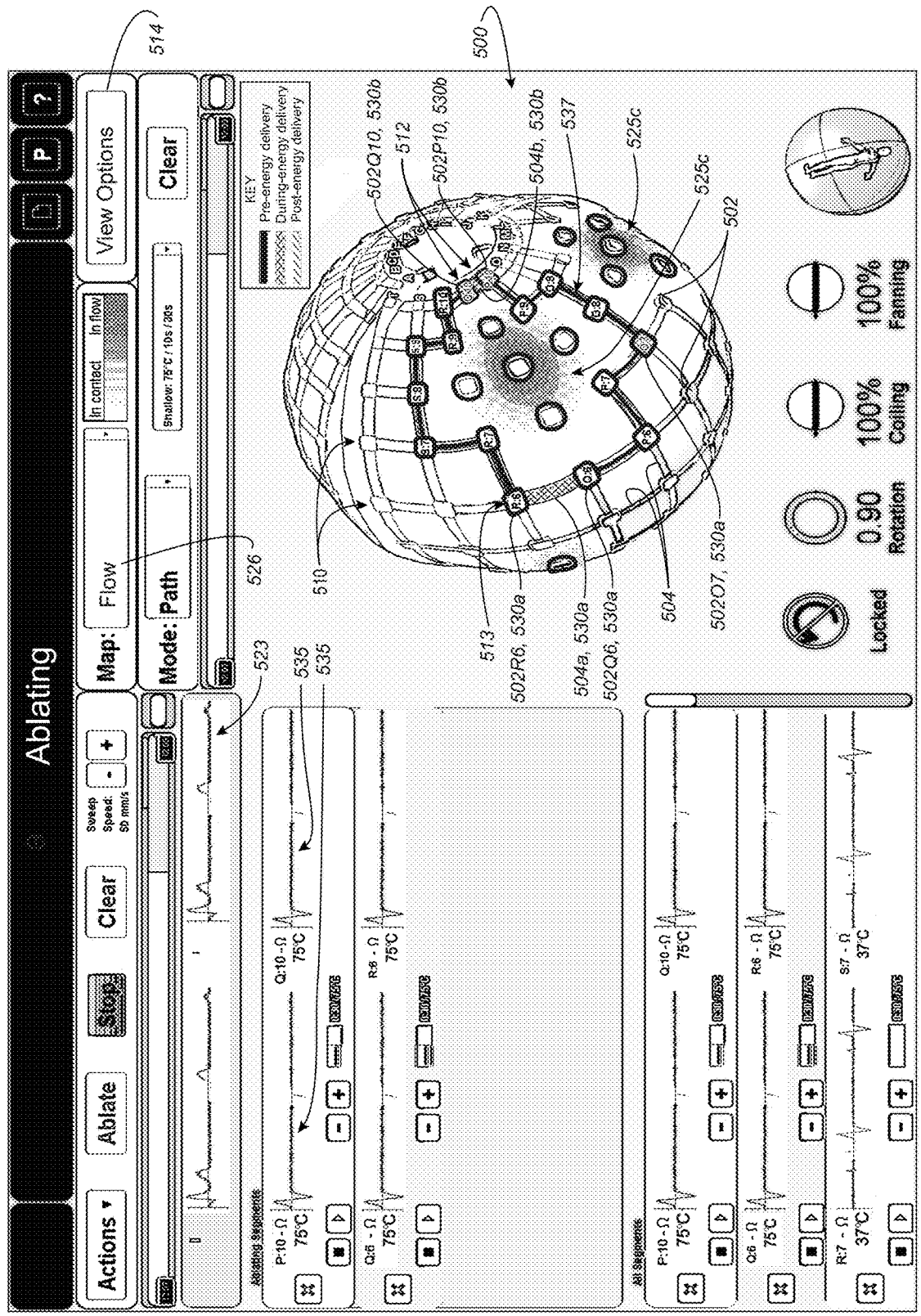
FIGS. 5F and 5G include the graphical representation of FIG. 5E associated with two successive activations of various transducer sets identified from a plurality of transducer graphical elements along the path, according to various example embodiments.
Figure 5G:
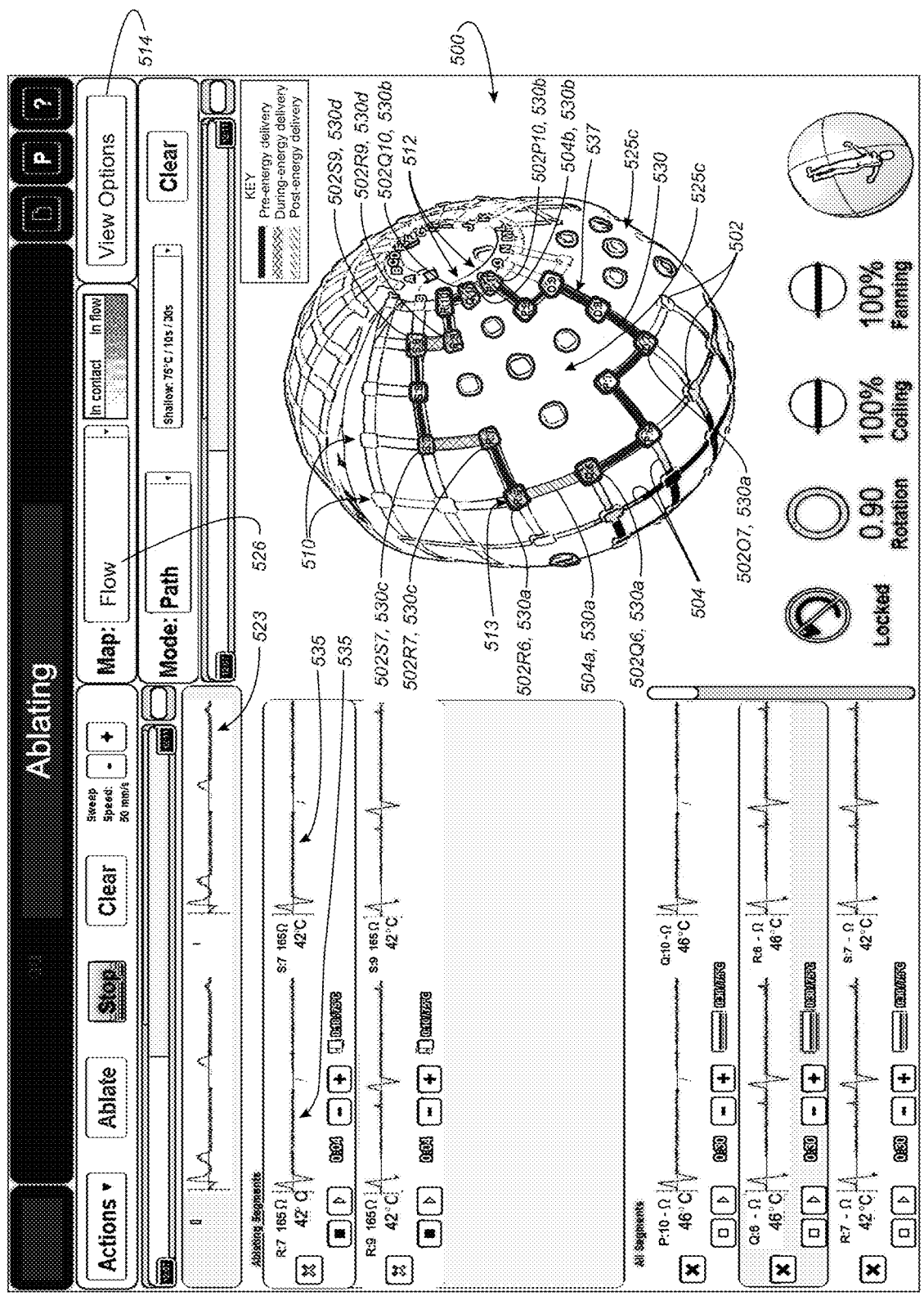
Figure 5H:
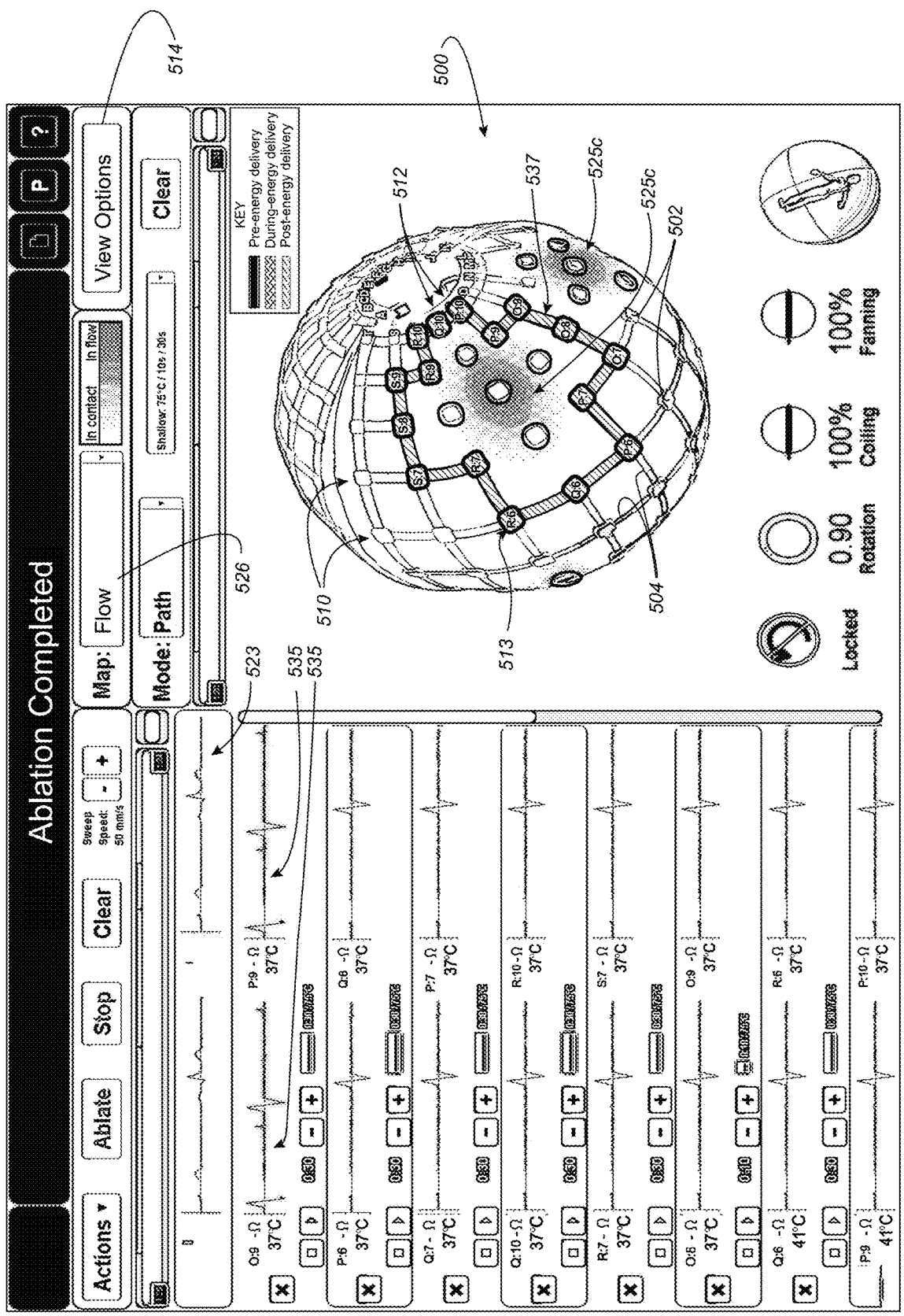
FIG. 5H includes the graphical representation of FIG. 5E after the completion of the activation of all the various transducer sets, according to various example embodiments.

For example, FIGS. 5F-5H show the transducers selected according to FIG. 5E being activated in a piece-meal manner over time, according to some embodiments. For instance, FIG. 5F shows a first set of transducers 530a and a second set of transducers 530b of the transducers selected according to FIG. 5E being activated (e.g., in a "during-energy delivery" state), followed by a third set of transducers 530c and a fourth set of transducers 530d being activated (e.g., in the "during-energy delivery" state) as shown in FIG. 5G. FIG. 5H shows a state where all of the transducers selected according to FIG. 5E have been activated (e.g., in a "post-energy delivery" state).

However, the present inventors have recognized potential issues associated with energy delivery characteristics that may limit various configurations of transducer sets that may be identified according to the instructions associated with block 606 for activation according to the instructions associated with block 608.

To elaborate, when energy is delivered from a power source device system to a respective set of two or more transducers (e.g., a group of the transducers) positioned in a bodily cavity, (a) a portion of the energy delivered to a first transducer of the respective set (e.g., first transducer 304a) is then transmitted by the first transducer, (b) a portion of the energy delivered to a second transducer of the respective set (e.g., second transducer 304b) is then transmitted by the second transducer, or both (a) or (b). In some embodiments, (a) a portion of the energy delivered to the first transducer is then transmitted by the first transducer to the second transducer, (b) a portion of the energy delivered to the second transducer is then transmitted by the second transducer to the first transducer, or both (a) or (b).

When the first and the second transducers are positioned sufficiently close to one another, a portion of the energy transmitted between the first and the second transducers may have energy levels sufficiently high to cause tissue ablation in a tissue region that spans respective tissue regions contacted by, or ablated by, the first and the second transducers in a process typically referred to as bipolar ablation. In some embodiments, an indifferent electrode (e.g., indifferent electrode 326) is provided (e.g., usually to an external surface or a skin-base surface of a body) while the transducer-based device (e.g., 200, 300) is received in a bodily cavity within the body. While some of the tissue-ablating energy is transmitted between the first and the second transducers, some of the tissue-ablating energy may be transmitted from either of the first and the second transducers to the indifferent electrode in a process typically referred to as blended or combined monopolar-bipolar ablation.

Bipolar ablation may be conducted in various manners. For example, in various radio-frequency (RF) bipolar ablation systems, different phased RF voltages are provided to respective ones of a pair of electrodes positioned in a bodily cavity to create a potential difference between the pair of electrodes (e.g., 315, 415) sufficient to allow for a flow of electric current between the pair of electrodes and effect RF bipolar ablation of tissue between the pair of electrodes. On the other hand, monopolar ablation may be caused, at least in part, by ensuring that there is not a sufficient potential difference between sufficiently close electrodes, so as to discourage or prevent the transfer of energy having levels sufficient to cause bipolar tissue ablation therebetween. In monopolar ablation, the potential difference that causes the transfer of tissue-ablative energy is between the intra-bodily-cavity electrode selected to cause tissue ablation and the indifferent electrode located outside the bodily cavity. A potential difference between the selected intra-bodily-cavity electrode and another intra-bodily-cavity electrode may be prevented in monopolar ablation by ensuring that the two intra-bodily-cavity electrodes have a same phase (e.g., phase angle), a same amplitude, or both a same phase and amplitude. Blended monopolar-bipolar ablation may be performed by ensuring at least that there is both a sufficient potential difference to cause tissue ablation between (a) a first intra-bodily-cavity electrode and the indifferent electrode, and (b) the first intra-bodily-cavity electrode and a second intra-bodily-cavity electrode. Such potential differences may be caused, at least in part, by having the indifferent electrode, the first intra-bodily-cavity electrode, and the second intra-bodily-cavity electrode at three different phases. However, other techniques for causing a potential difference may be employed, as discussed below. In addition to potential difference causing tissue ablation, other factors are present, such as the distance between the electrodes, the size and dimensions of the electrodes, and the delivered energy amount and density.

Typically, monopolar ablation results in the formation of deeper ablated regions (e.g., also referred to as lesions) than ablated regions formed by bipolar ablation and are generally preferred since the formed lesions have a higher likelihood of being transmural and thus generally are better suited to block cardiac electrical signals in atrial fibrillation treatment procedures. Additionally, in cardiac bipolar ablation procedures, regions of relatively high current densities associated with the flow of current between a pair of transducers (e.g., a pair of electrodes) may cause thermally induced coagulum in the blood since these regions are typically close to the tissue surface that is in contact with the blood. In monopolar ablation procedures, the relatively high-current density region is typically shielded by the electrode from the blood-contacting tissue surface. The generation of thermal coagulum may, in some cases, lead to various undesired conditions such as stroke. For these and other reasons, the activation of a pair of transducers spaced sufficiently close to one another to allow for the formation of an ablated tissue region that spans or bridges the pair of transducers activated as per conventional bipolar tissue ablation techniques may not always be desirable.

In addition, it generally is desirable to concurrently activate as many of the selected transducers (e.g., FIG. 5E) as safely as possible to reduce procedure times. Typically, in ablation procedures, as discussed above, a potential difference is required between transducers or electrodes to facilitate the transfer of the tissue ablative current therebetween. For example, in monopolar ablation procedures, a suitable potential difference is required between one of the transducers (e.g., 220, 306, and 406) and an indifferent electrode (e.g., 326). Likewise, in bipolar ablation procedures, a suitable potential difference is required between two of the transducers (e.g., 220, 306, and 406). These potential differences may be achieved in various ways including manipulation of an electrical property (e.g., a current or a voltage) of a transmission of power between a power source device system and each of the transducers. For example, a potential difference may be achieved by (a) amplitude differences between various ones of the electrical property (e.g., current or voltage) signals (b) frequency differences between various ones of the electrical property signals; (c) phase angle changes between various ones of the electrical property signals, or any combination of (a), (b) and (c) by way of non-limiting examples.

It is noted that power is the product of the voltage and current (for example as measured at the transducer or further upstream or downstream from the transducer). Typically, in RF tissue ablation systems, the RF power source device system (e.g., power source device system 340 in some embodiments) includes various amplifiers that are designed to either be voltage mode amplifiers or current mode amplifiers. When a voltage mode amplifier is employed, the amplifier will attempt to maintain the output voltage at the commanded level. In some of these embodiments, the commanded level is typically specified as both a voltage magnitude and phase angle, and the resulting current delivered by the amplifier will depend on the impedance of the load attached to the amplifier. In some embodiments where a current mode amplifier is employed, the amplifier will attempt to maintain the output current at the commanded level. In this particular case, the commanded level is specified as both a current magnitude and phase angle. The resulting voltage delivered by the amplifier will depend on the impedance of the load attached to the amplifier.

When electrode-based transducer systems are employed in RF tissue ablation applications, heating at least proximate any one of the electrodes (e.g., 315, 415) is proportional to the square of the current driven through the electrode. The current is caused by a potential difference (also referred to as a voltage difference) that is generated between the electrode and the surrounding tissue. As a result of the applied potentials at the electrodes, the tissue proximate each of the electrodes takes on a potential or voltage between the electrode potential and the voltage of a return electrode (e.g., indifferent electrode 326), the tissue acting as a voltage divider. If the transducer-based ablation system is restricted to supply the transmitted power to the electrodes on the basis of the electrical property (e.g., a current or voltage) of the transmitted power having a single phase, then the voltage of the tissue portions near the electrodes will be significantly higher than the voltage at the return electrode (e.g., indifferent electrode 326) as compared with a situation in which the electrical property of the transmitted power has multiple phase angles. If the transducer-based ablation system operated with the power transmitted to some of the electrodes with an electrical property at one phase angle while the power transmitted to other ones of the electrodes with the electrical property having another phase angle sufficient to create a suitable phase difference (e.g., a phase lead or lag of approximately 180 degrees), then the voltage of tissue portions near the electrodes will stay at a relatively lower voltage as compared with the voltage at the return electrode (e.g., indifferent electrode 326). In this case, the voltage present at each of the electrodes is also lower than the case where the system is restricted to operating at a single phase. The lower operating voltage advantageously allows for a more cost effective power supply system, and allows for lower dielectric strength for various insulators associated with the cabling and other components of the transducer-based device. Accordingly, in some embodiments, a multi-phase transducer-based tissue ablation system (e.g., transducer-based device system 300 and power source device system 340 thereof in some embodiments) that provides the advantages described above but mitigates potentially harmful conditions (e.g., thermally induced coagulum) associated with conventional bipolar ablation techniques is employed.

In view of the above discussion, the present inventors have recognized that, in some circumstances, it may be beneficial to utilize a multi-phase transducer-based tissue ablation system while generally avoiding bipolar tissue ablation when activating transducers selected for ablation (e.g., FIG. 5E). While these constraints are not required by various embodiments, they may be beneficial in some circumstances.

In this regard, in some embodiments, the instructions associated with block 606 and block 608 are configured to identify two sets (e.g., a pair of subsets) of the transducers selected for activation (e.g., FIG. 5E) and then, at least in part, simultaneously activate those two sets (e.g., FIG. 5F), such that the two sets have different phase angle ranges to achieve at least a benefit of lower operating voltage of a multi-phased system. In addition, in some embodiments, the two sets are identified according to the instructions associated with block 606 such that no transducers between the two sets are sufficiently close to cause a confluence of ablated tissue regions therebetween or, in some embodiments, to avoid bipolar tissue ablation therebetween to avoid the potential drawbacks of bipolar tissue ablation discussed above. In some embodiments, the two sets are activated according to the instructions associated with block 608 not only simultaneously with each other, but activation of the transducers in each of the two sets is also executed simultaneously, although variations on these simultaneous occurrences may exist, as discussed in more detail below. Depending upon the number, arrangement, or both, of the transducers selected for activation, one or more subsequent pairs of identified sets (e.g., subsets) of the transducers selected for activation are activated (e.g., FIG. 5G), according to some embodiments. In other words, the process of identifying and activating pairs of the sets of the transducers selected for activation iterates until all of the transducers selected for activation have been activated (e.g., FIG. 5H), according to some embodiments.

In this regard, in some embodiments, identification instructions associated with block 606 may be configured to identify a plurality of transducer sets from at least some of the transducers in the distribution selected in accordance with the selection instructions associated with block 604 (e.g., FIG. 5E). In various embodiments, the plurality of transducer sets identified according to the instructions associated with block 606 include at least a first transducer set and a second transducer set from the selected transducers in the distribution. In various embodiments, each of the transducer sets includes at least one transducer of the selected transducers in the distribution. In various embodiments, each of the transducer sets includes at least two transducers of the selected transducers in the distribution. In various embodiments, each of the transducer sets includes at least one transducer that is different from a transducer included in another of the transducer sets. In FIG. 6, the first transducer set is identified via the instructions associated with block 606*a*, and the second transducer set is identified via the instructions associated with block 606*b*, according to some embodiments.

In various embodiments, activation instructions associated with block 608 include first transmission instructions (e.g., indicted by block 608*a* in FIG. 6) configured to cause a first transmission of power between a power source device system (e.g., 340) and each transducer in the first transducer set, the first transmission of power including an electrical property that includes at least one phase angle in a first range of phase angles, the electrical property being a current or a voltage. The activation instructions may also include second transmission instructions (e.g., indicted by block 608b in FIG. 6) configured to cause a second transmission of power between a power source device system (e.g., 340) and each transducer in the second transducer set, the second transmission of power including the electrical property and including at least one phase angle in a second range of phase angles. In some embodiments, the first range of phase angles and the second range of phase angles do not overlap. For example, in some embodiments, the first transmission of power to the transducers in the first transducer set may have or may have about a zero degree phase angle, while the second transmission of power to the transducers in the second transducer set may have or may have about a 180 degree phase angle. However, other phase angle configurations may exist in other embodiments. In various embodiments, the first transmission of power occurs simultaneously with the second transmission of power at least in part over a time interval (a) during the reception of the transducer selection associated with block 604, (b) after a completion of the transducer selection, or both (a) and (b).

For example, in FIG. 5F, various graphical elements 501 corresponding to each of a first transducer set 530a and a second transducer set 530b have been identified according to the instructions associated with blocks 606a, 606b respectively from the various highlighted graphical elements 501 shown in FIG. 5E surrounding region 525c, which were selected according to the instructions associated with block 604, according to some embodiments. It should be noted that, although the first transducer set 530a and the second transducer set 530b are shown as including particular graphical elements 501 (e.g., 502, 504) in FIG. 5F as a representation to the user, the first transducer set 530a and the second transducer set 530b include the transducers (e.g., 220, 306, and 406) corresponding to the respective particular graphical elements 501.

In some embodiments, the first transducer set 530a includes three transducers indicated in the graphical interface by the transducer graphical elements 502R6, 502Q6, and 502O7 whose respective identifiers 513 are indicated as "R:6", "Q:6", and "O:7", and the second transducer set 530b includes two transducers indicated by the transducer graphical elements 502P10, and 502Q10 whose respective identifiers 513 are indicated as "P:10" and "Q:10". In some embodiments, the transducer graphical elements 502R6 and 502Q6 may have been identified by a user's selection of a respective between graphical element 504a, the transducer graphical element 502O7 may have been identified by a user's direct selection of the respective transducer graphical element 502, and the transducer graphical elements 502P10 and 502Q10 may have been identified by a user's selection of a respective between graphical element 504b. However, in other embodiments, any other forms of selection of such transducer graphical elements may be implemented.

As per the "KEY" provided in FIG. 5F (also provided in FIGS. 5G and 5H) each of the transducers associated with transducer graphical elements 502R6, 502Q6, and 502O7 in the first transducer set 530a and the transducers associated with transducer graphical elements 502P10 and 502Q10 in the second transducer set 530b includes a visual characteristic as per the "KEY" indicating that energy delivery is occurring during the simultaneous activation of the respective transducers in the first transducer set 530a and the second transducer set 530b. Specifically, in some embodiments, the transducers in the first transducer set 530a may be activated in accordance with first transmission instructions associated with block 608a (e.g., a sub-block of block 608) which are configured to cause a first transmission of power between an RF power source device system (e.g., one example embodiment of power source device system 340) and each transducer in the first transducer set 530a. In some embodiments, the transducers in the second transducer set 530b may be activated in accordance with second transmission instructions associated with block 608b (e.g., a sub-block of block 608) which are configured to cause a second transmission of power between an RF power source device system (e.g., one example embodiment of power source device system 340) and each transducer in the second transducer set 530b. In some embodiments, the first transmission of power is occurring simultaneously with the second transmission of power.

It is noted that, in some embodiments, between graphical element 504a is also identified by the identification instructions associated with block 606a, and the between graphical element 504b is also identified by the identification instructions associated with block 606b. Such identification of a between graphical element 504 may be motivated for various reasons. For example, in some embodiments, an indirect selection of various transducer graphical elements 502 via a direct selection of a between graphical element 504 as described above with respect to the instructions associated with block 604 may continue to be indicated to the user when the specific transducer sets (e.g., 530a, 530b) are identified in accordance with the instructions associated with block 606. In FIG. 5F, the transducer graphical elements 502R6 and 502Q6 identified as associated with the first transducer set 530a may have originally been indirectly selected via the instructions associated with block 604 by a selection of between graphical element 504a, while the transducer graphical element 502O7 associated with the first transducer set 530a may have been selected directly via the instructions associated with block 604, according to some embodiments. In some embodiments, transducer graphical elements 502 that are indirectly selected via a between graphical element 504 may be identified according to the instructions associated with block 608 as being associated with corresponding transducers that are to be activated together or simultaneously. It is noted, in some embodiments, that the selection of various transducers and the identification of various ones thereof for inclusion in a particular one of the plurality of transducer sets may occur in different manners, and other forms of depiction of the selected transducers or other forms of depiction of the identification of various ones of the selected transducers for inclusion in a particular one of the transducer sets may be displayed. In some embodiments, the reception of the selected at least some of the transducers in the distribution via the instructions associated with block 604 include reception of a user-based selection, via the input-output device system, of the selected at least some of the transducers in the distribution, and the identification instructions associated with block 606 are configured to identify the plurality of transducer sets from the selected at least some of the transducers in the distribution include machine-based identification of the plurality of transducer sets from the selected at least some of the transducers in the distribution.

It is noted that the KEY shown in FIGS. 5F, 5G and 5H is provided for the convenience of discussion and may not form part of the graphical interface in various embodiments.

In some embodiments, each transducer included in the first transducer set 530a and each transducer included in the second transducer set 530*b* is operable to form a respective ablated tissue region (e.g., also referred to as a lesion) in response to transmission of a respective one of the first transmission of power and the second transmission of power. In some embodiments, the identification instructions associated with block 606 are configured to at least prevent the first transducer set 530*a* from including a particular transducer in the selected at least some of the transducers in the distribution (e.g., indicated in FIG. 5E) that is sufficiently close to any respective transducer in the distribution that is included in the second transducer set 530*b* to cause a confluence of respective ablated tissue regions therebetween if the first transmission of power was to be transmitted between the RF power source device system and the particular transducer simultaneously with the second transmission of power between the RF power source device system and the respective transducer included in the second transducer set 530*b*.

For example, in some embodiments, if the first transmission of power to the first transducer set (e.g., 530*a*) is at or at about zero degrees in phase, and the second transmission of power to the second transducer set (e.g., 530*b*) is at or at about 180 degrees in phase, the instructions associated with block 606 may be configured to ensure that there is no transducer in the first transducer set that would cause bipolar tissue ablation with a transducer in the second transducer set (or vice versa) when the first and second transmissions of power occur simultaneously (e.g., FIG. 5F). In some embodiments, to facilitate determining whether any transducer would cause such bipolar tissue ablation (or, more generally, a confluence of ablated tissue) with an electrode in the opposite transducer set, the instructions associated with block 606 may be configured to access predetermined information from a memory device system (e.g., 130, 330) that define transducer electrode size, tissue (e.g., intracardiac tissue) conductivity information, inter-transducer electrode distances, whether transducer electrodes are separated by a region of space not including any physical part of the transducer-based device (e.g., 200, 300) or along an elongate member (e.g., 304), energy delivery characteristics to the respective electrodes (e.g., voltage, current, density), or all or a combination of some of these items. With such predetermined information, a threshold minimum distance between any transducer in the first transducer set (e.g., 530*a*) and any transducer in the second transducer set (e.g., 530*b*) may be determined to prevent ablated-tissue-region-confluence, and, accordingly, the instructions associated with block 606 may be configured to identify the respective first and second sets of transducers at least by ensuring that no transducer in the first set is within this minimum distance from a transducer in the second set and vice versa. In some embodiments, the threshold minimum distance requires a one-transducer gap, such that the instructions associated with block 606 are configured to ensure that each particular transducer in the first transducer set (e.g., 530*a*) has at least one transducer between it and every transducer in the second transducer set (e.g., 530*b*) and vice versa (e.g., that each particular transducer in the second transducer set 530*b* has at least one transducer between it and every transducer in the first transducer set 530*a*). In some embodiments, the at least one transducer is not activated during (a) an activation of at least the particular transducer, (b) an activation of at least each of the every transducer, (c) both (a) and (b), or (d) during at least a simultaneous activation of the transducers in the first transducer set (e.g., 530*a*) and the second transducer set (e.g., 530*b*).

In some embodiments, the instructions associated with block 606 may include additional rules for identifying the first and second sets of transducers (e.g., 530*a*, 530*b*), such as a maximum number of transducers that may be included in a transducer set due to hardware constraints, preventing a transducer set from including a series of transducers that form a 90 degree angle (as heat may be entrapped in a 90 degree corner, thereby increasing the risk of generating coagulum (e.g., thermally induced or otherwise)), or other rules.

In embodiments encompassing FIG. 5F, each of the transducers included in the first transducer set 530*a* is identified in accordance with the instructions associated with block 606*a* not to include any of the selected transducers shown in FIG. 5E that is sufficiently close to any respective transducer included in the second transducer set 530*b* (e.g., any of the transducers corresponding to the transducer graphical elements 502P10 and 502Q10 in FIG. 5F) to cause a confluence of respective ablated tissue regions therebetween if the first transmission of power was to be transmitted between the RF power source device system (e.g., 340) and the particular transducer simultaneously or concurrently with the second transmission of power between the RF power source device system and the respective transducer included in the second transducer set 530*b*. Specifically, in some embodiments, only transducers corresponding to the transducer graphical elements 502Q6, 502R6, and 502O7 have been identified by the instructions associated with block 606*a* for inclusion in the first transducer set 530*a*, each of these transducer sufficiently distant from any of the transducers in the second transducer set 530*b* (e.g., any of the transducers corresponding to the transducer graphical elements 502P10 and 502Q10) to avoid a confluence or merging of respective ablated tissue regions therebetween. In this regard, any of the respective ablated tissue regions formed by the transducers in the first transducer set 530*a* (e.g., transducers corresponding to the transducer graphical elements 502Q6, 502R6, and 502O7) will not merge with any of the respective ablated tissue regions formed by transducers in the second transducer set 530*b* (e.g., transducers corresponding to the transducer graphical elements 502P10 and 502Q10) during the simultaneous occurrence of the first transmission of power and the second transmission of power. That is, the identification instructions associated with block 606 may be configured to identify each respective transducer in each of the first transducer set 530*a* and the second transducer set 530*b* as a particular one of the selected transducers (e.g., shown in highlight around a region 525*c* in FIG. 5F) in the distribution, the identified particular ones of the selected transducers arranged in the distribution to prevent a confluence of an ablated tissue region formed by any transducer included in the first transducer set 530*a* and an ablated tissue region formed by any transducer included in the second transducer set 530*b* from forming during the simultaneous occurrence of the first transmission of power and the second transmission of power.

It is noted that, in some embodiments, a confluence of two ablated tissue regions may include various characteristics (e.g., the two ablated tissue regions merged together without any interruptions therebetween and having sufficient depth to fully penetrate an underlying tissue wall (e.g., transmural)) that allow the two ablated tissue regions and their confluence to block electrical signals propagating through the tissue, such as in the treatment of atrial fibrillation.

In some embodiments, the electrical property of the first transmission of power transmitted between the RF power source device system (e.g., 340) and at least a first transducer (e.g., a transducer corresponding to any of the transducer graphical elements 502Q6, 502R6, and 502O7) in the first transducer set 530*a* includes a first particular phase angle of the at least one phase angle in the first range of phase angles, and the electrical property of the second transmission of power transmitted between the RF power source device system and at least a second transducer (e.g., a transducer corresponding to any of the transducer graphical elements 502P10 and 502Q10) in the second transducer set 530*b* includes a second particular phase angle of the at least one phase angle in the second range of phase angles. In some embodiments, a phase difference (e.g., either a phase lag or a phase lead) between the first particular phase angle and the second particular phase angle is 180 degrees. It is noted that the phase value of 180 degrees may be a nominal value in some embodiments and may deviate in some minor manner (e.g., +/−10 degrees) due to (1) reactive components in the system, (2) parasitic effects in the system, or both (1) and (2). In some embodiments, a phase difference (e.g., either a phase lag or a phase lead) between the first particular phase angle and the second particular phase angle may be between 10 degrees and 180 degrees.

It is noted that unlike conventional bipolar ablation techniques in which a current or voltage comprising a phase difference (e.g., a phase lag of up to 180 degrees, or a phase lead of up to 180 degrees) is associated with power transmission to a pair of relatively closely spaced transducers to create a potential difference therebetween that allows an ablated tissue region that spans or connects in an uninterrupted fashion tissue portions contacted by, or ablated by, the transducers, each of the transducers in the first transducer set 530*a* and each of the transducers in the second transducer set 530*b* is identified in accordance with the instructions associated with block 606 such that each transducer in the first set 530*a* is positioned sufficiently distant from any transducer identified for inclusion in the second set 530*b* to avoid a confluence or merging of the respective ablated tissue regions that are formed during the simultaneous occurrence of the first transmission of power whose electrical property includes at least one phase angle in a first range of phase angles and the second transmission of power having the same electrical property, but which includes at least one phase angle in a second range of phase angles that does not overlap the first range of phase angles. It is noted that the phase difference between the first particular phase angle and the second particular phase angle described above may, in some embodiments, be sufficient to create a potential difference between the first transducer in the first transducer set 530*a* and the second transducer in the second transducer set 530*b* that would be sufficient to cause a connecting or bridging lesion to form therebetween by way of bipolar tissue ablation during the simultaneous occurrence of the first transmission of power and the second transmission of power should the first and the second transducer be positioned sufficiently close to one another. However, in these embodiments, the identification instructions associated with block 606 prevent the first transducer and the second transducer from being identified as any particular ones of the selected transducers that are sufficiently spaced close enough with respect to one another for this to occur.

Accordingly, in some embodiments where a particular transducer is considered for inclusion in the first transducer set 530*a*, the identification instructions associated with block 606*a* may be configured to determine, for each respective transducer included in the second transducer set 530*b*, a particular respective distance from the respective transducer included in the second transducer set 530*b* that the particular transducer is distanced from. The identification instructions associated with block 606*a* may be configured to at least prevent the first transducer set 530*a* from including the particular transducer, if it is determined according to the identification instructions that a confluence of an ablated tissue region formed by the particular transducer and an ablated tissue region formed by the respective transducer included in the second transducer set 530*b* would, if the first transmission of power was to be transmitted between the RF power source device system (e.g., 340) and the particular transducer simultaneously with the second transmission of power between the RF power source device system and the respective transducer included in the second transducer set 530*b*, occur due at least to the particular respective distance (e.g., it is within the above-discussed threshold minimum distance) and a particular phase difference. The particular phase difference may be between (1) a first particular phase angle of the at least one angle in the first range of phase angles that would be transmitted according to the first transmission of power between the RF power source device system and the particular transducer if the particular transducer was included in the first transducer set 530*a*, and (2) a second particular phase angle of the at least one phase angle in the second range of phase angles to be transmitted according to the second transmission of power between the RF power source device system and the respective transducer included in the second transducer set 530*b*. In various embodiments, the identification instructions associated with block 606*a* are configured to cause the first transducer set 530*a* to include only transducers in the selected at least some of the transducers in the distribution that each are sufficiently distant from each respective transducer in the distribution included in the second transducer set 530*b* to not cause a confluence of ablated tissue regions formed by any transducer in the first transducer set 530*a* and any transducer in the second transducer set 530*b* during the simultaneous occurrence of the first transmission of power and the second transmission of power.

It should be noted that some embodiments refer to the first transmission of power to the first transducer set as including a first range of phase angles, and the second transmission of power to the second transducer set as including a second range of phase angles not overlapping the first range of phase angles. The non-overlapping of the first and second ranges of phase angles, in some embodiments, may be caused by the instructions associated with block 608 causing the power source device system (e.g., 340) to deliver opposite phase angles (e.g., phase angles opposite to one another within 360 degrees such as 0 degrees and 180 degrees or 90 degrees and 270 degrees, or 360 degrees and 540 degrees, etc.) or otherwise different phase angles to the first and second transducer sets respectively. It is noted in various embodiments employing periodic signals, phase angle values of greater than 360 degrees are considered equivalent to corresponding phase angle values under 360 degrees. For example, a phase angle value of 540 degrees is considered equivalent to a phase angle value of 180 degrees in various embodiments.

The presence of a first range of phase angles and the second range of phase angles being delivered to the first and second transducer sets, respectively, may be caused by variability (e.g., a phase angle delivery tolerance) of the power source device system (e.g., 340). For example, the instructions associated with block 608 may be configured to cause the power source device system (e.g., 340) to deliver a phase angle of zero degrees to the first transducer set (e.g., 530a), but, within the tolerance of the power source device system (e.g., 340), one transducer in the first transducer set may receive a phase angle of zero degrees and another transducer in the first transducer set may receive a phase angle of two degrees, such that the first range of phase angles associated with the first transmission of power is between zero degrees and two degrees, inclusive. It is also noted that the specific impedance provided by the body comprising the cavity into which the transducers are deployed (e.g., the patient) may result in different loading on the output of an amplifier of the power source device system (e.g., 340) and thereby contribute to different phases described above.

In some embodiments, the presence of the first range of phase angles and the second range of phase angles being delivered to the first and second transducer sets, respectively, may be caused by design of the instructions associated with block 606, 608, or both. For example, while the first and second transducer sets 530a, 530b may have different phase angle ranges between them that would cause bipolar tissue ablation (if a transducer in the first transducer set and a transducer in the second transducer set were sufficiently close), it may be desired, in some embodiments, that transducers within a given set cause a form of blended bipolar-monopolar ablation between them. For example, in some embodiments, the transducer associated with transducer graphical element 502R6 in the first transducer set 530a in FIG. 5F may receive a phase angle of zero degrees according to the instructions associated with block 608a, and the transducer associated with transducer graphical element 502Q6 in the first transducer set 530a in FIG. 5F may receive a phase angle of 60 degrees according to the instructions associated with block 608a. In addition, in some embodiments, the transducer associated with transducer graphical element 502Q10 in the second transducer set 530b in FIG. 5F may receive a phase angle of 180 degrees according to the instructions associated with block 608b, and the transducer associated with transducer graphical element 502P10 in the second transducer set 530b in FIG. 5F may receive a phase angle of 240 degrees according to the instructions associated with block 608b. In this example, according to some embodiments, the first range of phase angles delivered to the first transducer set 530a according to the instructions associated with block 608a may be from zero degrees to 60 degrees, inclusive, and the second range of phase angles delivered to the second transducer set 530b according to the instructions associated with block 608b may be from 180 degrees to 240 degrees, inclusive.

In this regard, it is noted that, in some embodiments, the first transmission of power comprising an electrical property (e.g., current or voltage) that includes at least one phase angle in the first range of phase angles may include at least two phase angles, and the second transmission of power comprising the electrical property that includes at least one phase angle in the second range of phase angles that does not overlap the first range may include at least two phase angles. For example, in some embodiments, the first transducer set 530a includes a first transducer of the selected at least some of the transducers in the distribution (e.g., a transducer corresponding to the transducer graphical element 502Q6 in FIG. 5F) and another transducer of the selected at least some of the transducers in the distribution (e.g., a transducer corresponding to either of the transducer graphical elements 502R6 or 502O7 in FIG. 5F). The electrical property of the first transmission of power transmitted between the RF power source device system and the first transducer included in the first transducer set 530a may include a first phase angle of the at least one phase angle in the first range of phase angles, and the electrical property of the first transmission of power transmitted between the RF power source device system and the another transducer included in the first transducer set may include another phase angle of the at least one phase angle in the first range of phase angles different than the first phase angle. A difference between the respective electric potentials of the first transducer and the another transducer included in the first transducer set 530a may correspond to, at least in part, a phase difference between the first phase angle and the another phase angle in the first range of phase angles. In some embodiments, the second transducer set 530b may include a second transducer of the selected at least some of the transducers in the distribution and another transducer of the selected at least some of the transducers in the distribution (e.g., the transducers corresponding to the transducer graphical elements 502P10 and 502Q10). The electrical property of the second transmission of power transmitted between the RF power source device system (e.g., 340) and the second transducer included in the second transducer set 530b includes a second phase angle of the at least one phase angle in the second range of phase angles, and the electrical property of the second transmission of power transmitted between the RF power source device system and the another transducer included in the second transducer set includes another phase angle of the at least one phase angle in the second range of phase angles different than the second phase angle. A difference between the respective electric potentials of the second transducer and the another transducer included in the second transducer set 530b may correspond to, at least in part, a phase difference between the second phase angle and the another phase angle in the second range of phase angles. In various embodiments, each transducer included in the first transducer set 530a is different than each transducer included in the second transducer set 530b.

In some embodiments, the phase angle delivered to a transducer in a set according to the instructions associated with block 608 may change or modulate during activation (e.g., delivery of tissue-ablative energy) in isolation or in an opposing manner with an another (e.g., an adjacent) transducer in the same set to form what may be preferable tissue-ablation characteristics in some circumstances. For example, in some embodiments, the transducer associated with transducer graphical element 502O7 in the first transducer set 530a in FIG. 5F may receive a phase angle that modulates between zero degrees and 60 degrees according to the instructions associated with block 608a during the activation shown in FIG. 5F. For another example, in some embodiments, the transducer associated with transducer graphical element 502R6 in the first transducer set 530a in FIG. 5F may receive a phase angle that modulates between zero degrees and 60 degrees according to the instructions associated with block 608a during the activation shown in FIG. 5F, while the transducer associated with transducer graphical element 502Q6 in the first transducer set 530a in FIG. 5F may receive a phase angle that opposingly modulates between 60 degrees and zero degrees according to the instructions associated with block 608a during the activation shown in FIG. 5F.

In this regard, in some embodiments, (1) the electrical property of the first transmission of power between the RF power source device system (e.g., 340) and a first transducer included in the first transducer set 530a (e.g., a transducer corresponding to any of the transducer graphical elements 502Q6, 502R6, or 502O7 in FIG. 5F) includes a first portion including a first phase angle of the at least one phase angle in the first range of phase angles and a second portion including a second phase angle of the at least one phase angle in the first range of phase angles different than the first phase angle in the first range of phase angles; (2) the electrical property of the second transmission of power between the RF power source device system (e.g., 340) and a second transducer included in the second transducer set 530*b* (e.g., a transducer corresponding to any of the transducer graphical elements 502P10 and 502Q10 in FIG. 5F) includes a first portion including a first phase angle of the at least one phase angle in the second range of phase angles and a second portion including a second phase angle of the at least one phase angle in the second range of phase angles different than the first phase angle in the second range of phase angles; or both (1) and (2).

In some embodiments, (1) the first transmission instructions associated with block 608*a* are configured to cause the electrical property of the first transmission of power between the RF power source device system (e.g., 340) and each of at least a first transducer included in the first transducer set 530*a* (e.g., a transducer corresponding to any of the transducer graphical elements 502Q6, 502R6, and 502O7 in FIG. 5F) to modulate between a first phase angle of the at least one phase angle in the first range of phase angles and a second phase angle of the at least one phase angle in the first range of phase angles different than the first phase angle in the first range of phase angles; (2) the second transmission instructions associated with block 608*b* are configured to cause the electrical property of the second transmission of power between the RF power source device system and each of at least a second transducer included in the second transducer set 530*b* (e.g., a transducer corresponding to any of the transducer graphical elements 502P10 and 502Q10 in FIG. 5F) to modulate between a first phase angle of the at least one phase angle in the second range of phase angles and a second phase angle of the at least one phase angle in the second range of phase angles different than the first phase angle in the second range of phase angles; or both (1) and (2).

As discussed above, in some embodiments, the power transmitted to the first transducer set (e.g., 530*a*) and the power transmitted to the second transducer set (e.g., 530*b*) according to the instructions associated with block 608 may occur, at least in part, simultaneously or concurrently. In addition, in some embodiments, the power transmitted to some or all of the transducers in the first transducer set (e.g., 530*a*) may occur simultaneously or concurrently, and the power transmitted to some or all of the transducers in the second transducer set (e.g., 530*b*) may occur simultaneously or concurrently, according to the instructions associated with blocks 608*a* and 608*b*, respectively.

To elaborate, in some embodiments, it is noted that the second transducer set 530*b* may be activated in the same manner or in a similar manner that the first transducer set 530*a* is activated as described above, especially in some embodiments in which the second transducer set 530*b* is identified by the instructions associated with block 606*b* as including at least two transducers (e.g., as shown in FIG. 5F). In some embodiments in which each of the first transducer set 530*a* and the second transducer set 530*b* includes two or more of the selected transducers (e.g., FIG. 5E), the first transmission instructions associated with block 608*a* may be configured to cause simultaneous transmission of a first transmission of power between the RF power source device system (e.g., 340) and each respective one of the transducers in the first transducer set 530*a*, the first transmission of power between the RF power source device system (e.g., 340) and each respective one of the transducers including an electrical property including a respective phase angle in a first range of phase angles, the electrical property being a current or a voltage. The second transmission instructions associated with block 608*b* may be configured to cause simultaneous transmission of a second transmission of power between the RF power source device system and each respective one of the transducers in the second transducer set 530*b*, the second transmission of power between the RF power source device system (e.g., 340) and each respective one of the transducers including the electrical property including a respective phase angle in a second range of phase angles, the second range of phase angles not overlapping the first range of phase angles. Each transducer included in the first transducer set 530*a* and each transducer included in the second transducer set 530*b* may be operable to form a respective ablated tissue region in response to transmission of a respective one of the first transmission of power and the second transmission of power. Each of the first transmission of power and the second transmission of power may occur simultaneously at least in part over a time interval (a) during the reception of the selection, (b) after a completion of the reception of the selection, or both (a) and (b).

In some embodiments, no transmission of any power comprising the electrical property (e.g., current of voltage) including at least one phase angle in the first range of phase angles between the RF power source device system (e.g., 340) and any of the plurality of transducers (e.g., 220, 306, 406) not included in the first transducer set 530*a* occurs during the simultaneous occurrence of the first transmission of power and the second transmission of power, and no transmission of any power comprising the electrical property including at least one phase angle in the second range of phase angles between the RF power source device system and any of the plurality of transducers not included in the second transducer set 530*b* occurs during the simultaneous occurrence of the first transmission of power and the second transmission of power. In some embodiments, the first transmission of power is delivered only between the RF power source device system and each transducer in the first transducer set 530*a* during the simultaneous occurrence of the first transmission of power and the second transmission of power, and the second transmission of power is delivered only between the RF power source device system and each transducer in the second transducer set 530*b* during the simultaneous occurrence of the first transmission of power and the second transmission of power.

In various embodiments in which the first transducer set 530*a* or the second transducer set 530*b* includes at least two transducers, the respective one of the first transmission of power and the second transmission of power may be delivered between the RF power source device system (e.g., 340) and each of the at least two transducers in different ways. For example, in some embodiments, (1) the first transducer set 530*a* may include two or more of the transducers of the selected at least some of the transducers in the distribution, and the first transmission of power between the RF power source device system (e.g., 340) and each transducer included in the first transducer set 530*a* is transmitted simultaneously between the RF power source device system and each transducer included in the first transducer set 530*a*; (2) the second transducer set 530*b* may include two or more of the transducers of the selected at least some of the transducers in the distribution, and the second transmission of power between the RF power source device system and each transducer included in the second transducer set 530*b* is transmitted simultaneously between the RF power source device system and each transducer included in the second transducer set 530*b*; or both (1) and (2). In some embodiments, a start of a transmission of the first transmission of power between the RF power source device system (e.g., 340) and a first transducer in the first transducer set 530*a* occurs after a start of a transmission of the first transmission of power between the RF power source device system (e.g., 340) and a second transducer in the first transducer set 530*a*.

In some embodiments, the first transducer set 530*a* includes a first transducer of the selected at least some of the transducers in the distribution and another transducer of the selected at least some of the transducers in the distribution. The first transducer included in the first transducer set 530*a* may be positioned in the distribution sufficiently close to the another transducer included in the first transducer set 530*a* to cause a confluence of ablated tissue regions formed by the first transducer included in the first transducer set 530*a* and the another transducer included in the first transducer set 530*a* during a simultaneous occurrence of the first transmission of power between the RF power source device system and each of the first transducer included in the first transducer set 530*a* and the another transducer included in the first transducer set 530*a*. For example, in some embodiments associated with FIG. 5F, a first group of particular transducers in the first transducer set 530*a* corresponding to transducer graphical elements 502Q6 and 502R6 are positioned sufficiently close to one another to form a confluence of the their respective ablated tissue regions during a simultaneous transmission of the first transmission of power between the RF power source device system (e.g., 340) and the first group of particular transducers. It is noted that in various ones of these embodiments, the electrical property of the first transmission of power transmitted between the RF power source device system and the first transducer included in the first transducer set 530*a* may include a first phase angle of the at least one phase angle in the first range of phase angles, and the electrical property of the first transmission of power transmitted between the RF power source device system and the another transducer included in the first transducer set 530*a* includes a second phase angle of the at least one phase angle in the first range of phase angles. The second phase angle may be different than the first phase angle in some embodiments. In some embodiments (e.g., where bipolar ablation may be acceptable or preferable), a phase difference between this second phase angle and this first phase angle is sufficient to cause bipolar (or blended bipolar-monopolar in some embodiments) tissue ablation between respective regions of the tissue contacted by, or ablated by, the first transducer included in the first transducer set 530*a* and the another transducer (e.g., a second transducer) included in the first transducer set 530*a*. It is noted, however, that these first and second phase angles still form a part of the first range of phase angles which does not overlap the second range of phase angles associated with the second transmission of power. In some embodiments (e.g., where bipolar ablation is not acceptable or preferable), a phase difference between this second phase angle and this first phase angle is insufficient to cause bipolar (or blended bipolar-monopolar, in some embodiments) tissue ablation between respective regions of the tissue contacted by, or ablated by, the first and the second transducers included in the first transducer set 530*a*. In some embodiments, a phase difference between the second phase angle and the first phase angle does not exceed 10 degrees. In some embodiments, a phase difference between the second phase angle and the first phase angle that does not exceed 10 degrees is typically considered insufficient to cause bipolar tissue ablation between respective regions of the tissue contacted by, or ablated by, the first and the second transducers included in the first transducer set 530*a*.

It is noted that, even if a potential difference between the first and the second transducers included in the first transducer set 530*a* is insufficient to cause conventional bipolar ablation of tissue, a confluence between their respective ablated tissue regions may still occur if a sufficiently close enough distance exists between the first and the second transducers included in the first transducer set 530*a*. For example, in some embodiments associated with FIG. 5F, a group of particular transducers in the first transducer set 530*a* corresponding to transducer graphical elements 502Q6 and 502R6 are positioned sufficiently close to one another to form a confluence of the their respective ablated tissue regions during a simultaneous transmission of the first transmission of power between the RF power source device system (e.g., 340) and the group of particular transducers.

In some embodiments, monopolar ablation is implemented for the transducers within a given transducer set (e.g., each of 530*a* and 530*b*). In some embodiments, such implementation for any particular intra-bodily-cavity (e.g., intra-cardiac cavity) transducer effects a transmission of higher or greater power between an electrode of the particular intra-bodily-cavity transducer and an outside-the-bodily-cavity return electrode (e.g., indifferent electrode 326) than between the electrode of the intra-bodily-cavity particular transducer and elsewhere within the bodily cavity (e.g., to another intra-bodily-cavity electrode or group of intra-bodily-cavity electrodes). The higher or greater power transmitted between the electrode of the particular intra-bodily-cavity transducer and the outside-the-bodily-cavity return electrode causes the corresponding tissue ablation having ablation characteristics that are similar to monopolar or primarily monopolar in nature.

For example, in various embodiments, during the simultaneous occurrence of the first transmission of power between the RF power source device system (e.g., 340) and each of the first transducer included in the first transducer set 530*a* and the another transducer included in the first transducer set 530*a* (e.g., the second transducer in the first transducer set 530*a* described above), at least a difference between respective electrical potentials of the first transducer and the another transducer causes relatively higher current to be transmitted between either the first transducer or the another transducer and a set of one or more transducers not including any transducer in the first transducer set 530*a* than relatively lower current caused to be transmitted between the first transducer and the another transducer. In some of these various embodiments, relatively higher current caused to be transmitted between either the first transducer or the another transducer and the set of one or more transducers not including any transducer in the first transducer set 530*a* may be sufficiently high to cause tissue ablation while the relatively lower current caused to be transmitted between the first transducer and the another transducer may be insufficient to cause tissue ablation. In some of these various embodiments, the set of one or more transducers not including any transducer in the first transducer set 530*a* may provide a return for the relatively higher current caused to be transmitted by the either of the first transducer and the another transducer in the first transducer set 530*a*. In some of these various embodiments, the set of one or more transducers not including any transducer in the first transducer set 530*a* includes an indifferent electrode (e.g., indifferent electrode 326) positioned outside the bodily cavity (for example on a skin based-surface of a body comprising the bodily cavity). In some of these various embodiments, the set of one or more transducers not including any transducer in the first transducer set 530*a* includes at least one transducer that does not include any transducer included in the second transducer set 530*b* (for example, indifferent electrode 326 or a transducer of the selected transducers not identified by the instructions associated with block 606 for inclusion in the second transducer set 530*b*). In some of these various embodiments, the set of one or more transducers not including any transducer in the first transducer set 530*a* includes at least one transducer included in the second transducer set 530*b*. In some of these various embodiments, the set of one or more transducers not including any transducer in the first transducer set 530*a* includes at least one transducer of the plurality of transducers other than each transducer included in the first transducer set 530*a* and other than each transducer included in the second transducer set 530*b* (for example, a transducer selected in accordance with the instructions associated with block 604 or a transducer identified by the instructions associated with block 606 for inclusion in one the plurality of transducer sets other than the first transducer set 530*a* and the second transducer set 530*b*).

In some of these various embodiments, it is noted that when the set of one or more transducers not including any transducer in the first transducer set 530*a* includes two or more transducers, the relatively higher current caused to be transmitted between either the first transducer or the another transducer and the set of one or more transducers is provided by the combined currents between the either of the first transducer or the another transducer and the set of two or more transducers. During the simultaneous occurrence of the first transmission of power between the RF power source device system (e.g., 340) and each of the first transducer included in the first transducer set 530*a* and the another transducer included in the first transducer set 530*a*, multiple electric currents may flow from either the first transducer or the another transducer and the set of two or more transducers not including any transducer in the first transducer set 530*a*, and the multiple currents in combination are sufficient to cause tissue ablation while the relatively lower current transmitted between the first transducer and the another transducer may be insufficient for tissue ablation. That is, a current density provided by the multiple currents proximate to either of the first transducer and the another transducer may be sufficient to form the respective ablated tissue region even though the multiple currents travel to multiple locations (e.g., lower electric potential sites that provide respective returns for the electric circuits). In this manner, even if the relatively lower current transmitted between the first transducer and the another transducer in the first transducer set 530*a* is insufficient to cause tissue ablation, respective ablated tissue regions may still be formed by each of the first transducer and the another transducer provided in the first transducer set 530*a*, and confluence of these ablated tissue regions may arise if these transducers are sufficiently close to one another.

Similarly, in some embodiments, the identification instructions associated with block 606*a* may be configured to identify the first transducer set 530*a* such that during the simultaneous transmission of the first transmission of power between the RF power source device system and each respective one of the transducers included in the first transducer set 530*a*, at least a difference between respective electrical potentials of any two of the transducers included in the first transducer set 530*a* causes relatively higher current to be transmitted between either of the any two transducers included in the first transducer set 530*a* and a first set of one or more transducers not including any transducer in the first transducer set 530*a* than relatively lower current caused to be transmitted between the transducers of the any two of the transducers included in the first transducer set 530*a*. The identification instructions associated with block 606*b* may be configured to identify the second transducer set 530*b* such that during the simultaneous transmission of the second transmission of power between the RF power source device system and each respective one of the transducers included in the second transducer set 530*b*, at least a difference between respective electrical potentials of any two of the transducers included in the second transducer set 530*b* causes relatively higher current to be transmitted between either of the any two transducers included in the second transducer set 530*b* and a second set of one or more transducers not including any transducer in the second transducer set 530*b* than relatively lower current caused to be transmitted between the transducers of the any two of the transducers included in the second transducer set 530*b*. The identification instructions associated with block 606 may be configured to identify each of the first transducer set 530*a* and the second transducer set 530*b* such that a particular distance between any particular transducer included in the first transducer set 530*a* and any particular transducer included in the second transducer set 530*b* is sufficient to avoid a confluence of ablated tissue regions formed by the particular transducer included in the first transducer set 530*a* and the particular transducer included in the second transducer set 530*b* during the simultaneous occurrence of the first transmission of power and the second transmission of power.

It is noted that that there are different ways in which a difference between the respective electric potentials may be generated between transducers, such as a first transducer included in the first transducer set 530*a* and another transducer included in the first transducer set 530*a* (or any other pair of transducers within or even between sets). For example, in some embodiments, the electrical property of the first transmission of power transmitted (e.g., block 608*a*) between the RF power source device system (e.g., 340) and the first transducer included in the first transducer set 530*a* includes a first phase angle of the at least one phase angle in the first range of phase angles, the electrical property of the first transmission of power transmitted between the RF power source device system and the another transducer included in the first transducer set 530*a* includes a second phase angle of the at least one phase angle in the first range of phase angles, and the difference between the respective electric potentials of the first transducer and the another transducer corresponds to, at least in part, a phase difference between the first phase angle and the second phase angle. Without limitation, differences in signal amplitudes or frequencies may be employed to generate, at least in part, a required potential difference in other embodiments.

In some embodiments, the instructions associated with block 606 may be configured to identify the respective transducer sets not only to, for example, ensure that a confluence of ablated tissue regions does not exist between transducers in different transducer sets at different phase angles, but also to honor a manner in which the transducers were selected (e.g., to arrive at the configuration of FIG. 5E or any other configuration of selected transducers), when such honoring does not impact higher priority rules (e.g., safety or mechanical limitations) associated with the instructions of block 606. For example, a user might indirectly select the transducers associated with transducer graphical elements 502R6 and 502Q6 (e.g., FIG. 5E, 5F) by selecting between graphical element 504a, whereas the user might directly select the transducer associated with transducer graphical element 502O7 by directly selecting such transducer graphical element 502O7. In this case, in some embodiments, the instructions associated with block 606 may identify the transducers associated with transducer graphical elements 502R6 and 502Q6 to be activated concurrently according to the instructions associated with block 608, so as to cause a confluence of ablated tissue regions therebetween during a single activation iteration (e.g., FIG. 5F). In some embodiments, the instructions associated with block 606 may identify the transducer associated with transducer graphical element 502O7 to be activated in isolation (e.g., by being sufficiently distant from any other transducer so as not to cause a confluence of ablated tissue regions with such other transducer, albeit concurrently with other transducers in the same set, e.g., 502R6 and 502Q6, in some embodiments) during a single activation iteration (e.g., FIG. 5F). Accordingly, in some embodiments, a manner in which transducers are selected may dictate whether or not transducers in a same transducer set (e.g., 530a) are activated to cause a confluence of ablated tissue regions during a single activation iteration (e.g., each of FIGS. 5F and 5G representing an activation iteration).

For example, in some embodiments, (1) a first transducer included in the first transducer set 530a is positioned in the distribution sufficiently close to another transducer included in the first transducer set 530a to cause a confluence of ablated tissue regions formed by the first transducer included in the first transducer set 530a and the another transducer included in the first transducer set 530a during the simultaneous transmission of the first transmission of power between the RF power source device system (e.g., 340) and each respective one of the transducers included in the first transducer set 530a; (2) a second transducer included in the second transducer set 530b is positioned in the distribution sufficiently close to another transducer included in the second transducer set 530b to cause a confluence of ablated tissue regions formed by the second transducer included in the second transducer set 530b and the another transducer included in the second transducer set 530b during the simultaneous transmission of the second transmission of power between the RF power source device system and each respective one of the transducers included in the second transducer set 530b; or both (1) and (2). For example, in FIG. 5F, a first group of particular transducers in the first transducer set 530a corresponding to transducer graphical elements 502Q6 and 502R6 are considered positioned sufficiently close to one another to form a confluence of their respective ablated tissue regions during a simultaneous transmission of the first transmission of power between the RF power source device system (e.g., 340) and the first group of particular transducers, and a second group of particular transducers in the second transducer set 530b corresponding to transducer graphical elements 502P10 and 502Q10 are considered positioned sufficiently close to one another to form a confluence of their respective ablated tissue regions during a simultaneous transmission of the second transmission of power between the RF power source device system (e.g., 340) and the second group of particular transducers.

In some embodiments, the first transducer set 530a includes a first transducer of the selected at least some of the transducers in the distribution and another transducer of the selected at least some of the transducers in the distribution, and the first transducer included in the first transducer set 530a is positioned in the distribution sufficiently distant from the another transducer included in the first transducer set 530a to avoid causing a confluence of ablated tissue regions formed by the first transducer included in the first transducer set 530a and the another transducer included in the first transducer set 530a during a simultaneous occurrence of the first transmission of power between the RF power source device system and each of the first transducer included in the first transducer set 530a and the another transducer included in the first transducer set 530a. For example, a group of particular transducers in the first transducer set 530a corresponding to transducer graphical elements 502Q6 and 502O7 are considered positioned sufficiently distant from one another to avoid forming a confluence of their respective ablated tissue regions during a simultaneous transmission of the first transmission of power between the RF power source device system (e.g., 340) and the group of particular transducers. In some embodiments, the electrical property of the first transmission of power transmitted between the RF power source device system (e.g., 340) and the first transducer included in the first transducer set 530a includes a first phase angle of the at least one phase angle in the first range of phase angles, the electrical property of the first transmission of power transmitted between the RF power source device system and the another transducer included in the first transducer set 530a includes a second phase angle of the at least one phase angle in the first range of phase angles, and the second phase angle is different than the first phase angle. A phase difference between the second phase angle and the first phase angle may not exceed 10 degrees in some embodiments.

In some embodiments, the first transducer set 530a includes at least three transducers of the selected at least some of the transducers in the distribution and at least a first one of the at least three transducers included in the first transducer set 530a is positioned in the distribution sufficiently close to a second one of the at least three transducers included in the first transducer set 530a to cause a confluence of ablated tissue regions formed by the first one of the at least three transducers included in the first transducer set 530a and the second one of the at least three transducers included in the first transducer set 530a during a simultaneous occurrence of the first transmission of power between the RF power source device system (e.g., 340) and each transducer included in the first transducer set 530a, and at least the first one of the at least three transducers included in the first transducer set 530a is positioned in the distribution sufficiently distant from a third one of the at least three transducers included in the first transducer set 530a to avoid causing a confluence of ablated tissue regions formed by the first one of the at least three transducers included in the first transducer set 530a and the third one of the at least three transducers included in the first transducer set 530a during the simultaneous occurrence of the first transmission of power between the RF power source device system and each transducer included in the first transducer set. For example, in some embodiments associated with FIG. 5F, a first group of particular transducers in the first transducer set 530a corresponding to transducer graphical elements 502Q6 and 502R6 are considered positioned sufficiently close to one another to form a confluence of their respective ablated tissue regions during a simultaneous transmission of the first transmission of power between the RF power source device system (e.g., 340) and the first group of particular transducers, while a second group of particular transducers in the first transducer set 530a corresponding to transducer graphical elements 502R6 and 502O7 are considered positioned sufficiently distant from one another to avoid forming a confluence of their respective ablated tissue regions during a simultaneous transmission of the first transmission of power between the RF power source device system (e.g., 340) and the second group of particular transducers.

In some embodiments, the second one of the at least three transducers included in the first transducer set 530*a* is positioned in the distribution sufficiently distant from the third one of the at least three transducers included in the first transducer set 530*a* to avoid causing a confluence of ablated tissue regions formed by the second one of the at least three transducers included in the first transducer set 530*a* and the third one of the at least three transducers included in the first transducer set 530*a* during the simultaneous occurrence of the first transmission of power between the RF power source device system and each transducer included in the first transducer set 530*a*. For example, the particular transducers in the first transducer set 530*a* corresponding to transducer graphical elements 502Q6 and 502O7 (e.g., transducer graphical elements 502Q6 and 502O7 being respectively identified as corresponding the second one and the third one of the at least three transducers in the previous example described above) are considered positioned sufficiently distant from one another to avoid forming a confluence of their respective ablated tissue regions during a simultaneous transmission of the first transmission of power between the RF power source device system (e.g., 340) and the at least three transducers included in the first transducer set 530*a*. In some of these embodiments, the electrical property of the first transmission of power transmitted between the RF power source device system (e.g., 340) and each of the at least three transducers included in the first transducer set 530*a* includes a same phase angle of the at least one phase angle in the first range of phase angles. In some of these embodiments, the electrical property of the first transmission of power transmitted between the RF power source device system (e.g., 340) and each of the first one and the second one of the at least three transducers included in the first transducer set 530*a* during the simultaneous occurrence of the first transmission of power between the RF power source device system and each transducer included in the first transducer set 530*a* includes a same phase angle of the at least one phase angle in the first range of phase angles. In some of these embodiments, the electrical property of the first transmission of power transmitted between the RF power source device system (e.g., 340) and the third one of the at least three transducers included in the first transducer set 530*a* during the simultaneous occurrence of the first transmission of power between the RF power source device system and each transducer included in the first transducer set 530*a* includes a phase angle of the at least one phase angle in the first range of phase angles different than the same phase angle of the at least one phase angle in the first range of phase angles.

In some embodiments, a first one of the transducers included in the first transducer set 530*a* is positioned in the distribution sufficiently close to a second one of the transducers included in the first transducer set 530*a* to cause a confluence of ablated tissue regions formed by the first one of the transducers included in the first transducer set 530*a* and the second one of the transducers included in the first transducer set 530*a* during the simultaneous transmission of the first transmission of power between the RF power source device system and each respective one of the transducers included in the first transducer set 530*a*, and the first one of the transducers included in the first transducer set 530*a* is positioned in the distribution sufficiently distant from a third one of the transducers included in the first transducer set to avoid causing a confluence of ablated tissue regions formed by the first one of the transducers included in the first transducer set 530*a* and the third one of the transducers included in the first transducer set 530*a* during the simultaneous transmission of the first transmission of power between the RF power source device system and each respective one of the transducers included in the first transducer set 530*a*. For example in some embodiments associated with FIG. 5F, a first group of particular transducers in the first transducer set 530*a* corresponding to transducer graphical elements 502Q6 and 502R6 are considered positioned sufficiently close to one another to form a confluence of their respective ablated tissue regions during a simultaneous transmission of the first transmission of power between the RF power source device system (e.g., 340) and each respective one of the transducers included in the first transducer set 530*a*, while a second group of particular transducers in the first transducer set 530*a* corresponding to transducer graphical elements 502R6 and 502O7 are considered positioned sufficiently distant from one another to avoid forming confluence of their respective ablated tissue regions during the simultaneous transmission of the first transmission of power between the RF power source device system (e.g., 340) and each respective one of the transducers included in the first transducer set 530*a*. Additionally, in some particular embodiments associated with FIG. 5F, particular transducers in the first transducer set 530*a* corresponding to transducer graphical elements 502Q6 and 502O7 are considered positioned sufficiently distant from one another to avoid forming a confluence of their respective ablated tissue regions during the simultaneous transmission of the first transmission of power between the RF power source device system (e.g., 340) and each respective one of the transducers included in the first transducer set 530*a*. The transducers in the second transducer set 530*b* may be activated in a similar manner. For example, in some embodiments associated with FIG. 5F, a first group of particular transducers in the second transducer set 530*b* corresponding to transducer graphical elements 502P10 and 502Q10 are considered positioned sufficiently close to one another to form a confluence of their respective ablated tissue regions during a simultaneous transmission of the second transmission of power between the RF power source device system (e.g., 340) and each respective one of the transducers included in the second transducer set 530*b*.

In some embodiments, after the first activation iteration of FIG. 5F of the first and second transducer sets 530*a*, 530*b* has been completed (e.g., their respective ablated tissue regions have been formed), method 600 may continue with additional activation iterations of the plurality of transducer sets identified via the instructions associated with block 606. For example, in some embodiments, FIG. 5G shows a next activation iteration where each of the first transducer set 530*a* and the second transducer set 530*b* is in a post-energy delivery state (e.g., after a completion of the first transmission of power and a completion of the second transmission of power of FIG. 5F), and two additional transducer sets (e.g., third and fourth transducer sets in this embodiment) 530*c* and 530*d* identified as per the instructions associated with block 606 are activated according to the instructions associated with block 608. In some embodiments, the third and fourth transducer sets 530*c* and 530*d* may become the 'first' and 'second' transducer sets referred to in blocks 606*a*, 606*b*, 608*a*, and 608*b*, and the third and fourth transducer sets 530*c* and 530*d* may be identified and activated according to the rules and characteristics of the first and second transducer sets 530*a*, 530*b*, discussed above. In this regard, first transmission instructions, which may be the same as, or similar to, the instructions associated with block 608*a* may be configured to cause a third transmission of power between the RF power source device system (e.g., 340) and each transducer in the transducer set 530*c*, the third transmission of power including an electrical property including at least one phase angle in a third range of phase angles, the electrical property being a current or a voltage. Second transmission instructions, the same as, or similar to, the instructions associated with block 606*b* are configured to cause a fourth transmission of power between the RF power source device system and each transducer in the transducer set 530*d*, the fourth transmission of power comprising the electrical property including at least one phase angle in a fourth range of phase angles, and the fourth range of phase angles not overlapping the third range of phase angles, and the third transmission of power occurring simultaneously with the fourth transmission of power. In some embodiments, (1) the third range of phase angles is the same as the above-discussed first range of phase angles; (2) the fourth range of phase angles is the same as the above-discussed second range of phase angles; or both (1) and (2). In some embodiments, (1) the third range of phase angles is different from each of the first range of phase angles and the second range of phase angles; (2) the fourth range of phase angles is different from each of the first range of phase angles and the second range of phase angles; or both (1) and (2).

In various embodiments associated with FIG. 5G, the identification instructions associated with block 606 may be configured to identify each respective transducer in each of the transducer set 530*c* and the transducer set 530*d* as a particular one of the selected at least some of the transducers in the distribution, the identified particular ones of the selected at least some of the transducers arranged in the distribution to prevent a confluence of an ablated tissue region formed by any transducer included in the transducer set 530*c* and an ablated tissue region formed by any transducer included in the transducer set 530*d* from forming during the simultaneous occurrence of the third transmission of power and the fourth transmission of power.

In some embodiments associated with FIG. 5G, a confluence of the respective ablated tissue regions formed by a transmission of the third transmission of power to the respective transducers of the transducer set 530*c* (e.g., the respective transducers associated with the transducer graphical elements 502R7 and 502S7 having identifiers 513 "R:7" and "S:7", respectively) occurs. In some embodiments associated with FIG. 5G, a confluence of the respective ablated tissue regions formed by a transmission of the fourth transmission of power to the respective transducers of the transducer set 530*d* (e.g., the respective transducers associated with the transducer graphical elements 502R9 and 502S9 having identifiers 513 "R:9" and "S:9", respectively) is formed during the fourth transmission of power. In some embodiments, a particular electrical characteristic other than phase (e.g., amplitude or frequency) associated with the third transmission of power may be the same or different than the respective corresponding electrical characteristic associated with either the first transmission of power or second transmission of power described above. In some embodiments, a particular electrical characteristic other than phase (e.g., amplitude or frequency) associated with the fourth transmission of power may be the same or different than the respective corresponding electrical characteristic associated with either the first transmission of power or second transmission of power described above. In some embodiments, one or more activation iterations (like FIGS. 5F and 5G) are repeated (e.g., various instructions of method 600 are repeated) until all of the selected transducers have been activated, as for example, shown by the post-energy delivery states of FIG. 5H.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above may provide further embodiments.

These and other changes may be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A transducer-activation system comprising:
   a data processing device system;
   an input-output device system communicatively connected to the data processing device system; and
   a memory device system communicatively connected to the data processing device system and storing a program executable by the data processing device system, the program configured to cause the data processing device system to communicate, via the input-output device system, with a power source device system and a plurality of transducers located on a catheter device, the plurality of transducers arrangeable in a distribution in a bodily cavity, the program comprising:
   reception instructions configured to cause reception, via the input-output device system, of a selection of at least some of the transducers in the distribution;
   identification instructions configured to identify a plurality of transducer sets from the selected at least some of the transducers in the distribution, the plurality of transducer sets including at least a first transducer set and a second transducer set, each of the transducer sets comprising at least one transducer of the selected at least some of the transducers in the distribution;
   first transmission instructions configured to cause a first transmission of power between the power source device system and each transducer in the first transducer set, the first transmission of power comprising an electrical property including at least one phase angle in a first range of phase angles, the electrical property being a current or a voltage; and
   second transmission instructions configured to cause a second transmission of power between the power source device system and each transducer in the second transducer set, the second transmission of power comprising the electrical property including at least one phase angle in a second range of phase angles, wherein the second range of phase angles does not overlap the first range of phase angles, each transducer included in the first transducer set and each transducer included in the second transducer set is operable to form a respective ablated tissue region in response to transmission of a respective one of the first transmission of power and the second transmission of power, and the first transmission of power and the second transmission of power occur simultaneously at least in part over a time interval (a) during the reception of the selection, (b) after a completion of the reception of the selection, or both (a) and (b), and wherein the identification instructions are configured to at least prevent the first transducer set from including a particular transducer in the selected at least some of the transducers in the distribution that is sufficiently close to any respective transducer in the distribution included in the second transducer set to cause a confluence of respective ablated tissue regions therebetween if the first transmission of power was to be transmitted between the power source device system and the particular transducer simultaneously with the second transmission of power between the power source device system and the respective transducer included in the second transducer set.

2. The transducer-activation system of claim 1 wherein the electrical property of the first transmission of power transmitted between the power source device system and at least a first transducer in the first transducer set includes a first particular phase angle of the at least one phase angle in the first range of phase angles, and the electrical property of the second transmission of power transmitted between the power source device system and at least a second transducer in the second transducer set includes a second particular phase angle of the at least one phase angle in the second range of phase angles, a phase difference between the first particular phase angle and the second particular phase angle being 180 degrees.

3. The transducer-activation system of claim 1 wherein the electrical property of the first transmission of power transmitted between the power source device system and at least a first transducer in the first transducer set includes a first particular phase angle of the at least one phase angle in the first range of phase angles, and the electrical property of the second transmission of power transmitted between the power source device system and at least a second transducer in the second transducer set includes a second particular phase angle of the at least one phase angle in the second range of phase angles, a phase difference between the first particular phase angle and the second particular phase angle being between 10 degrees and 180 degrees.

4. The transducer-activation system of claim 1 wherein the identification instructions are configured to identify each respective transducer in each of the first transducer set and the second transducer set as a particular one of the selected at least some of the transducers in the distribution, the identified particular ones of the selected at least some of the transducers arranged in the distribution to prevent a confluence of an ablated tissue region formed by any transducer included in the first transducer set and an ablated tissue region formed by any transducer included in the second transducer set from forming during the simultaneous occurrence of the first transmission of power and the second transmission of power.

5. The transducer-activation system of claim 1 wherein, for each respective transducer included in the second transducer set, the particular transducer in the selected at least some of the transducers in the distribution is a particular respective distance from the respective transducer included in the second transducer set, and the identification instructions are configured to at least prevent the first transducer set from including the particular transducer, if it is determined according to the identification instructions that a confluence of an ablated tissue region formed by the particular transducer and an ablated tissue region formed by the respective transducer included in the second transducer set would, if the first transmission of power was to be transmitted between the power source device system and the particular transducer simultaneously with the second transmission of power between the power source and the respective transducer included in the second transducer set, occur due at least to the particular respective distance and a particular phase difference, the particular phase difference being between (1) a first particular phase angle of the at least one phase angle in the first range of phase angles that would be transmitted according to the first transmission of power between the power source device system and the particular transducer if the particular transducer was included in the first transducer set, and (2) a second particular phase angle of the at least one phase angle in the second range of phase angles to be transmitted according to the second transmission of power between the power source device system and the respective transducer included in the second transducer set.

6. The transducer-activation system of claim 1 wherein the first transducer set comprises a first transducer of the selected at least some of the transducers in the distribution and another transducer of the selected at least some of the transducers in the distribution, and wherein the first transducer included in the first transducer set is positioned in the distribution sufficiently close to the another transducer included in the first transducer set to cause a confluence of ablated tissue regions formed by the first transducer included in the first transducer set and the another transducer included in the first transducer set during a simultaneous occurrence of the first transmission of power between the power source device system and each of the first transducer included in the first transducer set and the another transducer included in the first transducer set.

7. The transducer-activation system of claim 6
wherein the electrical property of the first transmission of power transmitted between the power source device system and the first transducer included in the first transducer set includes a first phase angle of the at least one phase angle in the first range of phase angles, wherein the electrical property of the first transmission of power transmitted between the power source device system and the another transducer included in the first transducer set includes a second phase angle of the at least one phase angle in the first range of phase angles, and wherein the second phase angle is different than the first phase angle.

8. The transducer-activation system of claim 7 wherein a phase difference between the second phase angle and the first phase angle does not exceed 10 degrees.

9. The transducer-activation system of claim 6 wherein, during the simultaneous occurrence of the first transmission of power between the power source device system and each of the first transducer included in the first transducer set and the another transducer included in the first transducer set, at least a difference between respective electrical potentials of the first transducer and the another transducer causes relatively higher current to be transmitted between either the first transducer or the another transducer and a set of one or more transducers not including any transducer in the first transducer set than relatively lower current caused to be transmitted between the first transducer and the another transducer.

10. The transducer-activation system of claim 9
wherein the electrical property of the first transmission of power transmitted between the power source device system and the first transducer included in the first transducer set includes a first phase angle of the at least one phase angle in the first range of phase angles,
wherein the electrical property of the first transmission of power transmitted between the power source device system and the another transducer included in the first transducer set includes a second phase angle of the at least one phase angle in the first range of phase angles, and
wherein the difference between the respective electric potentials of the first transducer and the another transducer corresponds to, at least in part, a phase difference between the first phase angle and the second phase angle.

11. The transducer-activation system of claim 9 wherein the set of one or more transducers not including any transducer in the first transducer set includes an indifferent electrode positioned outside of the bodily cavity.

12. The transducer-activation system of claim 9 wherein the set of one or more transducers not including any transducer in the first transducer set includes at least one transducer that does not include any transducer included in the second transducer set.

13. The transducer-activation system of claim 9 wherein the set of one or more transducers not including any transducer in the first transducer set includes at least one transducer included in the second transducer set.

14. The transducer-activation system of claim 9 wherein the set of one or more transducers not including any transducer in the first transducer set includes at least one transducer of the plurality of transducers other than each transducer included in the first transducer set and other than each transducer included in the second transducer set.

15. The transducer-activation system of claim 1 wherein the first transducer set comprises a first transducer of the selected at least some of the transducers in the distribution and another transducer of the selected at least some of the transducers in the distribution, and wherein the first transducer included in the first transducer set is positioned in the distribution sufficiently distant from the another transducer included in the first transducer set to avoid causing a confluence of ablated tissue regions formed by the first transducer included in the first transducer set and the another transducer included in the first transducer set during a simultaneous occurrence of the first transmission of power between the power source device system and each of the first transducer included in the first transducer set and the another transducer included in the first transducer set.

16. The transducer-activation system of claim 15
wherein the electrical property of the first transmission of power transmitted between the power source device system and the first transducer included in the first transducer set includes a first phase angle of the at least one phase angle in the first range of phase angles,
wherein the electrical property of the first transmission of power transmitted between the power source device system and the another transducer included in the first transducer set includes a second phase angle of the at least one phase angle in the first range of phase angles, and
wherein the second phase angle is different than the first phase angle.

17. The transducer-activation system of claim 16 wherein a phase difference between the second phase angle and the first phase angle does not exceed 10 degrees.

18. The transducer-activation system of claim 1 wherein the first transducer set comprises at least three transducers of the selected at least some of the transducers in the distribution and wherein:
at least a first one of the at least three transducers included in the first transducer set is positioned in the distribution sufficiently close to a second one of the at least three transducers included in the first transducer set to cause a confluence of ablated tissue regions formed by the first one of the at least three transducers included in the first transducer set and the second one of the at least three transducers included in the first transducer set during a simultaneous occurrence of the first transmission of power between the power source device system and each transducer included in the first transducer set; and
at least the first one of the at least three transducers included in the first transducer set is positioned in the distribution sufficiently distant from a third one of the at least three transducers included in the first transducer set to avoid causing a confluence of ablated tissue regions formed by the first one of the at least three transducers included in the first transducer set and the third one of the at least three transducers included in the first transducer set during the simultaneous occurrence of the first transmission of power between the power source device system and each transducer included in the first transducer set.

19. The transducer-activation system of claim 18 wherein the second one of the at least three transducers included in the first transducer set is positioned in the distribution sufficiently distant from the third one of the at least three transducers included in the first transducer set to avoid causing a confluence of ablated tissue regions formed by the second one of the at least three transducers included in the first transducer set and the third one of the at least three transducers included in the first transducer set during the simultaneous occurrence of the first transmission of power between the power source device system and each transducer included in the first transducer set.

20. The transducer-activation system of claim 18 wherein the electrical property of the first transmission of power transmitted between the power source device system and each of the at least three transducers included in the first transducer set includes a same phase angle of the at least one phase angle in the first range of phase angles.

21. The transducer-activation system of claim 18 wherein the electrical property of the first transmission of power transmitted between the power source device system and each of the first one and the second one of the at least three transducers included in the first transducer set during the simultaneous occurrence of the first transmission of power between the power source device system and each transducer included in the first transducer set includes a same phase angle of the at least one phase angle in the first range of phase angles.

22. The transducer-activation system of claim 21 wherein the electrical property of the first transmission of power transmitted between the power source device system and the third one of the at least three transducers included in the first transducer set during the simultaneous occurrence of the first transmission of power between the power source device system and each transducer included in the first transducer set includes a phase angle of the at least one phase angle in the first range of phase angles different than the same phase angle of the at least one phase angle in the first range of phase angles.

23. The transducer-activation system of claim 1 wherein (1) the at least one phase angle in the first range of phase angles comprises at least two phase angles; (2) the at least one phase angle in the second range of phase angles comprises at least two phase angles; or both (1) and (2).

24. The transducer-activation system of claim 1 wherein (1) the first transducer set comprises a first transducer of the selected at least some of the transducers in the distribution and another transducer of the selected at least some of the transducers in the distribution, the electrical property of the first transmission of power transmitted between the power source device system and the first transducer included in the first transducer set includes a first phase angle of the at least one phase angle in the first range of phase angles, and the electrical property of the first transmission of power transmitted between the power source device system and the another transducer included in the first transducer set includes another phase angle of the at least one phase angle in the first range of phase angles different than the first phase angle; (2) the second transducer set comprises a second transducer of the selected at least some of the transducers in the distribution and another transducer of the selected at least some of the transducers in the distribution, the electrical property of the second transmission of power transmitted between the power source device system and the second transducer included in the second transducer set includes a second phase angle of the at least one phase angle in the second range of phase angles, and the electrical property of the second transmission of power transmitted between the power source device system and the another transducer included in the second transducer set includes another phase angle of the at least one phase angle in the second range of phase angles different than the second phase angle; or both (1) and (2).

25. The transducer-activation system of claim 1 wherein (1) the electrical property of the first transmission of power between the power source device system and a first transducer included in the first transducer set includes a first portion including a first phase angle of the at least one phase angle in the first range of phase angles and a second portion including a second phase angle of the at least one phase angle in the first range of phase angles different than the first phase angle in the first range of phase angles; (2) the electrical property of the second transmission of power between the power source device system and a second transducer included in the second transducer set includes a first portion including a first phase angle of the at least one phase angle in the second range of phase angles and a second portion including a second phase angle of the at least one phase angle in the second range of phase angles different than the first phase angle in the second range of phase angles; or both (1) and (2).

26. The transducer-activation system of claim 1 wherein (1) the first transmission instructions are configured to cause the electrical property of the first transmission of power between the power source device system and each of at least a first transducer included in the first transducer set to modulate between a first phase angle of the at least one phase angle in the first range of phase angles and a second phase angle of the at least one phase angle in the first range of phase angles different than the first phase angle in the first range of phase angles; (2) the second transmission instructions are configured to cause the electrical property of the second transmission of power between the power source device system and each of at least a second transducer included in the second transducer set to modulate between a first phase angle of the at least one phase angle in the second range of phase angles and a second phase angle of the at least one phase angle in the second range of phase angles different than the first phase angle in the second range of phase angles; or both (1) and (2).

27. The transducer-activation system of claim 1 wherein the selected at least some of the transducers in the distribution include some but not all of the transducers in the distribution.

28. The transducer-activation system of claim 1 wherein the input-output device system comprises the plurality of transducers, and the distribution is an arrayed distribution comprising a plurality of intersecting rows and columns, a respective group of the transducers arranged along each of the rows and a respective group of the transducers arranged along each of the columns, and wherein the identification instructions are configured to at least prevent the first transducer set from including any transducer in the selected at least some of the transducers in the distribution that is positioned along any of the rows or columns adjacent any transducer in the distribution included in the second transducer set.

29. The transducer-activation system of claim 1 wherein the input-output device system comprises the plurality of transducers, and the transducers in the distribution are arranged in a grid comprising at least three rows and at least three columns, each of the columns arranged to intersect each of the rows at a respective intersection location, a respective one of the transducers arranged at each respective intersection location, and wherein the identification instructions are configured to at least prevent the first transducer set from including any transducer in the selected at least some of the transducers in the distribution whose respective intersection location is adjacent to the respective intersection location of any transducer in the distribution included in the second transducer set.

30. The transducer-activation system of claim 1 wherein the program further comprises:
    display instructions configured to cause the input-output device system to concurrently display:
    at least a map depicting a surface of a tissue wall of the bodily cavity, the surface interrupted by one or more openings; and
    a plurality of transducer graphical elements, each of the transducer graphical elements corresponding to at least part of a respective one of the plurality of transducers, a first spatial relationship between the displayed transducer graphical elements consistent with a second spatial relationship between the transducers, and
    wherein the display instructions are configured to display the respective transducer graphical elements corresponding to the selected at least some of the transducers in the distribution surrounding at least one of the one or more openings depicted in the map.

31. The transducer-activation system of claim 30 wherein the program further comprises information reception instructions configured to cause reception via the input-output device system of information from each of the plurality of transducers, and wherein the display instructions are configured to display the map based at least on the information received from the each of the plurality of transducers.

32. The transducer-activation system of claim 30 wherein the display instructions are further configured to display the respective transducer graphical elements corresponding to the selected at least some of the transducers in the distribution differently than the transducers graphical elements corresponding to particular ones of the plurality of transducers that do not form part of the selected at least some of the transducers in the distribution.

33. The transducer-activation system of claim 30 wherein the reception, via the input-output device system, of the selected at least some of the transducers in the distribution comprises reception of a user-based selection, via the input-output device system, of the selected at least some of the transducers in the distribution.

34. The transducer-activation system of claim 1 wherein the reception, via the input-output device system, of the selected at least some of the transducers in the distribution comprises reception of a user-based selection, via the input-output device system, of the selected at least some of the transducers in the distribution, and the identification instructions configured to identify the plurality of transducer sets from the selected at least some of the transducers in the distribution comprise machine-based identification of the plurality of transducer sets from the selected at least some of the transducers in the distribution.

35. The transducer-activation system of claim 1 wherein the identification instructions are configured to cause the first transducer set to include only transducers in the selected at least some of the transducers in the distribution that each are sufficiently distant from each respective transducer in the distribution included in the second transducer set to not cause a confluence of ablated tissue regions formed by any transducer in the first transducer set and any transducer in the second transducer set during the simultaneous occurrence of the first transmission of power and the second transmission of power.

36. The transducer-activation system of claim 1 wherein (1) the first transducer set comprises two or more of the transducers of the selected at least some of the transducers in the distribution, and the first transmission of power between the power source device system and each transducer included in the first transducer set is transmitted simultaneously between the power source device system and each transducer included in the first transducer set; (2) the second transducer set comprises two or more of the transducers of the selected at least some of the transducers in the distribution, and the second transmission of power between the power source device system and each transducer included in the second transducer set is transmitted simultaneously between the power source device system and each transducer included in the second transducer set; or both (1) and (2).

* * * * *